US 9,982,181 B2
May 29, 2018

(12) United States Patent
Wolf et al.

(10) Patent No.: US 9,982,181 B2
(45) Date of Patent: *May 29, 2018

(54) MULTI-SITE MODIFIED SP1 POLYPEPTIDES AND USES THEREOF

(71) Applicant: Fulcrum S.P. Materials Ltd., Yavne (IL)

(72) Inventors: Amnon Wolf, Herzlia Pituach (IL); Nimrod Litvak, Tel-Aviv (IL); Elena Grimberg, Rechovot (IL); Galit Cohen, Rechovot (IL); Arnon Heyman, Gedera (IL); Izhar Medalsy, Modiln (IL); Danny Porath, Jerusalem (IL); Oded Shoseyov, Karme Yosef (IL); Asa Eitan, Tel-Aviv (IL)

(73) Assignee: SP Nano Ltd., Yavne (IL)

( * ) Notice: Subject to any disclaimer, the term of this patent is extended or adjusted under 35 U.S.C. 154(b) by 16 days.

This patent is subject to a terminal disclaimer.

(21) Appl. No.: 14/623,041

(22) Filed: Feb. 16, 2015

(65) Prior Publication Data

US 2015/0152311 A1 Jun. 4, 2015

Related U.S. Application Data

(62) Division of application No. 13/394,181, filed as application No. PCT/IL2010/000705 on Aug. 26, 2010, now Pat. No. 8,957,189.

(60) Provisional application No. 61/358,973, filed on Jun. 28, 2010, provisional application No. 61/272,230, filed on Sep. 3, 2009.

(51) Int. Cl.
| | |
|---|---|
| C07K 14/415 | (2006.01) |
| C09K 5/14 | (2006.01) |
| B82Y 30/00 | (2011.01) |
| H01B 1/24 | (2006.01) |

(52) U.S. Cl.
CPC ............. C09K 5/14 (2013.01); B82Y 30/00 (2013.01); C07K 14/415 (2013.01); H01B 1/24 (2013.01); *Y10T 442/20* (2015.04); *Y10T 442/2426* (2015.04); *Y10T 442/2861* (2015.04)

(58) Field of Classification Search
CPC . C06K 5/14; H01B 1/24; B82Y 30/00; C07K 14/415; Y10T 442/20; Y10T 442/2426; Y10T 442/2861
See application file for complete search history.

(56) References Cited

U.S. PATENT DOCUMENTS

| | | | |
|---|---|---|---|
| 5,770,216 A | 6/1998 | Mitchnick et al. | |
| 6,010,771 A | 1/2000 | Isen et al. | |
| 7,462,462 B2 | 12/2008 | Shiba et al. | |
| 9,051,379 B2 * | 6/2015 | Wolf | B82Y 30/00 |
| 2005/0277160 A1 | 12/2005 | Shiba et al. | |
| 2006/0172282 A1 | 8/2006 | Naik et al. | |
| 2012/0202397 A1 | 8/2012 | Wolf et al. | |

FOREIGN PATENT DOCUMENTS

| | | |
|---|---|---|
| JP | 2004-002621 | 1/2004 |
| JP | 2004-121154 | 4/2004 |
| JP | 2006-516240 | 6/2006 |
| JP | 2008-054599 | 3/2008 |
| JP | 2009-502122 | 1/2009 |
| JP | 5863191 | 1/2016 |
| WO | WO 03/102020 | 12/2003 |
| WO | WO 2004/022697 | 3/2004 |
| WO | WO 2006/128261 | 12/2006 |
| WO | WO 2007/007325 | 1/2007 |
| WO | WO 2008/060294 | 5/2008 |
| WO | WO 2011/027342 | 3/2011 |

OTHER PUBLICATIONS

Plant Life Cytoskeleton (last viewed on Mar. 28, 2017).*
Wacey et al., Disentangling the perturbational effects of amino acid substitutions in the DNA-binding domain of p53., Hum Genet, 1999, vol. 104, pp. 15-22.*
Agarose from Sigma (last viewed in Mar. 30, 2016).*
Mica (last viewed on Mar. 30, 2017).*
Li et al. Current Approaches for Engineering Proteins with Diverse Biological Properties, Adv Exp Med Biol. (2007-B) vol. 620, pp. 18-33.*
Requisition by the Examiner dated Oct. 5, 2016 From the Canadian Intellectual Property Office Re. Application No. 2,772,491.
Notice of Reason for Rejection dated Jul. 12, 2016 From the Japanese Patent Office Re. Application No. 2015-140151 and Its Translation Into English.
Office Action dated Nov. 26, 2015 From the Israel Patent Office Re. Application No. 218428 and Its Translation Into English.
European Search Report and the European Search Opinion dated Nov. 6, 2015 From the European Patent Office Re. Application No. 15176962.7.
Poetschke et al. "A Novel Strategy to Incorporate Carbon Nanotubes Into Thermoplastic Matrices", Macromolecular Rapid Communications, XP055223375, 29(3): 244-251, Feb. 1, 2008. Abstract.
Veedu et al. "Multifunctional Coposites Using Reinforced Laminae With Carbon-Nanotube Forests", Nature Materials, XP002500845, 5: 457-462, Published Online May 7, 2006. Abstract.
Notice of Reason for Rejection dated Jun. 5, 2015 From the Japanese Patent Office Re. Application No. 2012-527446 and Its Translation Into English.
Communication Pursuant to Article 94(3) EPC dated Jan. 18, 2013 From the European Patent Office Re. Application No. 10761070.1.
Communication Pursuant toArticle 94(3) EPC dated Jun. 12, 2013 From the European Patent Office Re. Application No. 10761070.1.
Communication Relating to the Results of the Partial International Search dated Jan. 12, 2011 From the International Searching Authority Re. Application No. PCT/IL2010/000705.

(Continued)

*Primary Examiner* — Anand Desai

(57) ABSTRACT

The present invention, in some embodiments thereof, relates to material science in general, and, more particularly, to sequence variants of Stable Protein 1 (SP1), to uses thereof, for binding of carbon nanotubes, production of composite polymers and polymer materials, such as fabrics, based on SP1-polypeptide-carbon nanotube-complexes, and the use thereof for enhancing conductivity in tire.

21 Claims, 10 Drawing Sheets
(6 of 10 Drawing Sheet(s) Filed in Color)

(56) References Cited

OTHER PUBLICATIONS

International Search Report and the Written Opinion dated Mar. 10, 2011 From the International Searching Authority Re. PCT/IL2010/000705.
Notice of Reason for Rejection dated Oct. 21, 2014 From the Japanese Patent Office Re. Application No. 2012-527446 and Its Translation Into English.
Office Action dated Oct. 21, 2014 From the Israel Patent Office Re. Application No. 218428 and Its Translation Into English.
Official Action dated May 1, 2014 From the US Patent and Tradmark Office Re. U.S. Appl. No. 13/394,181.
Restriction Official Action dated Dec. 31, 2013 From the US Patent and Tradmark Office Re. U.S. Appl. No. 13/394,181.
Summons to Attend Oral Proceedings Pursuant to Rule 115(1) EPC dated Oct. 8, 2014 From the European Patent Office Re. Application No. 10761070.1.
Behrens et al. "Constrained Synthesis and Organization of Catalytically Active Metal Nanoparticles by Self-Assembled Protein Templates", Advances Materials, XP002613818, 21(34): 3515-3519, Jul. 2, 2009.
Heyman et al. "Float and Compress: Honeycomb-Like Array of a Highly Stable Protein Scaffold", Langmuir, XP002613819, 25(9): 5226-5229, May 5, 2009.
Heyman et al. "Multiple Display of Catalytic Modules on a Protein Scaffold: Nano-Fabrication of Enzyme Particles", Journal of Biotechnology, XP022259321, 131(4): 433-439, Sep. 20, 2007.
Heyman et al. "Protein Scaffold Engineering Towards Tunable Surface Attachment", Angewandte Chemie, International Edition, XP002613821, 48(49): 9290-9294, Sep. 22, 2009.
Heyman et al. "SP1 as a Novel Scaffold Building Block for Self-Assembly Nanofabrication of Submicron Enzymatic Structures", Nano Letters, XP002613820, 7(6): 1575-1579, Jun. 2007.
Medalsy et al. "SP1 Protein-Based Nanostructures and Arrays", Nano Letters, XP002545658, 8(2): 473-477, Jan. 15, 2008.
Oren et al. "A Novel Knowledge-Based Approach to Design Inorganic-Binding Peptides", Bioinformatics, 23(21): 2816-2822, 2007.
Porath et al. "SP1 Protein-Nanoparticle Hybrids as Building Blocks for Nanostructures: Memory Arrays and Nanowires", Trends in Nanotechnology, TNT 2008 Conference, Oviedo, Spain, Sep. 1-5, 2008, 2 P., 2008.
Shoseyov "Genetic Engineering of Self-Assembled Proteins", The Hebrew University of Jerusalem, The Center for Nanoscience and Nanotechnology, p. 1-3. http://nanoscience.huji.ac.il/researchers/shoseyov.htm, Printed May 17, 2009.
Wang et al. "Characterization of SP1, A Stress-Responsive, Boiling-Soluble, Homo-Oligomeric Protein From Aspen", Plant Physiology, 130: 865-875, Oct. 2002.
Communication Pursuant to Article 94(3) EPC dated Jun. 7, 2017 From the European Patent Office Re. Application No. 15176962.7. (4 Pages).
Machine Translation of Notice of Reason for Rejection dated May 23, 2017 From the Japanese Patent Office Re. Application No. 2015-140151. (2 Pages).
Notice of Reason for Rejection dated May 23, 2017 From the Japanese Patent Office Re. Application No. 2015-140151. (3 Pages).

\* cited by examiner

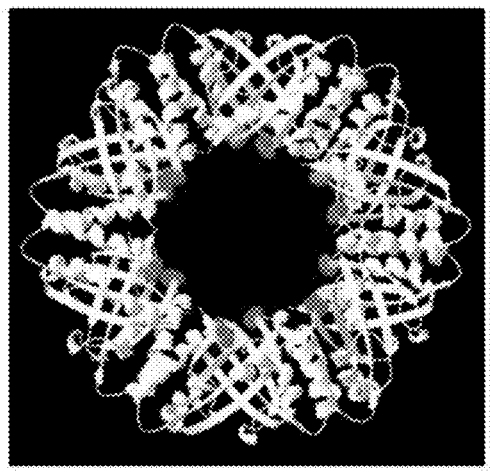 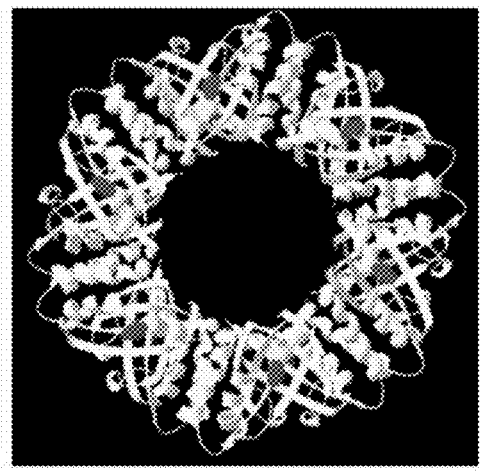
FIG. 1A            FIG. 1B
FIG. 2A
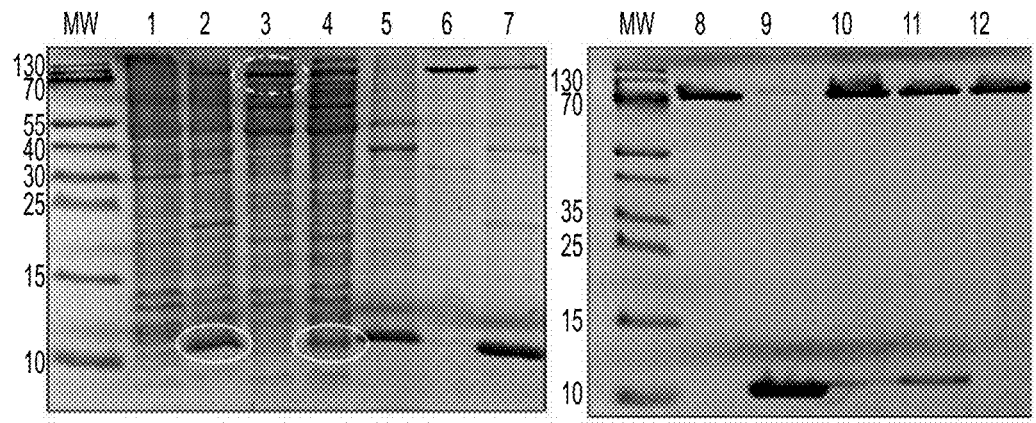
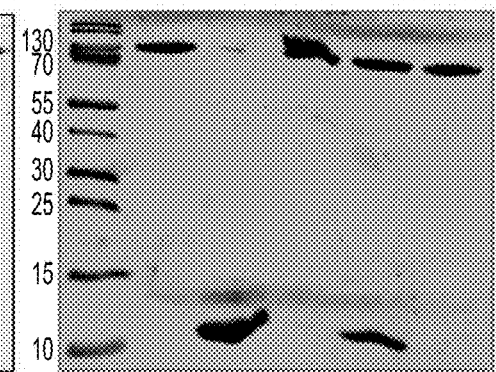
FIG. 2B

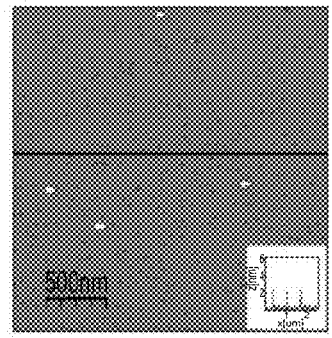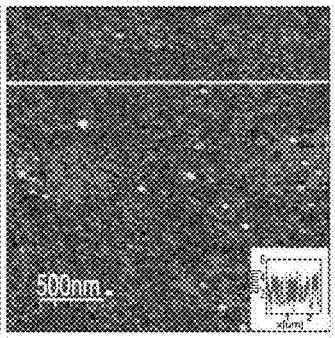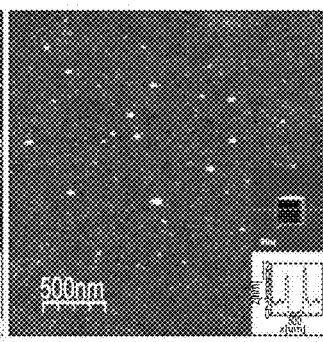
FIG. 3A    FIG. 3B    FIG. 3C
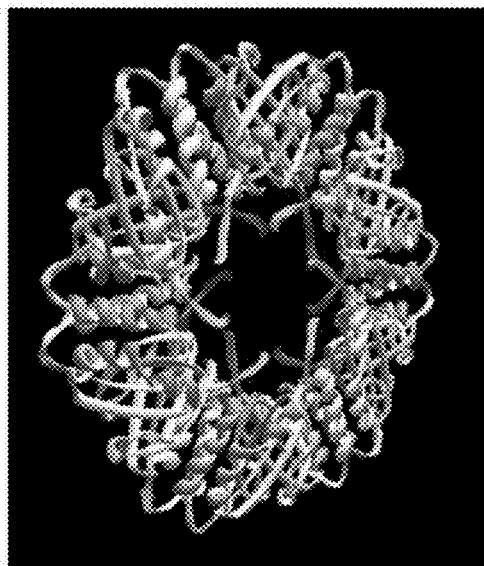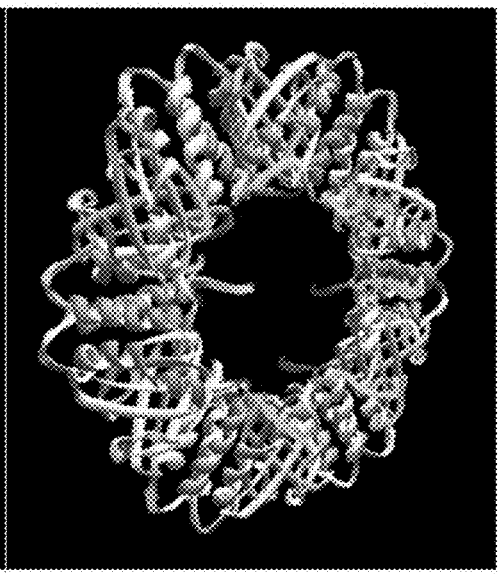
FIG. 4A    FIG. 4B

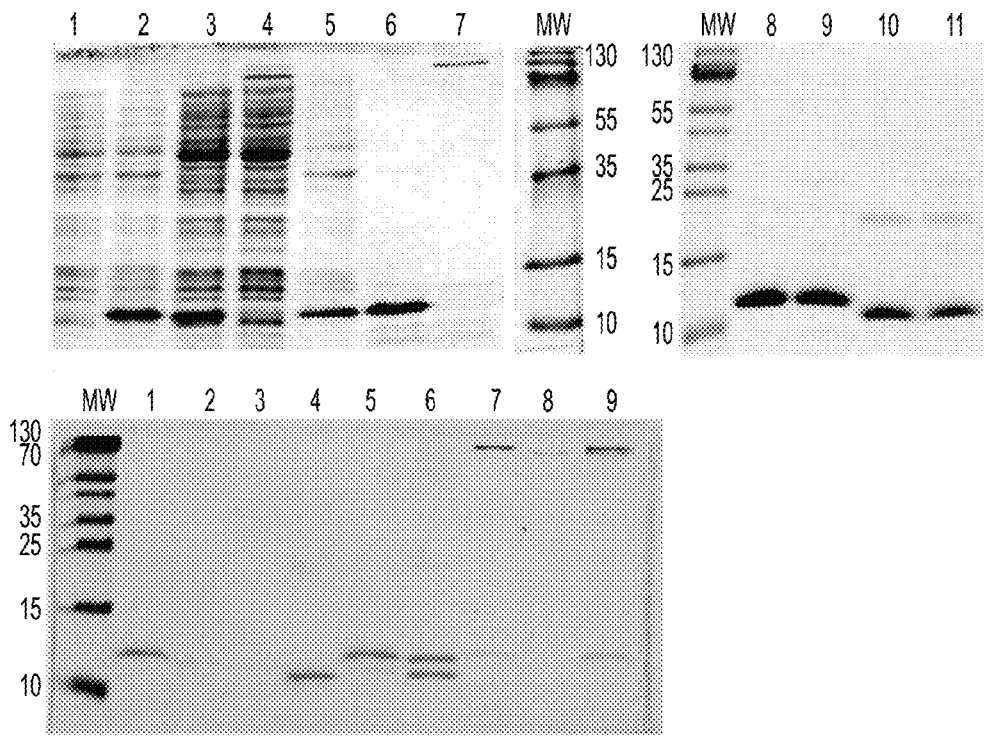
FIG. 5A
FIG. 5B
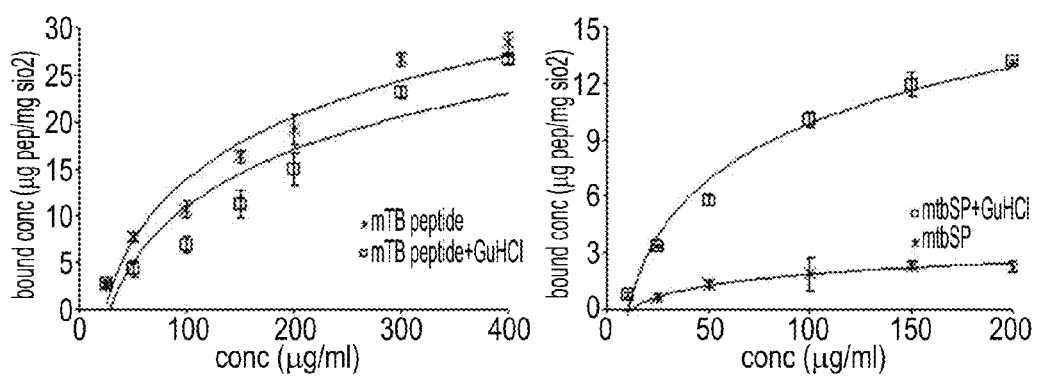
FIG. 6A
FIG. 6B

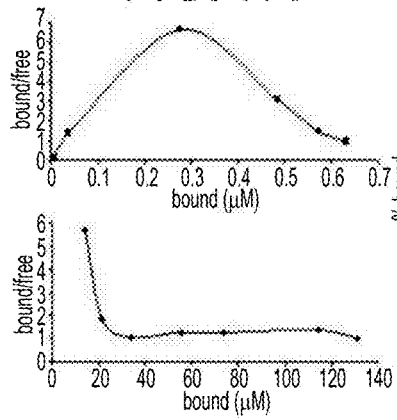
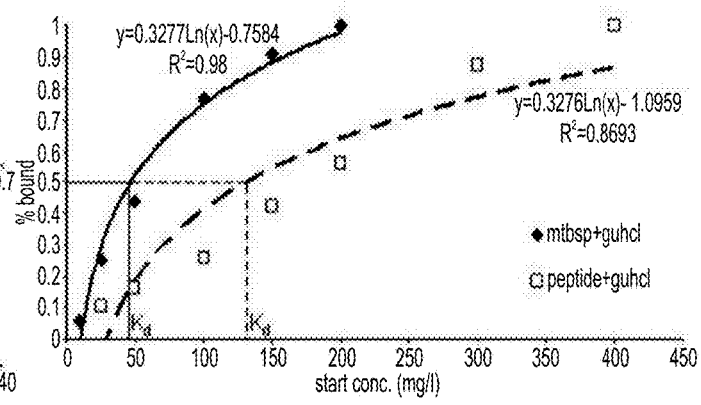
FIG. 7A
FIG. 7B
FIG. 7C
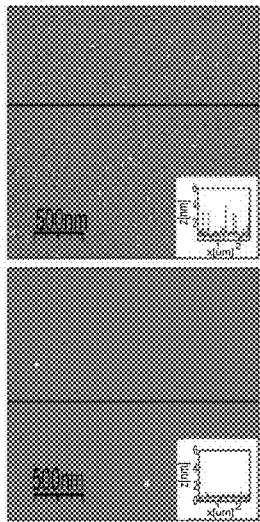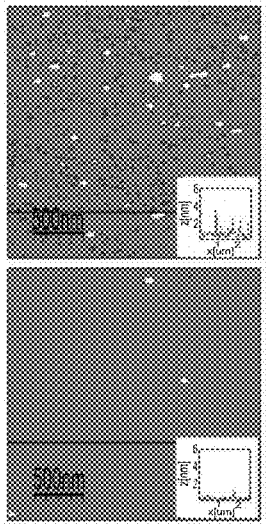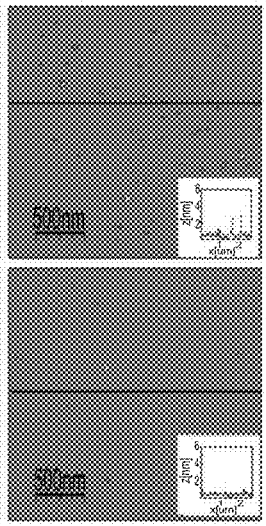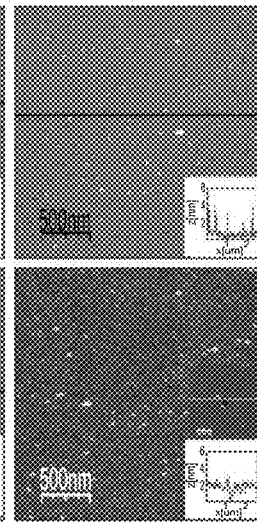
FIG. 8A    FIG. 8B    FIG. 8C    FIG. 8D
FIG. 8E    FIG. 8F    FIG. 8G    FIG. 8H FIGs. 10A-B : SP1 and SP1–CNT binds to Kevlar fiber FIGs 11A-C: An high resolution scanning electron microscopy image of MWCNT bound aramid fabric FIG. 12B : SP1/CNT standard curve:
transmittance of SP1/CNT solution at 600 nm
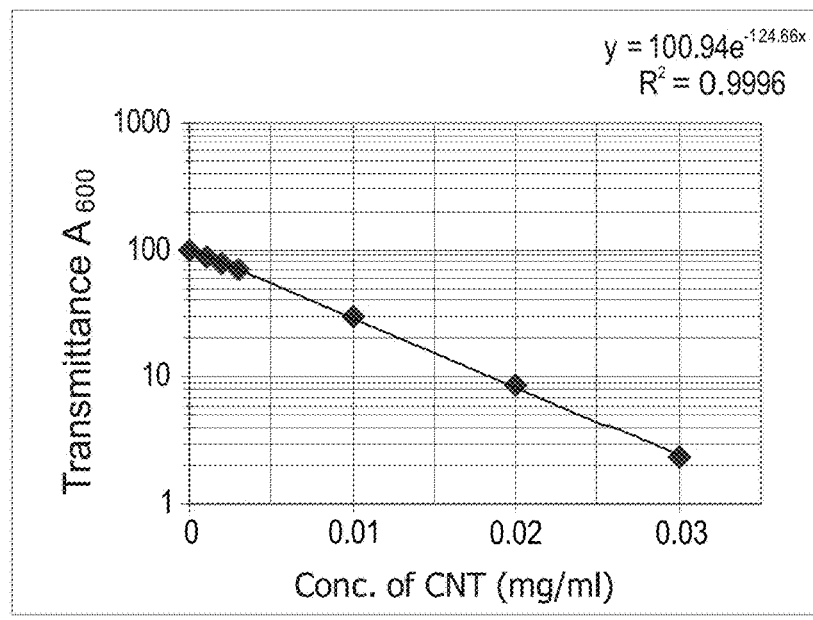
FIG. 12C : SP1/CNT binding to carbon fiber as determined by increased in CNT transmittance at 600 nm over time of sonication

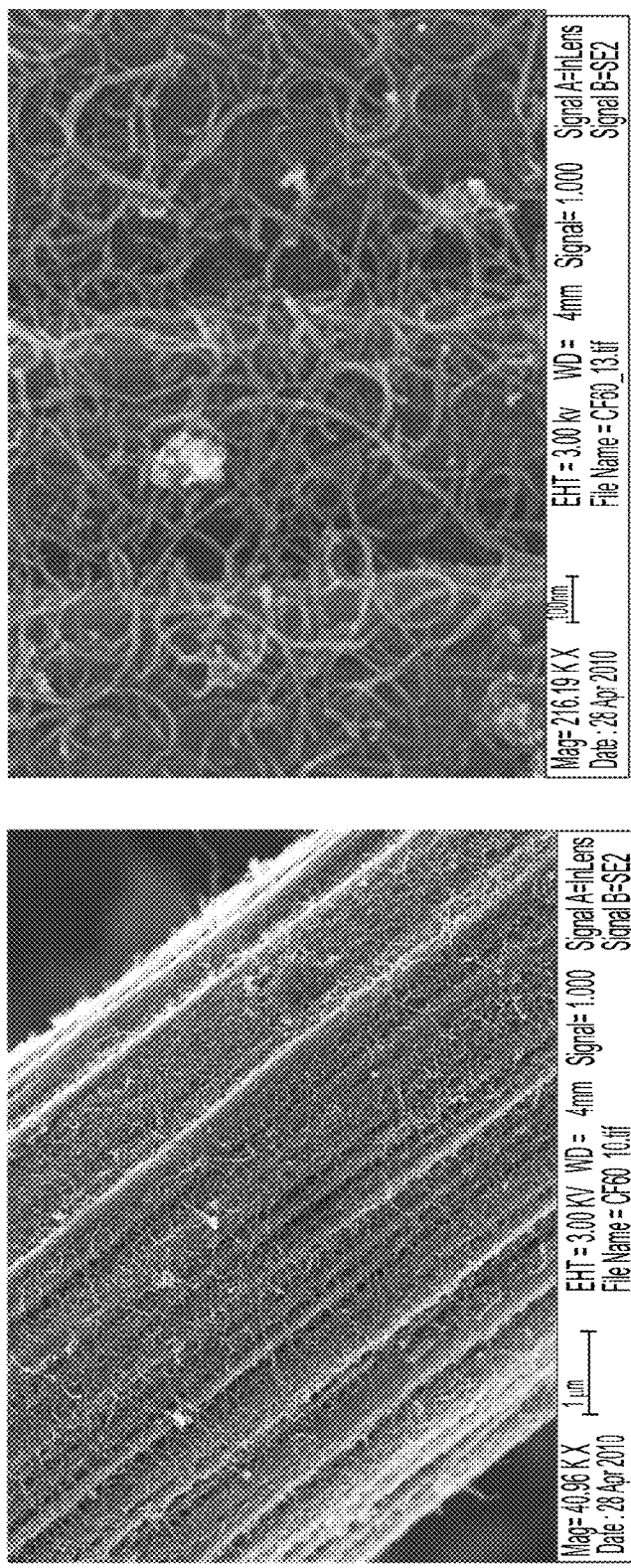
FIGS. 13A-B: An high resolution scanning electron microscopy image of MWCNT bound carbon fabric

SEQUENCE LISTING

```
<160> NUMBER OF SEQ ID NOS: 89

<210> SEQ ID NO 1
<211> LENGTH: 103
<212> TYPE: PRT
<213> ORGANISM: Artificial sequence
<220> FEATURE:
<223> OTHER INFORMATION: Sp1 mutant variant: amino acid 2-6 deleted,
      M43C mutated

<400> SEQUENCE: 1

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

Asp Leu Ile Pro Ser Cys Lys Ser Phe Asn Trp Gly Thr Asp Leu Gly
        35                  40                  45

Met Glu Ser Ala Glu Leu Asn Arg Gly Tyr Thr His Ala Phe Glu Ser
    50                  55                  60

Thr Phe Glu Ser Lys Ser Gly Leu Gln Glu Tyr Leu Asp Ser Ala Ala
```

65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 2
<211> LENGTH: 103
<212> TYPE: PRT
<213> ORGANISM: Artificial sequence
<220> FEATURE:
<223> OTHER INFORMATION: Sp1 mutant variant: amino acid 2-6 deleted,
      L81C mutated

<400> SEQUENCE: 2

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
                20                  25                  30

Asp Leu Ile Pro Ser Met Lys Ser Phe Asn Trp Gly Thr Asp Leu Gly
            35                  40                  45

Met Glu Ser Ala Glu Leu Asn Arg Gly Tyr Thr His Ala Phe Glu Ser
        50                  55                  60

Thr Phe Glu Ser Lys Ser Gly Leu Gln Glu Tyr Cys Asp Ser Ala Ala
65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 3
<211> LENGTH: 114
<212> TYPE: PRT
<213> ORGANISM: Artificial sequence
<220> FEATURE:
<223> OTHER INFORMATION: mTB peptide fused to N' of Sp1 (2-6 deleted
      and M43C mutated)

<400> SEQUENCE: 3

Met Arg Lys Leu Pro Asp Ala Ala Thr Arg Thr Pro Lys Leu Val Lys
1               5                   10                  15

His Thr Leu Leu Thr Arg Phe Lys Asp Glu Ile Thr Arg Glu Gln Ile
                20                  25                  30

Asp Asn Tyr Ile Asn Asp Tyr Thr Asn Leu Leu Asp Leu Ile Pro Ser
            35                  40                  45

Met Lys Ser Phe Asn Trp Gly Thr Asp Leu Gly Met Glu Ser Ala Glu
        50                  55                  60

Leu Asn Arg Gly Tyr Thr His Ala Phe Glu Ser Thr Phe Glu Ser Lys
65                  70                  75                  80

Ser Gly Leu Gln Glu Tyr Leu Asp Ser Ala Ala Leu Ala Ala Phe Ala
                85                  90                  95

Glu Gly Phe Leu Pro Thr Leu Ser Gln Arg Leu Val Ile Asp Tyr Phe
            100                 105                 110

Leu Tyr

<210> SEQ ID NO 4
<211> LENGTH: 108
<212> TYPE: PRT
<213> ORGANISM: Populus tremula

```
<220> FEATURE:
<221> NAME/KEY: misc_feature
<223> OTHER INFORMATION: Wild type Sp1 polypeptide

<400> SEQUENCE: 4

Met Ala Thr Arg Thr Pro Lys Leu Val Lys His Thr Leu Leu Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105

<210> SEQ ID NO 5
<211> LENGTH: 6
<212> TYPE: PRT
<213> ORGANISM: Artificial sequence
<220> FEATURE:
<223> OTHER INFORMATION: mTBP peptide

<400> SEQUENCE: 5

Arg Lys Leu Pro Asp Ala
1               5

<210> SEQ ID NO 6
<211> LENGTH: 120
<212> TYPE: PRT
<213> ORGANISM: Artificial sequence
<220> FEATURE:
<223> OTHER INFORMATION: L1-Sp1 fusion polypeptide

<400> SEQUENCE: 6

Met His Trp Ser Ala Trp Trp Ile Arg Ser Asn Gln Ser Ala Thr Arg
1               5                   10                  15

Thr Pro Lys Leu Val Lys His Thr Leu Leu Thr Arg Phe Lys Asp Glu
            20                  25                  30

Ile Thr Arg Glu Gln Ile Asp Asn Tyr Ile Asn Asp Tyr Thr Asn Leu
        35                  40                  45

Leu Asp Leu Ile Pro Ser Met Lys Ser Phe Asn Trp Gly Thr Asp Leu
    50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
        115                 120

<210> SEQ ID NO 7
<211> LENGTH: 333
<212> TYPE: DNA
<213> ORGANISM: Artificial sequence
```

```
<220> FEATURE:
<223> OTHER INFORMATION: Delta N' SP1 coding sequence

<400> SEQUENCE: 7
ccacagagag aaagggaaga catgaagctt gtgaagcaca cattgttgac tcggttcaag      60
gatgagatca cacgagaaca gatcgacaac tacattaatg actataccaa tctgctcgat     120
ctcattccaa gcatgaagag tttcaattgg ggcacggatc tgggcatgga gtctgcggag     180
ctaaaccgag atacactca tgcctttgaa tctacatttg agagcaagtc tggtttgcaa      240
gagtacctcg attctgctgc tcttgctgca tttgcagaag ggttttttgcc tactttgtca    300 cagcgtcttg tgatagacta ctttctctac taa                                  333

<210> SEQ ID NO 8
<211> LENGTH: 120
<212> TYPE: PRT
<213> ORGANISM: Artificial sequence
<220> FEATURE:
<223> OTHER INFORMATION: L3-Sp1 fusion polypeptide

<400> SEQUENCE: 8

Met Asp Tyr Phe Ser Ser Pro Tyr Tyr Glu Gln Leu Phe Ala Thr Arg
1               5                   10                  15

Thr Pro Lys Leu Val Lys His Thr Leu Leu Thr Arg Phe Lys Asp Glu
                20                  25                  30

Ile Thr Arg Glu Gln Ile Asp Asn Tyr Ile Asn Asp Tyr Thr Asn Leu
            35                  40                  45

Leu Asp Leu Ile Pro Ser Met Lys Ser Phe Asn Trp Gly Thr Asp Leu
        50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
        115                 120

<210> SEQ ID NO 9
<211> LENGTH: 120
<212> TYPE: PRT
<213> ORGANISM: Artificial sequence
<220> FEATURE:
<223> OTHER INFORMATION: L4-Sp1 fusion polypeptide

<400> SEQUENCE: 9

Met His Trp Ser Ala Trp Trp Ile Arg Ser Asn Gln Ser Ala Thr Arg
1               5                   10                  15

Thr Pro Lys Leu Val Lys His Thr Leu Leu Thr Arg Phe Lys Asp Glu
                20                  25                  30

Ile Thr Lys Glu Gln Ile Asp Asn Tyr Ile Asn Asp Tyr Thr Asn Leu
            35                  40                  45

Leu Asp Leu Ile Pro Ser Met Lys Ser Phe Asn Trp Gly Thr Asp Leu
        50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95
```

```
Ala Leu Ala Ala Phe Ala Glu Gly Phe Leu Pro Thr Leu Ser Gln Arg
                100                 105                 110

Leu Val Ile Asp Tyr Phe Leu Tyr
        115                 120

<210> SEQ ID NO 10
<211> LENGTH: 12
<212> TYPE: PRT
<213> ORGANISM: Artificial sequence
<220> FEATURE:
<223> OTHER INFORMATION: L1 peptide

<400> SEQUENCE: 10

His Trp Ser Ala Trp Trp Ile Arg Ser Asn Gln Ser
1               5                   10

<210> SEQ ID NO 11
<211> LENGTH: 12
<212> TYPE: PRT
<213> ORGANISM: Artificial sequence
<220> FEATURE:
<223> OTHER INFORMATION: L2 peptide

<400> SEQUENCE: 11

His Ser Ser Tyr Trp Tyr Ala Phe Asn Asn Lys Thr
1               5                   10

<210> SEQ ID NO 12
<211> LENGTH: 12
<212> TYPE: PRT
<213> ORGANISM: Artificial sequence
<220> FEATURE:
<223> OTHER INFORMATION: L3 peptide

<400> SEQUENCE: 12

Asp Tyr Phe Ser Ser Pro Tyr Tyr Glu Gln Leu Phe
1               5                   10

<210> SEQ ID NO 13
<211> LENGTH: 4
<212> TYPE: PRT
<213> ORGANISM: Artificial sequence
<220> FEATURE:
<223> OTHER INFORMATION: L6 peptide

<400> SEQUENCE: 13

Ser Asn Gln Ser
1

<210> SEQ ID NO 14
<211> LENGTH: 120
<212> TYPE: PRT
<213> ORGANISM: Artificial sequence
<220> FEATURE:
<223> OTHER INFORMATION: L2-Sp1 fusion polypeptde

<400> SEQUENCE: 14

Met His Ser Ser Tyr Trp Tyr Ala Phe Asn Asn Lys Thr Ala Thr Arg
1               5                   10                  15

Thr Pro Lys Leu Val Lys His Thr Leu Leu Thr Arg Phe Lys Asp Glu
            20                  25                  30

Ile Thr Arg Glu Gln Ile Asp Asn Tyr Ile Asn Asp Tyr Thr Asn Leu
        35                  40                  45

Leu Asp Leu Ile Pro Ser Met Lys Ser Phe Asn Trp Gly Thr Asp Leu
    50                  55                  60
```

```
Gly Met Glu Ser Ala Glu Leu Asn Arg Gly Tyr Thr His Ala Phe Glu
 65                  70                  75                  80

Ser Thr Phe Glu Ser Lys Ser Gly Leu Gln Glu Tyr Leu Asp Ser Ala
             85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
        115                 120

<210> SEQ ID NO 15
<211> LENGTH: 112
<212> TYPE: PRT
<213> ORGANISM: Artificial sequence
<220> FEATURE:
<223> OTHER INFORMATION: L6-Sp1 fusion polypeptide

<400> SEQUENCE: 15

Met Ser Asn Gln Ser Ala Thr Arg Thr Pro Lys Leu Val Lys His Thr
  1               5                  10                  15

Leu Leu Thr Arg Phe Lys Asp Glu Ile Thr Arg Glu Gln Ile Asp Asn
             20                  25                  30

Tyr Ile Asn Asp Tyr Thr Asn Leu Leu Asp Leu Ile Pro Ser Met Lys
         35                  40                  45

Ser Phe Asn Trp Gly Thr Asp Leu Gly Met Glu Ser Ala Glu Leu Asn
 50                  55                  60

Arg Gly Tyr Thr His Ala Phe Glu Ser Thr Phe Glu Ser Lys Ser Gly
 65                  70                  75                  80

Leu Gln Glu Tyr Leu Asp Ser Ala Ala Leu Ala Ala Phe Ala Glu Gly
             85                  90                  95

Phe Leu Pro Thr Leu Ser Gln Arg Leu Val Ile Asp Tyr Phe Leu Tyr
            100                 105                 110

<210> SEQ ID NO 16
<211> LENGTH: 120
<212> TYPE: PRT
<213> ORGANISM: Artificial sequence
<220> FEATURE:
<223> OTHER INFORMATION: L7-Sp1 fusion polypeptide

<400> SEQUENCE: 16

Met His Trp Ser Ala Trp Trp Ile Arg Ser Asn Gln Ser Ala Thr Arg
  1               5                  10                  15

Thr Pro Lys Leu Val Lys His Thr Leu Leu Thr Arg Phe Lys Asp Glu
             20                  25                  30

Ile Thr Arg Glu Gln Ile Asp Asn Tyr Ile Asn Asp Tyr Thr Asn Leu
             35                  40                  45

Leu Asp Leu Ile Pro Ser Met Lys Ser Phe Asn Trp Gly Thr Asp Leu
 50                  55                  60

Gly Met Glu Ser Ala Glu Leu Asn Arg Gly Tyr Thr His Ala Phe Glu
 65                  70                  75                  80

Ser Thr Phe Glu Ser Lys Ser Gly Leu Gln Glu Tyr Leu Asp Ser Ala
             85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
        115                 120
```

```
<210> SEQ ID NO 17
<211> LENGTH: 120
<212> TYPE: PRT
<213> ORGANISM: Artificial sequence
<220> FEATURE:
<223> OTHER INFORMATION: L5-Sp1 fusion polypeptide

<400> SEQUENCE: 17

Met His Trp Ser Ala Trp Trp Ile Arg Ser Asn Gln Ser Ala Thr Arg
1               5                   10                  15

Thr Pro Lys Leu Val Lys His Thr Leu Leu Thr Arg Phe Lys Asp Glu
            20                  25                  30

Ile Cys Arg Glu Gln Ile Asp Asn Tyr Ile Asn Asp Tyr Thr Asn Leu
        35                  40                  45

Leu Asp Leu Ile Pro Ser Met Lys Ser Phe Asn Trp Gly Thr Asp Leu
    50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
        115                 120

<210> SEQ ID NO 18
<211> LENGTH: 120
<212> TYPE: PRT
<213> ORGANISM: Artificial sequence
<220> FEATURE:
<223> OTHER INFORMATION: L8-Sp1 fusion polypeptide

<400> SEQUENCE: 18

Met His Trp Ser Ala Trp Trp Ile Arg Ser Asn Gln Ser Ala Thr Arg
1               5                   10                  15

Thr Pro Lys Leu Val Lys His Thr Leu Leu Thr Arg Phe Lys Asp Glu
            20                  25                  30

Ile Thr Lys Glu Gln Ile Asp Asn Tyr Ile Asn Asp Tyr Thr Asn Leu
        35                  40                  45

Leu Asp Leu Ile Pro Ser Met Lys Ser Phe Asn Trp Gly Thr Asp Leu
    50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
        115                 120

<210> SEQ ID NO 19
<211> LENGTH: 6
<212> TYPE: PRT
<213> ORGANISM: Artificial sequence
<220> FEATURE:
<223> OTHER INFORMATION: Exemplary heterologous titanium binding peptide

<400> SEQUENCE: 19

Arg Ala Leu Pro Asp Ala
1               5
```

```
<210> SEQ ID NO 20
<211> LENGTH: 10
<212> TYPE: PRT
<213> ORGANISM: Artificial sequence
<220> FEATURE:
<223> OTHER INFORMATION: Exemplary peptide that binds inorganic
      substances

<400> SEQUENCE: 20

Ala Lys Pro Ser Tyr Pro Pro Thr Tyr Lys
1               5                   10

<210> SEQ ID NO 21
<211> LENGTH: 6
<212> TYPE: PRT
<213> ORGANISM: Artificial sequence
<220> FEATURE:
<223> OTHER INFORMATION: Exemplary peptide that binds inorganic
      substances

<400> SEQUENCE: 21

Ala Lys Pro Thr Tyr Lys
1               5

<210> SEQ ID NO 22
<211> LENGTH: 10
<212> TYPE: PRT
<213> ORGANISM: Artificial sequence
<220> FEATURE:
<223> OTHER INFORMATION: Exemplary peptide that binds inorganic
      substances

<400> SEQUENCE: 22

Pro Lys Ile Ser Tyr Pro Pro Thr Tyr Lys
1               5                   10

<210> SEQ ID NO 23
<211> LENGTH: 10
<212> TYPE: PRT
<213> ORGANISM: Artificial sequence
<220> FEATURE:
<223> OTHER INFORMATION: Exemplary peptide that binds inorganic
      substances
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 23

Ala Pro Pro Pro Ala Xaa Thr Ala Xaa Lys
1               5                   10

<210> SEQ ID NO 24
<211> LENGTH: 10
<212> TYPE: PRT
<213> ORGANISM: Artificial sequence
<220> FEATURE:
<223> OTHER INFORMATION: Exemplary peptide that binds inorganic
      substances
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
```

```
<222> LOCATION: (9)..(9)
<223> OTHER INFORMATION: Xaa can be any naturally occurring amino acid

<400> SEQUENCE: 24

Ala Thr Pro Lys Pro Xaa Thr Ala Xaa Lys
1               5                   10

<210> SEQ ID NO 25
<211> LENGTH: 4
<212> TYPE: PRT
<213> ORGANISM: Artificial sequence
<220> FEATURE:
<223> OTHER INFORMATION: Exemplary peptide that binds inorganic
      substances

<400> SEQUENCE: 25

Pro Tyr Val Lys
1

<210> SEQ ID NO 26
<211> LENGTH: 12
<212> TYPE: PRT
<213> ORGANISM: Artificial sequence
<220> FEATURE:
<223> OTHER INFORMATION: Exemplary peptide that binds inorganic
      substances

<400> SEQUENCE: 26

Ala Lys Pro Ser Pro Tyr Val Pro Thr Gly Tyr Lys
1               5                   10

<210> SEQ ID NO 27
<211> LENGTH: 13
<212> TYPE: PRT
<213> ORGANISM: Artificial sequence
<220> FEATURE:
<223> OTHER INFORMATION: Exemplary peptide that binds inorganic
      substances

<400> SEQUENCE: 27

Gly Gln Gln Lys Gln Thr Ala Tyr Asp Pro Gly Tyr Lys
1               5                   10

<210> SEQ ID NO 28
<211> LENGTH: 567
<212> TYPE: DNA
<213> ORGANISM: Populus tremula

<400> SEQUENCE: 28
atccacagag agaaagggaa gacatggcaa ccagaactcc aaagcttgtg aagcacacat      60
tgttgactcg gttcaaggat gagatcacac gagaacagat cgacaactac attaatgact    120
ataccaatct gctcgatctc attccaagca tgaagagttt caattggggc acggatctgg    180
gcatggagtc tgcggagcta aaccgaggat acactcatgc ctttgaatct acatttgaga    240
gcaagtctgg tttgcaagag tacctcgatt ctgctgctct gctgcatttt gcagaagggt    300
ttttgcctac tttgtcacag cgtcttgtga tagactactt tctctactaa acgctcagga    360
gtaacgactt cggccgggct atttcatggt aataaagtaa tgtaatgttc aataaatgct    420
ggttttgaac cactgaatgt tcgtgtcttg atttcttgtc tgtgctaagt gaagggagtg    480
ctgctattcc tttaaaaata aagcccttgg ggttgagttg tagtttttca atcttttcc    540 ccgatttatt tcggtcttgg tgttgtt                                        567
```

```
<210> SEQ ID NO 29
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 29

Val Val Lys His Leu Val Ile Val Gln Phe Lys Glu Asp Val Thr Pro
1               5                   10                  15

Glu Arg Leu Asp Gly Leu Ile Arg Gly Tyr Ala Gly Leu Val Asp Lys
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
                85                  90                  95

Asp Phe

<210> SEQ ID NO 30
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 30

Val Val Lys His Leu Val Ile Val Gln Phe Lys Glu Asp Val Thr Pro
1               5                   10                  15

Glu Arg Leu Asp Gly Leu Ile Arg Gly Tyr Ala Gly Leu Val Asp Lys
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
                85                  90                  95

Asp Phe

<210> SEQ ID NO 31
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 31

Val Val Lys His Leu Val Ile Val Gln Phe Lys Glu Asp Val Thr Pro
1               5                   10                  15

Glu Arg Leu Glu Gly Leu Ile Arg Gly Tyr Ala Gly Leu Val Asp Lys
```

```
                    20                  25                  30
Val Pro Ser Met Lys Ala Phe His Trp Gly Thr Asp Val Ser Ile Glu
            35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Val Tyr His Pro Ala His Val
 65                 70                  75                  80

Glu Phe Ala Thr Asp Phe Leu Gly Ser Thr Glu Lys Val Leu Ile Ile
                85                  90                  95

Asp Phe

<210> SEQ ID NO 32
<211> LENGTH: 84
<212> TYPE: PRT
<213> ORGANISM: Zea mays
<220> FEATURE:
<221> NAME/KEY: misc_feature
<222> LOCATION: (50)..(51)
<223> OTHER INFORMATION: Xaa can be any naturally occurring amino acid

<400> SEQUENCE: 32

Val Val Lys His Ile Leu Leu Ala Ser Phe Lys Glu Glu Val Thr Gln
 1               5                  10                  15

Glu Arg Leu Asp Glu Leu Ile Arg Gly Tyr Ala Ala Leu Val Gly Val
                20                  25                  30

Val Pro Ser Met Lys Ala Phe His Trp Gly Thr Asp Val Ser Ile Glu
            35                  40                  45

Asn Xaa Xaa Met His Gln Gly Phe Thr His Val Phe Glu Ser Thr Phe
    50                  55                  60

Glu Ser Thr Glu Gly Ile Lys Glu Tyr Ile Glu His Pro Ala His Val
 65                 70                  75                  80

Glu Phe Ala Lys

<210> SEQ ID NO 33
<211> LENGTH: 98
<212> TYPE: PRT
<213> ORGANISM: Oryza sativa
<220> FEATURE:
<221> NAME/KEY: misc_feature
<222> LOCATION: (50)..(51)
<223> OTHER INFORMATION: Xaa can be any naturally occurring amino acid

<400> SEQUENCE: 33

Val Val Lys His Ile Leu Leu Ala Arg Phe Lys Glu Asp Val Ala Pro
 1               5                  10                  15

Glu Arg Leu Asp Gln Leu Ile Arg Gly Tyr Ala Gly Leu Val Asp Leu
                20                  25                  30

Val Pro Ser Met Lys Ala Phe His Trp Gly Thr Asp Val Ser Ile Glu
            35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Ile Glu His Pro Ala His Val
 65                 70                  75                  80

Glu Phe Ala Asn Glu Phe Leu Pro Val Leu Glu Lys Thr Leu Ile Ile
                85                  90                  95

Asp Tyr

<210> SEQ ID NO 34
```

```
<211> LENGTH: 98
<212> TYPE: PRT
<213> ORGANISM: Triticum aestivum
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (48)..(49)
<223> OTHER INFORMATION: Xaa can be any naturally occurring amino acid

<400> SEQUENCE: 34

Val Val Lys His Leu Val Leu Ala Arg Phe Lys Glu Glu Ala Thr Pro
1               5                   10                  15

Glu Ala Leu Asp Xaa Leu Ile Arg Arg Tyr Ala Gly Leu Val Asp Ala
            20                  25                  30

Val Pro Ser Met Lys Ala Phe His Trp Gly Thr Asp Val Thr Val Xaa
        35                  40                  45

Xaa Leu Asp Thr His Glu Gly Phe Thr His Val Phe Glu Ser Thr Phe
    50                  55                  60

Glu Ser Ala Glu Gly Val Lys Glu Tyr Ile Ala His Pro Ser His Val
65                  70                  75                  80

Glu Phe Val Asp Glu Phe Leu Ala Leu Ala Glu Lys Met Leu Ile Val
                85                  90                  95

Asp Tyr

<210> SEQ ID NO 35
<211> LENGTH: 109
<212> TYPE: PRT
<213> ORGANISM: Arabidopsis thaliana

<400> SEQUENCE: 35

Met Glu Glu Ala Lys Gly Pro Val Lys His Val Leu Leu Ala Ser Phe
1               5                   10                  15

Lys Asp Gly Val Ser Pro Glu Lys Ile Glu Glu Leu Ile Lys Gly Tyr
            20                  25                  30

Ala Asn Leu Val Asn Leu Ile Glu Pro Met Lys Ala Phe His Trp Gly
        35                  40                  45

Lys Asp Val Ser Ile Glu Asn Leu His Gln Gly Tyr Thr His Ile Phe
    50                  55                  60

Glu Ser Thr Phe Glu Ser Lys Glu Ala Val Ala Glu Tyr Ile Ala His
65                  70                  75                  80

Pro Ala His Val Glu Phe Ala Thr Ile Phe Leu Gly Ser Leu Asp Lys
                85                  90                  95

Val Leu Val Ile Asp Tyr Lys Pro Thr Ser Val Ser Leu
            100                 105

<210> SEQ ID NO 36
<211> LENGTH: 47
<212> TYPE: PRT
<213> ORGANISM: Arabidopsis thaliana

<400> SEQUENCE: 36

Leu His Gln Gly Tyr Thr His Ile Leu Glu Ser Thr Phe Glu Ser Lys
1               5                   10                  15

Glu Ala Val Ala Glu Tyr Ile Ala His Pro Ala His Val Glu Phe Ala
            20                  25                  30

Thr Ile Phe Leu Gly Ser Leu Asp Lys Val Leu Val Ile Asp Tyr
        35                  40                  45
```

<210> SEQ ID NO 37
<211> LENGTH: 98
<212> TYPE: PRT
<213> ORGANISM: Glycine max
<220> FEATURE:
<221> NAME/KEY: misc_feature
<222> LOCATION: (50)..(51)
<223> OTHER INFORMATION: Xaa can be any naturally occurring amino acid

<400> SEQUENCE: 37

Val Val Lys His Val Leu Leu Ala Lys Phe Lys Asp Asp Val Thr Pro
1               5                   10                  15

Glu Arg Ile Glu Glu Leu Ile Lys Asp Tyr Ala Asn Leu Val Asn Leu
            20                  25                  30

Ile Pro Pro Met Lys Ser Phe His Trp Gly Lys Asp Val Ser Ala Glu
        35                  40                  45

Asn Xaa Xaa Leu His Gln Gly Phe Thr His Val Phe Glu Ser Thr Phe
    50                  55                  60

Glu Ser Pro Glu Gly Val Ala Glu Tyr Val Ala His Pro Ala His Val
65                  70                  75                  80

Glu Tyr Ala Asn Leu Phe Leu Ser Cys Leu Glu Lys Val Ile Val Ile
                85                  90                  95

Asp Tyr

<210> SEQ ID NO 38
<211> LENGTH: 98
<212> TYPE: PRT
<213> ORGANISM: Lycopersicon esculentum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 38

Val Val Lys His Ile Leu Leu Ala Lys Phe Lys Asp Gly Ile Pro Pro
1               5                   10                  15

Glu Gln Ile Asp Gln Leu Ile Lys Gln Tyr Ala Asn Leu Val Asn Leu
            20                  25                  30

Val Glu Pro Met Lys Ala Phe Gln Trp Gly Lys Asp Val Ser Ile Glu
        35                  40                  45

Asn Xaa Xaa Leu His Gln Gly Phe Thr His Val Phe Glu Ser Thr Phe
    50                  55                  60

Asp Ser Leu Glu Gly Val Ala Glu Tyr Ile Ala His Pro Val His Val
65                  70                  75                  80

Glu Tyr Ala Asn Thr Leu Leu Pro Gln Leu Glu Lys Phe Leu Ile Val
                85                  90                  95

Asp Tyr

<210> SEQ ID NO 39
<211> LENGTH: 93
<212> TYPE: PRT
<213> ORGANISM: Glycine max
<220> FEATURE:
<221> NAME/KEY: misc_feature
<222> LOCATION: (49)..(50)
<223> OTHER INFORMATION: Xaa can be any naturally occurring amino acid

<400> SEQUENCE: 39

His Val Leu Leu Pro Lys Leu Lys Asp Tyr Phe Thr Pro Glu Arg Ile
1               5                   10                  15

```
Glu Leu Met Val Asp Tyr Ala Asn Leu Val Asn Leu Met Pro Arg Met
            20                  25                  30

Lys Ser Phe His Ser Gly Arg Asp Val Ser Ala Glu Tyr Leu His Leu
        35                  40                  45

Xaa Xaa Gly Cys Thr His Val Tyr Glu Ser Thr Phe Asp Ser Pro Gly
50                      55                  60

Val Ala Glu Tyr Val Ala His Ala Ala His Val Glu Tyr Ala Asn Gln
65                  70                  75                  80

Asp Leu Ser Cys Leu Glu Lys Val Ile Ala Ile Asp Tyr
                85                  90
```

<210> SEQ ID NO 40
<211> LENGTH: 108
<212> TYPE: PRT
<213> ORGANISM: Populus tremula x Populus tremuloides

<400> SEQUENCE: 40

```
Met Ala Thr Arg Thr Pro Lys Leu Val Lys His Thr Leu Ala Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105
```

<210> SEQ ID NO 41
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 41

```
Lys His Leu Cys Leu Val Arg Phe Lys Glu Gly Val Val Val Glu Asp
1               5                   10                  15

Ile Xaa Xaa Xaa Ile Glu Glu Leu Thr Lys Leu Ala Ala Glu Leu Asp
            20                  25                  30

Thr Val Lys Phe Phe Gly Trp Gly Lys Asp Val Leu Asn Gln Glu Ala
        35                  40                  45

Xaa Leu Thr Gln Gly Phe Thr His Val Phe Ser Met Ser Phe Ala Ser
    50                  55                  60

Ala Glu Asp Leu Ala Ala Tyr Met Gly His Glu Lys His Ser Ala Phe
65                  70                  75                  80

Ala Ala Thr Phe Met Ala Val Leu Asp Lys Val Val Leu Asp Phe
                85                  90                  95
```

```
<210> SEQ ID NO 42
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 42

Lys His Leu Cys Leu Val Arg Phe Lys Glu Gly Val Val Val Glu Asp
1               5                   10                  15

Ile Xaa Xaa Xaa Ile Glu Glu Leu Thr Lys Leu Ala Ala Glu Leu Asp
                20                  25                  30

Thr Val Lys Phe Phe Gly Trp Gly Lys Asp Val Leu Asn Gln Glu Ala
            35                  40                  45

Xaa Leu Thr Gln Gly Phe Thr His Val Phe Ser Met Ser Phe Ala Ser
        50                  55                  60

Ala Glu Asp Leu Ala Ala Cys Met Gly His Glu Lys His Ser Ala Phe
65                  70                  75                  80

Ala Ala Thr Phe Met Ala Val Leu Asp Lys Val Val Val Leu Asp Phe
                85                  90                  95

<210> SEQ ID NO 43
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 43

Lys His Leu Cys Met Ala Lys Phe Lys Glu Gly Val Val Val Glu Asp
1               5                   10                  15

Ile Xaa Xaa Xaa Ile Gln Glu Leu Thr Lys Leu Ala Ala Glu Leu Asp
                20                  25                  30

Thr Val Lys Tyr Phe Gly Trp Gly Lys Asp Val Leu Asn Gln Glu Ala
            35                  40                  45

Xaa Leu Thr Gln Gly Phe Thr His Val Phe Val Met Thr Phe Ala Ser
        50                  55                  60

Ala Glu Asp Leu Ala Ala Cys Met Gly His Glu Lys His Thr Ala Phe
65                  70                  75                  80

Ala Ala Thr Phe Met Ala Ala Leu Asp Lys Val Val Val Met Asp Phe
                85                  90                  95

<210> SEQ ID NO 44
<211> LENGTH: 97
<212> TYPE: PRT
<213> ORGANISM: Oryza sativa
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
```

-continued

```
<222> LOCATION: (45)..(45)
<223> OTHER INFORMATION: Xaa can be any naturally occurring amino acid

<400> SEQUENCE: 44

Val Lys His Leu Cys Leu Val Lys Phe Lys Glu Val Leu Xaa Xaa
1               5                   10                  15

Xaa Val Asp Asp Ile Leu Gln Gly Met Thr Lys Leu Val Ser Glu Met
            20                  25                  30

Asp Met Val Lys Ser Phe Glu Trp Gly Lys Asp Val Xaa Leu Asn Gln
        35                  40                  45

Glu Met Leu Thr Gln Gly Phe Thr His Val Phe Ser Leu Thr Phe Ala
    50                  55                  60

Ser Ser Glu Asp Leu Thr Thr Tyr Met Ser His Glu Arg His Gln Glu
65                  70                  75                  80

Phe Ala Gly Thr Phe Met Ala Ala Ile Asp Lys Val Val Val Val Asp
                85                  90                  95

Phe

<210> SEQ ID NO 45
<211> LENGTH: 104
<212> TYPE: PRT
<213> ORGANISM: Sorghum bicolor
<220> FEATURE:
<221> NAME/KEY: misc_feature
<222> LOCATION: (40)..(42)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid

<400> SEQUENCE: 45

Arg Arg Pro Thr Met Gly Glu Val Lys His Leu Cys Leu Val Lys Phe
1               5                   10                  15

Lys Glu Gly Val Val Val Glu Asp Val Leu Lys Gly Met Thr Asp Leu
            20                  25                  30

Val Ala Gly Met Asp Met Val Xaa Xaa Xaa Lys Ser Phe Glu Trp Gly
        35                  40                  45

Gln Asp Val Xaa Leu Asn Gln Glu Met Leu Thr Gln Gly Phe Thr His
    50                  55                  60

Val Phe Ser Leu Thr Phe Ala Phe Ala Asp Asp Leu Ala Thr Tyr Met
65                  70                  75                  80

Gly His Asp Arg His Ala Ala Phe Ala Thr Phe Met Ala Ala Leu
                85                  90                  95

Asp Lys Val Val Val Ile Asp Phe
            100

<210> SEQ ID NO 46
<211> LENGTH: 77
<212> TYPE: PRT
<213> ORGANISM: Zea mays
<220> FEATURE:
<221> NAME/KEY: misc_feature
<222> LOCATION: (25)..(25)
<223> OTHER INFORMATION: Xaa can be any naturally occurring amino acid

<400> SEQUENCE: 46

Glu Ser Thr Phe Glu Ser Thr Glu Gly Ile Lys Glu Tyr Ile Glu His
1               5                   10                  15

Pro Ala His Val Glu Phe Ala Lys Xaa Leu Asn Gln Glu Met Leu Thr
            20                  25                  30
```

```
Gln Gly Phe Thr His Val Phe Ser Leu Thr Phe Ala Thr Ala Ala Asp
        35                  40                  45

Leu Ala Ala Tyr Met Ala His Asp Ser His Thr Ala Phe Ala Ala Thr
 50                  55                  60

Phe Met Ala Ala Ile Asp Lys Val Leu Val Asp Phe
 65                  70                  75
```

<210> SEQ ID NO 47
<211> LENGTH: 97
<212> TYPE: PRT
<213> ORGANISM: Lycopersicon esculentum
<220> FEATURE:
<221> NAME/KEY: misc_feature
<222> LOCATION: (32)..(34)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid

<400> SEQUENCE: 47

```
Lys His Leu Val Leu Val Lys Phe Lys Glu Asp Val Val Glu Asp
 1               5                  10                  15

Ile Leu Lys Glu Leu Glu Lys Leu Val Gln Glu Met Asp Ile Val Xaa
                20                  25                  30

Xaa Xaa Lys Ser Phe Val Trp Gly Lys Asp Val Xaa Xaa Glu Ser His
         35                  40                  45

Glu Met Leu Arg Gln Gly Phe Thr His Ala Ile Ile Met Thr Phe Asn
 50                  55                  60

Ser Lys Glu Asp Tyr Gln Thr Phe Ala Asn His Pro Asn His Val Gly
 65                  70                  75                  80

Phe Ser Ala Thr Phe Ala Thr Val Ile Asp Lys Ala Val Leu Leu Asp
                 85                  90                  95

Phe
```

<210> SEQ ID NO 48
<211> LENGTH: 94
<212> TYPE: PRT
<213> ORGANISM: Solanum tuberosum
<220> FEATURE:
<221> NAME/KEY: misc_feature
<222> LOCATION: (29)..(31)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid

<400> SEQUENCE: 48

```
Leu Leu Val Lys Phe Lys Gln Asp Val Val Glu Glu Asp Val Leu Lys
 1               5                  10                  15

Gln Ile Glu Gln Leu Val Asn Glu Ile Asp Leu Ile Xaa Xaa Xaa Lys
                20                  25                  30

Ser Phe Val Trp Gly Lys Asp Thr Xaa Xaa Glu Ser Asn Glu Met Val
         35                  40                  45

Thr Gln Gly Tyr Thr His Ala Met Ile Met Thr Phe Asn Ser Lys Glu
 50                  55                  60

Asp Tyr Glu Ala Cys Val Val Lys Glu Val Xaa Xaa Glu Phe Ser Ala
```

```
                       65                  70                  75                  80

Ile Phe Val Thr Val Val Glu Lys Ile Leu Val Leu Asn Phe
                85                  90

<210> SEQ ID NO 49
<211> LENGTH: 96
<212> TYPE: PRT
<213> ORGANISM: Glycine max
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid

<400> SEQUENCE: 49

His Tyr Val Ile Val Lys Phe Lys Asp Gly Val Ala Xaa Xaa Xaa Val
1               5                   10                  15

Asp Asp Leu Ile Gln Gly Leu Glu Lys Met Val Phe Gly Ile Asp His
                20                  25                  30

Val Lys Ser Phe Glu Trp Gly Lys Asp Ile Xaa Xaa Glu Ser His Asp
            35                  40                  45

Met Leu Arg Gln Gly Phe Thr His Ala Phe Leu Met Thr Phe Asn Gly
        50                  55                  60

Lys Glu Glu Phe Asn Ala Phe Gln Thr His Pro Asn His Leu Glu Phe
65                  70                  75                  80

Ser Gly Val Phe Ser Pro Ala Ile Glu Lys Ile Val Val Leu Asp Phe
                85                  90                  95

<210> SEQ ID NO 50
<211> LENGTH: 96
<212> TYPE: PRT
<213> ORGANISM: Glycine max
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid

<400> SEQUENCE: 50

His Tyr Val Ile Val Lys Phe Lys Asp Gly Val Ala Xaa Xaa Xaa Val
1               5                   10                  15

Asp Glu Leu Ile Gln Gly Leu Glu Lys Met Val Ser Gly Ile Asp His
                20                  25                  30

Val Lys Ser Phe Glu Trp Gly Lys Asp Ile Xaa Xaa Glu Ser His Asp
            35                  40                  45

Met Leu Arg Gln Gly Phe Thr His Val Phe Leu Met Ala Phe Asn Gly
        50                  55                  60

Lys Glu Glu Phe Asn Ala Phe Gln Thr His Pro Asn His Leu Glu Phe
65                  70                  75                  80

Thr Gly Val Phe Ser Pro Ala Ile Glu Lys Ile Val Val Leu Asp Phe
                85                  90                  95

<210> SEQ ID NO 51
<211> LENGTH: 97
<212> TYPE: PRT
<213> ORGANISM: Glycine max
<220> FEATURE:
```

```
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid

<400> SEQUENCE: 51

Lys His Phe Val Ile Val Lys Phe Lys Glu Gly Val Ala Xaa Xaa Xaa
1               5                   10                  15

Val Asp Glu Leu Thr Lys Gly Met Glu Lys Leu Val Thr Glu Ile Gly
            20                  25                  30

Ala Val Lys Ser Phe Glu Trp Gly Gln Asp Ile Xaa Xaa Glu Ser Leu
        35                  40                  45

Asp Val Leu Arg Gln Gly Phe Thr His Ala Phe Leu Met Thr Phe Asn
    50                  55                  60

Lys Lys Glu Asp Phe Val Ala Phe Gln Ser His Pro Asn His Val Glu
65                  70                  75                  80

Phe Ser Thr Lys Phe Ser Ala Ala Ile Glu Asn Ile Val Leu Leu Asp
                85                  90                  95

Phe

<210> SEQ ID NO 52
<211> LENGTH: 43
<212> TYPE: PRT
<213> ORGANISM: Glycine max
<220> FEATURE:
<221> NAME/KEY: misc_feature
<222> LOCATION: (18)..(19)
<223> OTHER INFORMATION: Xaa can be any naturally occurring amino acid

<400> SEQUENCE: 52

Leu Val Ser Glu Ile His Ala Val Lys Ser Phe Glu Trp Gly Gln Asp
1               5                   10                  15

Ile Xaa Xaa Glu Ser Leu Asp Val Leu Arg Gln Gly Phe Thr His Ala
            20                  25                  30

Phe Leu Met Thr Phe Asn Lys Lys Arg Arg Leu
            35                  40

<210> SEQ ID NO 53
<211> LENGTH: 111
<212> TYPE: PRT
<213> ORGANISM: Arabidopsis thaliana

<400> SEQUENCE: 53

Met Ala Thr Ser Gly Phe Lys His Leu Val Val Lys Phe Lys Glu
1               5                   10                  15

Asp Thr Lys Val Asp Glu Ile Leu Lys Gly Leu Glu Asn Leu Val Ser
            20                  25                  30

Gln Ile Asp Thr Val Lys Ser Phe Glu Trp Gly Glu Asp Lys Glu Ser
        35                  40                  45

His Asp Met Leu Arg Gln Gly Phe Thr His Ala Phe Ser Met Thr Phe
    50                  55                  60

Glu Asn Lys Asp Gly Tyr Val Ala Phe Thr Ser His Pro Leu His Val
65                  70                  75                  80

Glu Phe Ser Ala Ala Phe Thr Ala Val Ile Asp Lys Ile Val Leu Leu
                85                  90                  95

Asp Phe Pro Val Ala Ala Val Lys Ser Ser Val Val Ala Thr Pro
                100                 105                 110
```

<210> SEQ ID NO 54
<211> LENGTH: 100
<212> TYPE: PRT
<213> ORGANISM: Glycine max
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid

<400> SEQUENCE: 54

Lys Thr Val Glu His Ile Val Leu Phe Lys Val Lys Glu Glu Thr Glu
1               5                   10                  15

Pro Ser Lys Val Ser Asp Met Val Asn Gly Leu Gly Ser Leu Val Ser
            20                  25                  30

Leu Asp Pro Val Leu His Xaa Leu Ser Val Gly Pro Leu Leu Arg Asn
        35                  40                  45

Arg Ser Ser Ala Leu Thr Xaa Xaa Phe Thr His Met Leu His Ser Arg
    50                  55                  60

Tyr Lys Ser Lys Glu Asp Leu Glu Ala Tyr Ser Ala His Pro Ser His
65                  70                  75                  80

Val Ser Val Val Lys Gly Tyr Val Leu Pro Ile Ile Asp Asp Ile Met
                85                  90                  95

Ser Val Asp Trp
            100

<210> SEQ ID NO 55
<211> LENGTH: 352
<212> TYPE: DNA
<213> ORGANISM: Artificial sequence
<220> FEATURE:
<223> OTHER INFORMATION: mtbSP coding sequence

<400> SEQUENCE: 55
aaaacatatg cgcaaacttc cggatgcggc aaccagaact ccaaagcttg tgaagcacac    60
attgttgact cggttcaagg atgagatcac acgagaacag atcgacaact acattaatga   120
ctataccaat ctgctcgatc tcattccaag catgaagagt ttcaattggg cacggatct    180 gggcatggag tctgcggagc taaaccgagg atacactcat gcctttgaat ctacatttga   240
gagcaagtct ggtttgcaag agtacctcga ttctgctgct cttgctgcat tgcagaagg    300 gttttttgcct actttgtcac agcgtcttgt gatagactac tttctctact aa          352

<210> SEQ ID NO 56
<211> LENGTH: 383
<212> TYPE: DNA
<213> ORGANISM: Artificial sequence
<220> FEATURE:
<223> OTHER INFORMATION: L1-SP1 coding sequence

<400> SEQUENCE: 56
aaggagatat acaaaaacat atgcactggt cagcatggtg gatacgatca aatcaatcag    60
caaccagaac tccaaagctt gtgaagcaca cattgttgac tcggttcaag gatgagatca   120
cacgagaaca gatcgacaac tacattaatg actataccaa tctgctcgat ctcattccaa   180
gcatgaagag tttcaattgg ggcacggatc tgggcatgga gtctgcggag ctaaaccgag    240
gatacactca tgcctttgaa tctacatttg agagcaagtc tggtttgcaa gagtacctcg    300

```
attctgctgc tcttgctgca tttgcagaag ggttttttgcc tactttgtca cagcgtcttg    360
tgatagacta ctttctctac taa                                             383

<210> SEQ ID NO 57
<211> LENGTH: 384
<212> TYPE: DNA
<213> ORGANISM: Artificial sequence
<220> FEATURE:
<223> OTHER INFORMATION: L2-Sp1 coding sequence

<400> SEQUENCE: 57
gaaggagata tacaaaaaca tatgcactca tcatactggt acgcattcaa caacaaaaca     60
gcaaccagaa ctccaaagct tgtgaagcac acattgttga ctcggttcaa ggatgagatc    120
acacgagaac agatcgacaa ctacattaat gactatacca atctgctcga tctcattcca    180
agcatgaaga gtttcaattg gggcacggat ctgggcatgg agtctgcgga gctaaaccga    240
ggatacactc atgcctttga atctacattt gagagcaagt ctggtttgca agagtacctc    300
gattctgctg ctcttgctgc atttgcagaa gggttttttgc ctactttgtc acagcgtctt    360
gtgatagact actttctcta ctaa                                            384

<210> SEQ ID NO 58
<211> LENGTH: 375
<212> TYPE: DNA
<213> ORGANISM: Artificial sequence
<220> FEATURE:
<223> OTHER INFORMATION: L3-SP1 coding sequence

<400> SEQUENCE: 58
atacaaaaac atatggatta ttttcatca ccatattatg aacaattatt tgcaaccaga      60
actccaaagc ttgtgaagca cacattgttg actcggttca aggatgagat cacacgagaa    120
cagatcgaca actacattaa tgactatacc aatctgctcg atctcattcc aagcatgaag    180
agtttcaatt ggggcacgga tctgggcatg gagtctgcgg agctaaaccg aggatacact    240
catgcctttg aatctacatt tgagagcaag tctggtttgc aagagtacct cgattctgct    300
gctcttgctg catttgcaga agggttttt cctactttgt cacagcgtct tgtgatagac    360
tactttctct actaa                                                      375

<210> SEQ ID NO 59
<211> LENGTH: 361
<212> TYPE: DNA
<213> ORGANISM: Artificial sequence
<220> FEATURE:
<223> OTHER INFORMATION: L6-SP1 coding sequence

<400> SEQUENCE: 59
agaaggagat atacaaaaac atatgtcaaa tcaatcagca accagaactc caaagcttgt     60
gaagcacaca ttgttgactc ggttcaagga tgagatcaca cgagaacaga tcgacaacta    120
cattaatgac tataccaatc tgctcgatct cattccaagc atgaagagtt tcaattgggg    180
cacggatctg gcatggagt ctgcggagct aaaccgagga tacactcatg cctttgaatc    240
tacatttgag agcaagtctg gtttgcaaga gtacctcgat tctgctgctc ttgctgcatt    300
tgcagaaggg ttttttgccta ctttgtcaca gcgtcttgtg atagactact ttctctacta    360
a                                                                    361

<210> SEQ ID NO 60
```

<211> LENGTH: 383
<212> TYPE: DNA
<213> ORGANISM: Artificial sequence
<220> FEATURE:
<223> OTHER INFORMATION: L4-Sp1 coding sequence

<400> SEQUENCE: 60

```
aaggagatat acaaaaacat atgcactggt cagcatggtg gatacgatca aatcaatcag    60
caaccagaac tccaaagctt gtgaagcaca cattgttgac tcggttcaag gatgagatca   120
caaaagaaca gatcgacaac tacattaatg actataccaa tctgctcgat ctcattccaa   180
gcatgaagag tttcaattgg ggcacggatc tgggcatgga gtctgcggag ctaaaccgag   240
gatacactca tgcctttgaa tctacatttg agagcaagtc tggtttgcaa gagtacctcg   300
attctgctgc tcttgctgca tttgcagaag gttttttgcc tactttgtca cagcgtcttg   360
tgatagacta ctttctctac taa                                           383
```

<210> SEQ ID NO 61
<211> LENGTH: 383
<212> TYPE: DNA
<213> ORGANISM: Artificial sequence
<220> FEATURE:
<223> OTHER INFORMATION: L5-Sp1 coding sequence

<400> SEQUENCE: 61

```
aaggagatat acaaaaacat atgcactggt cagcatggtg gatacgatca aatcaatcag    60
caaccagaac tccaaagctt gtgaagcaca cattgttgac tcggttcaag gatgagatct   120
gccgagaaca gatcgacaac tacattaatg actataccaa tctgctcgat ctcattccaa   180
gcatgaagag tttcaattgg ggcacggatc tgggcatgga gtctgcggag ctaaaccgag   240
gatacactca tgcctttgaa tctacatttg agagcaagtc tggtttgcaa gagtacctcg   300
attctgctgc tcttgctgca tttgcagaag gttttttgcc tactttgtca cagcgtcttg   360
tgatagacta ctttctctac taa                                           383
```

<210> SEQ ID NO 62
<211> LENGTH: 383
<212> TYPE: DNA
<213> ORGANISM: Artificial sequence
<220> FEATURE:
<223> OTHER INFORMATION: L7-SP1 coding sequence

<400> SEQUENCE: 62

```
aaggagatat acaaaaacat atgcactggt cagcatggtg gattcgttca aatcaatcag    60
caaccagaac tccaaagctt gtgaagcaca cattgttgac tcggttcaag gatgagatca   120
cacgagaaca gatcgacaac tacattaatg actataccaa tctgctcgat ctcattccaa   180
gcatgaagag tttcaattgg ggcacggatc tgggcatgga gtctgcggag ctaaaccgag   240
gatacactca tgcctttgaa tctacatttg agagcaagtc tggtttgcaa gagtacctcg   300
attctgctgc tcttgctgca tttgcagaag gttttttgcc tactttgtca cagcgtcttg   360
tgatagacta ctttctctac taa                                           383
```

<210> SEQ ID NO 63
<211> LENGTH: 383
<212> TYPE: DNA
<213> ORGANISM: Artificial sequence
<220> FEATURE:
<223> OTHER INFORMATION: L8_Sp1 coding sequence

<400> SEQUENCE: 63

```
aaggagatat acaaaaacat atgcactggt cagcatggtg gattcgttca aatcaatcag    60
caaccagaac tccaaagctt gtgaagcaca cattgttgac tcggttcaag gatgagatca   120
caaaagaaca gatcgacaac tacattaatg actataccaa tctgctcgat ctcattccaa   180
gcatgaagag tttcaattgg ggcacggatc tgggcatgga gtctgcggag ctaaaccgag   240
gatacactca tgcctttgaa tctacatttg agagcaagtc tggtttgcaa gagtacctcg   300
attctgctgc tcttgctgca tttgcagaag ggttttttgcc tactttgtca cagcgtcttg   360
tgatagacta ctttctctac taa                                           383
```

```
<210> SEQ ID NO 64
<211> LENGTH: 103
<212> TYPE: PRT
<213> ORGANISM: Artificial sequence
<220> FEATURE:
<223> OTHER INFORMATION: Sp1 mutant variant: amino acid 2-6 deleted

<400> SEQUENCE: 64

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

Asp Leu Ile Pro Ser Met Lys Ser Phe Asn Trp Gly Thr Asp Leu Gly
        35                  40                  45

Met Glu Ser Ala Glu Leu Asn Arg Gly Tyr Thr His Ala Phe Glu Ser
    50                  55                  60

Thr Phe Glu Ser Lys Ser Gly Leu Gln Glu Tyr Leu Asp Ser Ala Ala
65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100
```

```
<210> SEQ ID NO 65
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 65
ctgctcgatc tcattccaag ctgtaagagt ttcaattggg gcacg             45
```

```
<210> SEQ ID NO 66
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 66
gcaagtctgg tttgcaagag tactgcgatt ctgctgctct tgctg             45
```

```
<210> SEQ ID NO 67
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 67
```

```
aaaacatatg cgcaaacttc cggatgcggc aaccagaact ccaaagcttg          50
```

<210> SEQ ID NO 68
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 68

```
aaaagagctc ttagtaaaga agtaatcaa taac                            34
```

<210> SEQ ID NO 69
<211> LENGTH: 312
<212> TYPE: DNA
<213> ORGANISM: Artificial sequence
<220> FEATURE:
<223> OTHER INFORMATION: M43C delta N' SP1 coding sequence

<400> SEQUENCE: 69

```
atgaagcttg tgaagcacac attgttgact cggttcaagg atgagatcac acgagaacag   60
atcgacaact acattaatga ctataccaat ctgctcgatc tcattccaag ctgtaagagt   120
ttcaattggg gcacggatct gggcatggag tctgcggagc taaaccgagg atacactcat   180
gcctttgaat ctacatttga gagcaagtct ggtttgcaag agtacctcga ttctgctgct   240
cttgctgcat ttgcagaagg gttttttgcct actttgtcac agcgtcttgt gatagactac   300
tttctctact aa                                                        312
```

<210> SEQ ID NO 70
<211> LENGTH: 77
<212> TYPE: DNA
<213> ORGANISM: Artificial sequence
<220> FEATURE:
<223> OTHER INFORMATION: Single strand DNA oligonucleotide

<400> SEQUENCE: 70

```
aaggagatat acaaaaacat atgcactggt cagcatggtg gatacgatca aatcaatcag   60
caaccagaac tccaaag                                                   77
```

<210> SEQ ID NO 71
<211> LENGTH: 77
<212> TYPE: DNA
<213> ORGANISM: Artificial sequence
<220> FEATURE:
<223> OTHER INFORMATION: Single strand DNA oligonucleotide

<400> SEQUENCE: 71

```
ctttggagtt ctggttgctg attgatttga tcgtatccac catgctgacc agtgcatatg   60
tttttgtata tctcctt                                                   77
```

<210> SEQ ID NO 72
<211> LENGTH: 80
<212> TYPE: DNA
<213> ORGANISM: Artificial sequence
<220> FEATURE:
<223> OTHER INFORMATION: Single strand DNA oligonucleotide

<400> SEQUENCE: 72

```
agaaggagat atacaaaaac atatgcactc atcatactgg tacgcattca acaacaaaac   60
agcaaccaga actccaaagc                                                80
```

<210> SEQ ID NO 73
<211> LENGTH: 80
<212> TYPE: DNA
<213> ORGANISM: Artificial sequence
<220> FEATURE:
<223> OTHER INFORMATION: Single strand DNA oligonucleotide

<400> SEQUENCE: 73
gctttggagt tctggttgct gttttgttgt tgaatgcgta ccagtatgat gagtgcatat    60
gtttttgtat atctccttct                                                80

<210> SEQ ID NO 74
<211> LENGTH: 65
<212> TYPE: DNA
<213> ORGANISM: Artificial sequence
<220> FEATURE:
<223> OTHER INFORMATION: Single strand DNA oligonucleotide

<400> SEQUENCE: 74
atacaaaaac atatggatta tttttcatca ccatattatg aacaattatt tgcaaccaga    60
actcc                                                                65

<210> SEQ ID NO 75
<211> LENGTH: 65
<212> TYPE: DNA
<213> ORGANISM: Artificial sequence
<220> FEATURE:
<223> OTHER INFORMATION: Single strand DNA oligonucleotide

<400> SEQUENCE: 75
ggagttctgg ttgcaaataa ttgttcataa tatggtgatg aaaaataatc catatgtttt    60
tgtat                                                                65

<210> SEQ ID NO 76
<211> LENGTH: 56
<212> TYPE: DNA
<213> ORGANISM: Artificial sequence
<220> FEATURE:
<223> OTHER INFORMATION: Single strand DNA oligonucleotide

<400> SEQUENCE: 76
agaaggagat atacaaaaac atatgtcaaa tcaatcagca accagaactc caaagc        56

<210> SEQ ID NO 77
<211> LENGTH: 56
<212> TYPE: DNA
<213> ORGANISM: Artificial sequence
<220> FEATURE:
<223> OTHER INFORMATION: Single strand DNA oligonucleotide

<400> SEQUENCE: 77
gctttggagt tctggttgct gattgatttg acatatgttt ttgtatatct ccttct        56

<210> SEQ ID NO 78
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 78
actggtcagc atggtggatt cgatcaaatc aatcag                              36

```
<210> SEQ ID NO 79
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 79
ctgattgatt tgatcgaatc caccatgctg accagt                              36

<210> SEQ ID NO 80
<211> LENGTH: 37
<212> TYPE: DNA
<213> ORGANISM: Artificial sequence
<220> FEATURE:
<223> OTHER INFORMATION: Single strand DNA oligonucleotide

<400> SEQUENCE: 80
gtcagcatgg tggattcgtt caaatcaatc agcaacc                             37

<210> SEQ ID NO 81
<211> LENGTH: 37
<212> TYPE: DNA
<213> ORGANISM: Artificial sequence
<220> FEATURE:
<223> OTHER INFORMATION: Single strand DNA oligonucleotide

<400> SEQUENCE: 81
ggttgctgat tgatttgaac gaatccacca tgctgac                             37

<210> SEQ ID NO 82
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 82
tgactcggtt caaggatgag atcacaaaag aacagatcga ca                       42

<210> SEQ ID NO 83
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 83
tgtcgatctg ttcttttgtg atctcatcct tgaaccgagt ca                       42

<210> SEQ ID NO 84
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 84
actcggttca aggatgagat ctgccgagaa cagatcgaca actac                    45

<210> SEQ ID NO 85
<211> LENGTH: 45
<212> TYPE: DNA
<213> ORGANISM: Artificial sequence
<220> FEATURE:
<223> OTHER INFORMATION: Single strand DNA oligonucleotide
```

```
<400> SEQUENCE: 85
gtagttgtcg atctgttctc ggcagatctc atccttgaac cgagt            45

<210> SEQ ID NO 86
<211> LENGTH: 301
<212> TYPE: PRT
<213> ORGANISM: Artificial sequence
<220> FEATURE:
<223> OTHER INFORMATION: SP1-CBD chimeric polypeptide

<400> SEQUENCE: 86
```

| Met | Ala | Ala | Thr | Ser | Ser | Met | Ser | Val | Glu | Phe | Tyr | Asn | Ser | Asn | Lys |
|---|---|---|---|---|---|---|---|---|---|---|---|---|---|---|---|
| 1 | | | | 5 | | | | | 10 | | | | | 15 | |

Ser Ala Gln Thr Asn Ser Ile Thr Pro Ile Ile Lys Ile Thr Asn Thr
            20                  25                  30

Ser Asp Ser Asp Leu Asn Leu Asn Asp Val Lys Val Arg Tyr Tyr Tyr
        35                  40                  45

Thr Ser Asp Gly Thr Gln Gly Gln Thr Phe Trp Cys Asp His Ala Gly
    50                  55                  60

Ala Leu Leu Gly Asn Ser Tyr Val Asp Asn Thr Ser Lys Val Thr Ala
65                  70                  75                  80

Asn Phe Val Lys Glu Thr Ala Ser Pro Thr Ser Thr Tyr Asp Thr Tyr
                85                  90                  95

Val Glu Phe Gly Phe Ala Ser Gly Arg Ala Thr Leu Lys Lys Gly Gln
            100                 105                 110

Phe Ile Thr Ile Gln Gly Arg Ile Thr Lys Ser Asp Trp Ser Asn Tyr
        115                 120                 125

Thr Gln Thr Asn Asp Tyr Ser Phe Asp Ala Ser Ser Thr Pro Val
    130                 135                 140

Val Asn Pro Lys Val Thr Gly Tyr Ile Gly Gly Ala Lys Val Leu Gly
145                 150                 155                 160

Thr Ala Pro Ala Val Pro Ser Gly Ser Val Thr Ser Thr Ser Lys Thr
                165                 170                 175

Thr Thr Thr Ala Ser Lys Thr Ser Thr Ser Thr Ser Thr Ser Glu
            180                 185                 190

Phe Met Ala Thr Ser Thr Pro Lys Leu Val Lys His Thr Leu Leu Thr
        195                 200                 205

Arg Phe Lys Asp Glu Ile Thr Arg Glu Gln Ile Asp Asn Tyr Ile Asn
    210                 215                 220

Asp Tyr Thr Asn Leu Leu Asp Leu Ile Pro Ser Met Lys Ser Phe Asn
225                 230                 235                 240

Trp Gly Thr Asp Leu Gly Met Glu Ser Ala Glu Leu Asn Arg Gly Tyr
                245                 250                 255

Thr His Ala Phe Glu Ser Thr Phe Glu Ser Lys Ser Gly Leu Gln Glu
            260                 265                 270

Tyr Leu Asp Ser Ala Ala Leu Ala Ala Phe Ala Glu Gly Phe Leu Pro
        275                 280                 285

Thr Leu Ser Gln Arg Leu Val Ile Asp Tyr Phe Leu Tyr
    290                 295                 300

<210> SEQ ID NO 87
<211> LENGTH: 163
<212> TYPE: PRT
<213> ORGANISM: Artificial sequence
<220> FEATURE:
<223> OTHER INFORMATION: CBD domain

<400> SEQUENCE: 87

Met Ala Ala Thr Ser Ser Met Ser Val Glu Phe Tyr Asn Ser Asn Lys
1               5                   10                  15

Ser Ala Gln Thr Asn Ser Ile Thr Pro Ile Ile Lys Ile Thr Asn Thr
            20                  25                  30

Ser Asp Ser Asp Leu Asn Leu Asn Asp Val Lys Val Arg Tyr Tyr Tyr
        35                  40                  45

Thr Ser Asp Gly Thr Gln Gly Gln Thr Phe Trp Cys Asp His Ala Gly
    50                  55                  60

Ala Leu Leu Gly Asn Ser Tyr Val Asp Asn Thr Ser Lys Val Thr Ala
65                  70                  75                  80

Asn Phe Val Lys Glu Thr Ala Ser Pro Thr Ser Thr Tyr Asp Thr Tyr
                85                  90                  95

Val Glu Phe Gly Phe Ala Ser Gly Arg Ala Thr Leu Lys Lys Gly Gln
            100                 105                 110

Phe Ile Thr Ile Gln Gly Arg Ile Thr Lys Ser Asp Trp Ser Asn Tyr
        115                 120                 125

Thr Gln Thr Asn Asp Tyr Ser Phe Asp Ala Ser Ser Thr Pro Val
    130                 135                 140

Val Asn Pro Lys Val Thr Gly Tyr Ile Gly Gly Ala Lys Val Leu Gly
145                 150                 155                 160

Thr Ala Pro

<210> SEQ ID NO 88
<211> LENGTH: 108
<212> TYPE: PRT
<213> ORGANISM: Artificial sequence
<220> FEATURE:
<223> OTHER INFORMATION: Sp1 polypeptide

<400> SEQUENCE: 88

Met Ala Thr Ser Thr Pro Lys Leu Val Lys His Thr Leu Leu Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105

<210> SEQ ID NO 89
<211> LENGTH: 30
<212> TYPE: PRT
<213> ORGANISM: Artificial sequence

```
<220> FEATURE:
<223> OTHER INFORMATION: SP1-CBD fusion protein peptide linker.

<400> SEQUENCE: 89

Ala Val Pro Ser Gly Ser Val Thr Ser Thr Ser Lys Thr Thr Thr Thr
1               5                   10                  15

Ala Ser Lys Thr Ser Thr Ser Thr Ser Ser Thr Ser Glu Phe
            20                  25                  30
```

MULTI-SITE MODIFIED SP1 POLYPEPTIDES AND USES THEREOF

RELATED APPLICATIONS

This application is a division of U.S. patent application Ser. No. 13/394,181 filed on Apr. 23, 2012, which is a National Phase of PCT Patent Application No. PCT/IL2010/000705 having International filing date of Aug. 26, 2010, which claims the benefit of priority of U.S. Provisional Patent Application Nos. 61/358,973 filed on Jun. 28, 2010 and 61/272,230 filed on Sep. 3, 2009. The contents of the above applications are all incorporated herein by reference.

SEQUENCE LISTING STATEMENT

The ASCII file, entitled 61478SequenceListing.txt, created on Jan. 25, 2015, comprising 3,926,122 bytes, submitted concurrently with the filing of this application is incorporated herein by reference.

FIELD AND BACKGROUND OF THE INVENTION

The present invention, in some embodiments thereof, relates to material science in general, and, more particularly, to sequence variants of Stable Protein 1 (SP1), to uses thereof, and to new and improved composite materials based on these SP1 variants.

Stable protein 1 (SP1) is a homo-oligomeric protein isolated from aspen (*Populus tremula* aspen) plants which forms a ring-shape dodecameric particle with a central cavity. The oligomeric form of SP1 is an exceptionally stable structure that is resistant to proteases, such as trypsin, V8, and proteinase K, high temperatures, organic solvents, and high levels of ionic detergent.

WO 2002/070647, WO 2004/022697, U.S. Patent Application Nos. 20030092624, 20050074763 and 20060172298 and U.S. Pat. No. 7,253,341, teach novel denaturant-stable, protease resistant, homo-oligomeric stable protein (SP) variants, having chaperone-like activity as well as methods of production and purification of these novel SPs. These documents also provide nucleic acids encoding SPs, methods of isolating nucleic acids encoding SPs, antibodies recognizing SPs, and the use of these SPs for stabilizing, refolding, repairing, preventing aggregation and de-aggregating macromolecules such as proteins, fusion proteins including SPs, nucleic acid constructs encoding the fusion proteins and their uses in a variety of methods and applications.

WO 2007/007325 [PCT/IL2006/000795] teaches SP1 and modified SP1 variant polypeptides, capable of forming reversible and covalent molecular associations with substances, compositions-of-matter comprising same, and various uses thereof.

The use of proteins in the production of composite materials is of growing interest, for example, in the fields of nano-biotechnology and engineering, and biomaterials applications. However, while the naturally occurring variety of protein structure and function is impressive, biomaterial fabrication is inherently limited by the availability, inflexibility, low stability and non-specific binding of the native protein pool.

Proteins accumulate at interfaces, a property that can be both a practical asset and a drawback. Most proteins are large amphiphatic molecules, intrinsically surface-active, but whose interaction with surfaces is difficult to gauge. Prediction and determination of the parameters governing protein adsorption and desorption behavior is complicated by the interplay of intermolecular forces, such as Coulombic forces, Van der Waals forces, Lewis acid-base forces, entropically-based effects such as hydrophobic interactions, conformational entropy and restricted mobility, and intramolecular forces within the protein molecules affecting protein conformation.

Engineered proteins can allow a degree of synthetic flexibility, by providing specific binding domains, however, while the behavior of single peptide functional domains may be predicted to moderate accuracy, prediction of the behavior of engineered proteins comprising multiple domains is much more challenging due to higher order organization, increased size and complex topology. Likewise, although techniques such as phage display have provided a wealth of useful peptides that bind inorganic molecules, the mechanisms governing binding specificity and target recognition are poorly understood.

Carbon Nanotube Reinforced Composite Materials

Carbon nanotubes are nano-scale hollow cylinders of graphite carbon atoms. They provide the highest Young's modulus (stiffness), highest thermal conductivity, highest electrical conductivity, and highest current density of any known material, while having a low density. Carbon nanotubes come in two forms, as single-walled carbon nanotubes and multiwalled carbon nanotubes. Singlewalled carbon nanotubes tend to be stronger, more flexible, more transparent and better electrical conductors and are more transparent, but due to high production costs, multi-walled carbon nanotubes are more widely used in composite materials.

When carbon nanotubes are added to a matrix material, the composite will take on some of the carbon nanotubes' properties, due to the rule of mixtures. However, the theoretical property values of carbon nanotubes composites are presently not attained due to the inability to efficiently produce fully integrated composites.

Due to insufficient bonding across the interface of the nanotube and matrix material, before carbon nanotubes can be used in a broad range of applications, methods for manipulating the positioning, orientation, anchoring, grafting and binding of the carbon nanotubes to the matrix are presently required, particularly where such anchoring, grafting and binding is done without metal.

Thus, there is a widely recognized need for, and it would be highly advantageous to have SP1 variants capable of forming molecular complexes with carbon nanotubes useful for effective production of highly specific composite materials such as polymers and polymeric fabrics with integrated carbon nanotubes.

Tires:

Rubber is commonly compounded with carbon black to improve its tensile strength and wear resistance. The rubber composition of a tire tread is often compounded with silica, as a reinforcing agent in place of the carbon black, to improve rolling resistance and running performance (e.g. wet properties) of the tire. However, in silica compounded tires, due to the poor conductivity of the compounded rubber, static electricity charged in vehicles results in problematic and poorly controlled discharge phenomenon, resulting in radio noise, adverse influence to electronic circuit parts, generation of short-circuit, and the like.

Poor conductivity of rubber tires and tire tread is also an obstacle to efforts to obtain detailed, real time information regarding parameters of physical properties and function of the tire, especially during use. Thermal conductivity, a critical parameter to tire performance and safety, is also limited by the poorly conductive rubber compounds and fillers commonly used in tire manufacture.

Methods of enhancing electrical and thermal conductivity of tires have been proposed. US Patent Application 2010078103, to Nakamura, discloses a pneumatic tire comprising a tire carcass ply from conductive rubber material formed so as to create a continuous conductive path for discharge of static buildup to the road surface. Carbon-black reinforced rubber is envisioned as the conductive rubber material.

U.S. Pat. No. 7,528,186 to Halasa, et al, discloses a pneumatic tire with enhanced conductivity comprising a tire tread from conductive rubber material incorporating carbon black and an ionically conductive compound, such as tetrachloroaluminate; tetrafluoroborate; thiocyanate; thiosalicylate, phosphonium, imidazolium, pyrrolidinium and pyridinium, and the like.

U.S. Pat. No. 7,337,815 to Spadone discloses a pneumatic tire having tread fashioned from rubber compounds of varying carbon black contents, in order to improve thermal conductivity and heat transfer to the road during use.

U.S. Pat. No. 7,318,464 to Hahn et al discloses a pneumatic tire having an electrically conductive element adhesively bonded to the inner surface of the tire cavity, such as a wire, for example, for communicating information on tire status.

U.S. Pat. No. 7,284,583 to Dheur et al discloses a pneumatic tire comprising an electrically conductive cord, fashioned from carbon fiber, metal filament or a combination thereof, extending from the bead to the tread, in order to provide a path of least electrical resistance from tire mount to road-contact surface.

U.S. Pat. No. 7,131,474 to Sandstrom discloses a pneumatic tire with a carbon-black-rich tread zone providing an electrically conductive path from the tire throughout the tread to the road.

U.S. Pat. No. 7,581,439 to Rensel, et al. discloses a pneumatic tire incorporating micro-scale sensors or a sensor layer, which can be fashioned from a conductive polymer, for gathering and transmitting a wireless signal containing information on the tire condition and performance.

U.S. Patent Application 0070028958 to Retti discloses an electrical energy generating tire with a conductive strip, for example, a conductive polymer, and an energy generating component (such as a piezo-ceramic or thermal-harvesting material) incorporated into the tread and/or sidewall of the tire.

U.S. Patent Application 0090314404 to Rodgers et al discloses a tire having at least one active material element capable of modifying the performance characteristics of the tire (e.g. rolling resistance). Active materials are defined as compositions that can alter stiffness, modulus, shape and/or dimensions in response to an activation signal, such as shape memory alloys, electroactive polymers, piezo-electric materials, electrorheological elastomers and the like, suitable for embedding in a tire construction.

US Patent Application 20060061011 to Kikuchi et al discloses a pneumatic or solid tire fashioned from a composite material incorporating oriented carbon nanotubes, for enhanced thermal conductivity and heat dissipation from the tires.

However, methods for the production and use in tire manufacture of such composite materials incorporating elements having enhanced conductivity such as carbon nanotubes suffer from the shortcomings mentioned hereinabove (difficulties in integration, positioning, orientation, anchoring, grafting and binding of the carbon nanotubes to the matrix). Thus, it would be advantageous to have improved composite polymers and polymeric fabrics comprising integrated carbon nanotubes for enhancing electric and thermal conductivity of tires.

SUMMARY OF THE INVENTION

According to an aspect of some embodiments of the present invention there is provided an isolated chimeric polypeptide comprising an SP1 polypeptide and carbon nanotube or graphitic surfaces binding peptide at the N-terminus of the SP1 polypeptide, wherein the SP1 polypeptide is characterized by:

i) at least 65% amino acid homology to SEQ ID NO:1;

ii) stable dimer-forming capability; and iii) at least one conserved amino acid sequence in at least one region corresponding to amino acids 9-11, 44-46 and/or 65-73, of SEQ ID NO:4.

According to some embodiments of the invention, the carbon nanotube or graphitic surfaces binding peptide has an amino acid sequence selected from the group consisting of SEQ ID NOs: 10-13.

According to some embodiments of the invention the SP1 polypeptide having an amino acid sequence as set forth in any of SEQ ID NOs: 6, 8, 9, 14-18 and 86.

According to some embodiments of the invention there is provided a composition of matter comprising the chimeric polypeptide as indicated, non-covalently bound to a carbon nanotube or graphitic surface. According to some embodiments, the chimeric polypeptide can be as set forth in any of SEQ ID NOs: 6, 8, 9, 14-18 and 86. According to some embodiments, the chimeric polypeptide is as set forth in SEQ ID NO: 8.

According to some embodiments of the invention there is provided a composition of matter comprising at least one SP1 polypeptide-carbon-nanotube-complex bound to a polymer, fabric or polymeric fabric, to form an SP1-carbon nanotube-complexed polymer, fabric or polymeric fabric, wherein said SP1 polypeptide is a chimeric SP1 polypeptide as indicated. According to some embodiments, the chimeric polypeptide is as set forth in any of SEQ ID NOs: 6, 8, 9, 14-18 and 86. According to some embodiments, the chimeric polypeptide of the composition of matter is as set forth in SEQ ID NO: 8.

According to some embodiments, the carbon-nanotube-SP1 polypeptide-complexed polymer, fabric or polymeric fabric comprises SP1-carbon-nanotube-complexed aramid fibers.

According to some embodiments, the carbon-nanotube-SP1 polypeptide-complexed polymer, fabric or polymeric fabric comprises a woven or non-woven SP1 polypeptide-carbon-nanotube-complexed aramid fabric.

According to some embodiments, the SP1-polypeptide is as set forth in SEQ ID NO: 8. According to some embodiments the composition of matter further comprising a SP1-CBD fusion protein.

According to some embodiments, the SP1-CBD fusion protein is as set forth in SEQ ID NO: 86.

According to some embodiments, the, further comprising an elastomeric substance. According to some embodiments, the elastomeric substance is rubber.

According to some aspects of the present invention there is provided a pneumatic or semi-pneumatic tire having a component comprising the indicated composition of matter.

According to some embodiments of the invention, the component is a composite elastomeric substance formed with the SP1 polypeptide-carbon-nanotube-complexed polymer, fabric or polymeric fabric.

According to some embodiments of the invention SP1 polypeptide-carbon-nanotube-complexed polymer, fabric or polymeric fabric imparts improved heat and electrical conductivity, as compared to a tire devoid of the carbon-nanotube-SP1-complexed polymer, fabric or polymeric fabric.

According to some aspects of the present invention there is provided a method for racing a vehicle, the vehicle having tires as set forth hereinabove the method comprising providing an electric current to the at least one SP1-carbon-nanotube-complexed polymer, fabric or polymeric fabric, so as to change the temperature of the tire to a desired temperature, and racing the vehicle.

According to some aspects of the present invention there is provided an electrically conductive fabric comprising a fabric substrate material comprising a SP1 polypeptide-carbon nanotube-complex bound thereto, wherein the conductivity of the electrically conductive fabric is greater than that of the fabric substrate material devoid of said bound SP1 polypeptide-carbon nanotube-complex, wherein said SP1 polypeptide is a chimeric SP1 polypeptide as indicated hereinabove.

According to some embodiments, the fabric is a woven or non-woven fabric selected from the group consisting of cotton, wool, silk, nylon, polyester, aramid, polypropylene and elastane.

According to some aspects of some embodiments of the present invention, there is provided a method for manufacturing an electrically conductive polymer, fabric or polymeric fabric comprising: providing a fabric substrate material; preparing a composition of SP1 polypeptide-carbon nanotube-complex, and treating the fabric substrate material with the composition of SP1 polypeptide-carbon nanotube-complex, and washing the fabric substrate material to remove of excess of the composition of conductive SP1 polypeptide-carbon nanotube-complex, thereby imparting conductivity to the polymer, polymeric fabric or fabric substrate material, wherein the SP1 polypeptide is a chimeric SP1 polypeptide as indicated hereinabove.

According to an aspect of some embodiments of the present invention there is provided an isolated polynucleotide encoding a chimeric polypeptide comprising an SP1 polypeptide and carbon nanotube or graphitic surfaces binding peptide at the N-terminus of the SP1 polypeptide, wherein the SP1 polypeptide is characterized by:
  i) at least 65% amino acid homology to SEQ ID NO:1;
  ii) stable dimer-forming capability; and
  iii) at least one conserved amino acid sequence in at least one region corresponding to amino acids 9-11, 44-46 and/or 65-73, of SEQ ID NO:4. Also provided is a nucleic acid construct comprising the isolated polynucleotide, transcriptionally linked to at least one promoter for directing recombinant expression thereof.

According to an aspect of some embodiments of the present invention there is provided a composition of matter comprising an SP1 dodecamer which comprises at least one SP1 polypeptide having a modified amino acid sequence capable of binding a substance, the modified amino acid sequence being located at a region of the SP1 polypeptide corresponding to the central cavity region of an SP1 dodecamer, wherein the binding of the substance is enhanced in the presence of a chaotropic agent, wherein the composition of matter further comprising the chaotropic agent, and wherein the SP1 polypeptide is characterized by:
  i) at least 65% amino acid homology to SEQ ID NO:4;
  ii) stable dimer-forming capability; and
  iii) at least one conserved amino acid sequence in at least one region corresponding to amino acids 9-11, 44-46 and/or 65-73, of SEQ ID NO:4;
and wherein when the chaotropic agent is guanidinium hydrochloride, the modified amino acid sequence does not include a Ni-binding His tag.

According to some embodiments of the present invention, the modified amino acid sequence is modified to include a heterologous peptide selected from the group consisting of a carbon nanotube or graphitic surfaces binding peptide, a silicon binding peptide and a cellulose binding domain peptide.

According to some embodiments of the present invention, the carbon nanotube or graphitic surfaces binding peptide are selected from the group consisting of SEQ ID NOs: 10-13.

According to some embodiments of the present invention, the silicon binding peptide is selected from the group consisting of SEQ ID NOs: 5 and 19.

According to some embodiments of the present invention, the SP1 polypeptide comprises an N-terminal deletion.

According to some embodiments of the present invention, the chaotropic agent is selected from the group consisting of guanidinium hydrochloride, urea and lithium perchlorate.

According to some embodiments of the present invention, the SP1 polypeptide has an amino acid sequence as set forth in any of SEQ ID NOs: 1-4, 6, 8, 9 and 14-18 and 86.

According to an aspect of some embodiments of the present invention there is provided an isolated chimeric polypeptide comprising an SP1 polypeptide and a heterologous silicon binding peptide as set forth in SEQ ID NO: 5 at the N-terminus of the SP1 polypeptide, wherein the SP1 polypeptide is characterized by:
  i) at least 65% amino acid homology to SEQ ID NO:4;
  ii) stable dimer-forming capability; and
  iii) at least one conserved amino acid sequence in at least one region corresponding to amino acids 9-11, 44-46 and/or 65-73, of SEQ ID NO:4.

According to some embodiments of the present invention, the isolated chimeric polypeptide having an amino acid sequence as set forth in SEQ ID NO: 3 or SEQ ID NO: 1.

According to an aspect of some embodiments of the present invention there is provided a heteromeric composition of matter comprising at least a first and at least a second non-identical SP1 polypeptide monomer, the monomers comprising a modified amino acid sequence capable of binding a substance, wherein the modified amino acid sequence of the first and the second SP1 monomers are non-identical to each other, wherein the SP1 polypeptide is characterized by:
  i) at least 65% amino acid homology to SEQ ID NO:4;
  ii) stable dimer-forming capability; and
  iii) at least one conserved amino acid sequence in at least one region corresponding to amino acids 9-11, 44-46 and/or 65-73, of SEQ ID NO:4, wherein the non-identical monomers differ in their inorganic substance binding sequences.

According to some embodiments of the present invention, the modified amino acid sequence is selected from the group consisting of a carbon nanotube or graphitic surfaces binding peptide, a silicon binding peptide, an SP1-CBD fusion protein and a cysteine substitution.

According to some embodiments of the present invention, the modified sequence of the first and the second SP1 monomers bind non-identical substances.

According to some embodiments of the present invention, the heteromeric composition is a dodecamer.

According to an aspect of some embodiments of the present invention there is provided a composition of matter comprising a first inorganic substance complexed with a modified SP1 polypeptide dodecamer and a second inorganic substance complexed with the modified SP1 polypeptide dodecamer, wherein the first and the second inorganic substances are complexed via a first and a second binding region of the SP1 polypeptide dodecamer, and wherein the SP1 polypeptide is characterized by:
  i) at least 65% amino acid homology to SEQ ID NO:4;
  ii) stable dimer-forming capability; and
  iii) at least one conserved amino acid sequence in at least one region corresponding to amino acids 9-11, 44-46 and/or 65-73, of SEQ ID NO:4.

According to some embodiments of the invention, the at least one conserved amino acid sequence is selected from the group consisting of "HAFESTFES" (65-73 of SEQ ID NO:4), "VKH" (9-11 of SEQ ID NO:4) and "KSF" (44-46 of SEQ ID NO:4).

According to some embodiments of the present invention, the isolated chimeric polypeptide having an amino acid sequence as set forth in SEQ ID NO: 3 or SEQ ID NO: 1.

According to some embodiments of the present invention, at least one of the first or second inorganic substances is complexed with the modified SP1 polypeptide dodecamer by a non-covalent bond.

According to some embodiments of the present invention, at least one of the first or second inorganic substances are complexed with said modified SP1 polypeptide dodecamer by a covalent bond.

According to some embodiments of the present invention, at least one of the binding regions is a carbon nanotube or graphitic surface binding peptide and the second binding region is not a carbon nanotube or graphitic surface binding peptide.

According to some embodiments of the present invention, at least one of the binding regions of the first inorganic substance is a carbon nanotube or graphitic surface and the second inorganic substance is a polymer, a fabric or a polymeric fabric.

According to some embodiments of the present invention, the first binding region is a carbon nanotube or graphitic surface binding peptide and the second binding region is a silicon binding peptide.

According to some embodiments of the present invention, the SP1 polypeptide dodecamer comprises an SP1 polypeptide having an amino acid sequence as set forth in any of SEQ ID NOs: 1-3, 6, 8, 9, 14-18 and 86.

According to some embodiments of the present invention, the first inorganic substance is a carbon nanotube or graphitic surface.

According to another aspect of some embodiments of the present invention, there is provided a method of dispersing a substance in a solvent, the method comprising contacting the substance with a composition of matter or an isolated chimeric SP1 polypeptide as set forth hereinabove, in a manner to form a complex between the substance and the composition of matter or an isolated chimeric SP1 polypeptide; and
  contacting the complex with a solvent so as to form a solution or suspension;
  thereby dispersing the substance in the solvent.

According to some embodiments of the present invention, the solvent is an aqueous or organic solvent.

According to some embodiments of the present invention, the solvent is epoxy.

According to some embodiments of the present invention, the substance is a carbon nanotube.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

Figure 9A:
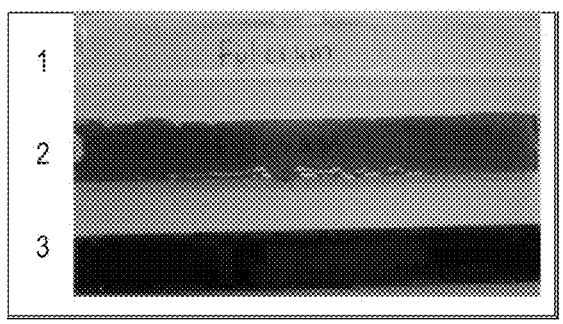
Figure 9B:
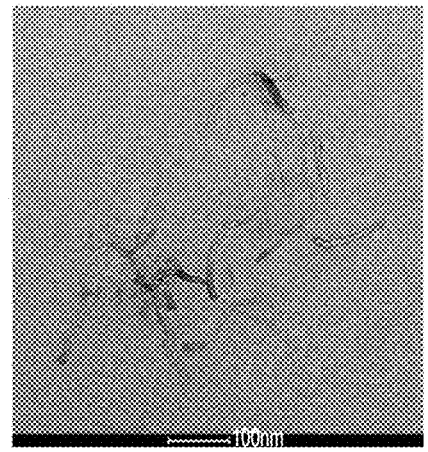

FIGS. 1A-B are computer-generated presentations of the M43C ΔNSP1 (SEQ ID NO:1) and L81C ΔNSP1 (SEQ ID NO:2) mutants as described in the background art, wherein FIG. 1A presents the M43C ΔNSP1 (SEQ ID NO:1) mutant exhibiting thiol groups at the protein inner ring or pore (green), and FIG. 1B presents the L81C ΔNSP1 (SEQ ID NO:2) mutant exhibiting thiol groups on the protein's outer rim (red);

FIGS. 2A-B are photographs of SDS-PAGE gel runs, performed for M43C SP1 (SEQ ID NO:1) and L81C SP1 (SEQ ID NO:2) mutants expression and stability experiments, wherein FIG. 2A showing the separation on PAGE of M43C SP1 from total bacterial extract before (lane 1) and after (lane 2) IPTG induction (the band of the M43C SP1 monomer is encircled with a solid line); bacterial soluble fraction not boiled (lanes 3, the band of the dodecamer is encircled with a dashed line) and boiled (lane 4, the band of the monomer is encircled with a solid line); bacteria inclusion bodies (lane 5); bacterial soluble fraction after heat treatment at 85° C. for 30 minutes) un-boiled and boiled (lanes 6 and 7 respectively); purified protein un-boiled and boiled (lanes 8 and 9, respectively); stability treatments sample exposed to 85° C., 100° C. and proteinase k (lanes 10, 11 and 12 respectively), and wherein FIG. 2B showing the analysis of L81C SP with samples in lanes 1-5 exposed to the same conditions as the samples in lanes 1-5 shown in FIG. 2A; refolded protein boiled and un-boiled (lanes 6 and 7 respectively); and samples in lanes 8-12 exposed to the same conditions as the samples in lanes 8-12 shown in FIG. 2A (MW scale in kDa);

FIGS. 3A-C are atomic force microscopy flooding topography images of three ultra flat gold surfaces wherein the blue colored areas represent the exposed gold surface and the red-brown areas represent the protein-covered surface, whereas each of the gold surfaces was treated with a different variant of SP1, namely wild-type SP1 (FIG. 3A) showing only 1.5% surface coverage, M43C ΔNSP1 (SEQ ID NO:1) showing only 60% surface coverage (FIG. 3B), and L81C ΔNSP1 (SEQ ID NO:2) showing a complete and homogenous coverage of 98% of the ultra flat gold surface (FIG. 3C);

FIGS. 4A-B are computer-generated graphic presentations of the mtbSP mutant (SEQ ID NO:3), showing the silica binding peptide as golden ribbons extending from the inner pore of the ring-shaped protein, wherein FIG. 4A depicts the closed conformation of the protein which cannot bind to silica, and FIG. 4B depicts the open conformation, effected by the presence of GuHCl, which can bind to silica surface;

FIGS. 5A-B are photographs of SDS-PAGE analysis of mtbSP (SEQ ID NO:3) expression, characterization and $SiO_2$ binding, wherein lane 1-2 in FIG. 5A contain the total bacteria lysate before (lane 1) and after (lane 2) IPTG induction, lanes 3-4 in FIG. 5A contain the bacteria soluble fraction boiled (lane 3) and not boiled (lane 4), lane 5 in FIG. 5A contains bacteria inclusion bodies lysate, lanes 6-7 in FIG. 5A contain bacteria soluble fraction after heat treatment (85° C. for 30 minutes) and then boiled (lane 6) and not boiled (lane 7), lanes 8-9 in FIG. 5A contain bacteria soluble fraction with (lane 8) and without (lane 9) proteinase k, and lanes 10-11 in FIG. 5A contain wild-type SP1 (SEQ ID NO:4) with (lane 10) and without (lane 11) proteinase k. Lanes 1-2 in FIG. 5B contain mtbSP (SEQ ID NO:3) bound (lane 1) and unbound (lane 1) to $SiO_2$, lanes 3-4 in FIG. 5B contain wild-type SP1 (SEQ ID NO:4) bound (lane 3) and unbound (lane 4) to $SiO_2$, lanes 5-6 in FIG. 5B contain a mix of mtbSP (SEQ ID NO:3) with wild-type SP1 (SEQ ID NO:4) bound (lane 5) and unbound (lane 6) to $SiO_2$, lanes 7-9 in FIG. 5B contain bound mtbSP (SEQ ID NO:3) (lane 7), wild-type SP1 (SEQ ID NO:4) (lane 8) and a mixture thereof (lane 9), all of which were not boiled prior to the separation on PAGE (MW is in kDa);

FIGS. 6A-B present comparative plots of $SiO_2$ binding of the silica-binding peptide mTBP (SEQ ID NO:5) (FIG. 6A) and the SP1 silica binding SP variant mtbSP (SEQ ID NO:3) protein (FIG. 6B) with the presence of GuHCl (open squares) or without the presence of GuHCl (Xs);

FIGS. 7A-C present comparative plots of the dissociation constants analysis (FIGS. 7A-B) and the Scatchard analysis (FIG. 7C) of mTB peptide binding (SEQ ID NO:5) and SP variant mtbSP (SEQ ID NO:3) protein binding to $SiO_2$ in the presence of 3M GuHCl, showing that mtbSP demonstrates positive cooperative binding (FIG. 7A), and mTB peptide (SEQ ID NO:5) demonstrates non-cooperative binding (FIG. 7B). FIG. 7C is a Scatchard plot of $SiO_2$ binding showing a $K_d$=0.3 μM for the variant protein mtbSP (SEQ ID NO:3) (open squares), and a $K_d$=86 μM for the mTB peptide (SEQ ID NO:5) (filled diamonds ♦);

FIGS. 8A-H are a series of AFM flooding topography images of different SP1 mutants bound to silica surfaces, showing their varied affinity to the $SiO_2$ surface in the presence and absence of 3M GuHCl, wherein the blue areas represent the bare surface area and the brown areas represent the silica-bound protein, whereas FIGS. 8A-D are of wild-type SP1 (SEQ ID NO:4), L81C ΔNSP1 (SEQ ID NO:2) variant, M43C ΔNSP1 (SEQ ID NO:1) variant and mtbSP1 (SEQ ID NO:3) variant, respectively, without the presence of GuHCl, all of which show low non-specific binding (less then 5% surface coverage) to $SiO_2$, and FIGS. 8E-H are of wild-type SP1 (SEQ ID NO:4), L81C ΔNSP1 (SEQ ID NO:2) variant, M43C ΔNSP1 (SEQ ID NO:1) variant and mtbSP1 (SEQ ID NO:3) variant, respectively, in the presence of 3M GuHCl, showing that only the mtbSP variant exhibits full coverage of the $SiO_2$ surface with reduced non-specific binding;

FIGS. 9A and 9B are photographs illustrating the dispersion of CNT by SP1-variants. FIG. 9A shows the clarity of modules produced from cured LY5052 epoxy (1), epoxy LY5052 with dispersed complex TiSP1 (mtbSP1, SEQ ID NO:3)-CNT (~1%) (2) and epoxy LY5052 with untreated CNT (1%)(3). Note the dark, yet clear sample in 2; FIG. 10B shows a TEM image of a thin section of epoxy LY5052 with dispersed complex TiSP1-CNT (~1%)(mtbSP1), indicating full dispersion of the CNT in the cured, polymerized epoxy;

FIGS. 10A-10B illustrate the binding of SP-1 variants and SP-1 variant-CNT complexes to KEVLAR fibers. FIG. 10A is a graph demonstrating the binding of L3SP1 (SEQ ID NO: 8) to KEVLAR, as a function of concentration, as detected by protein assay of the washed fibers. FIG. 10B shows a SDS PAGE analysis of SP1/CNT-bound to KEVLAR™ following incubation of L4-SP1 (SEQ ID NO: 9)-CNT complex (180 μg protein/ml, 1000 μg CNT/ml; 10 mM $NaP_i$, pH-8) with 30 mg KEVLAR™ with sonication, extensive washing and boiling. 20 ul of the total fraction (lane 1), the unbound fraction (lane 2) and the extracted fiber faction (boiled in application buffer; 40 ul each)(lane 3), were applied to SDS PAGE. Note that the protein as well as CNT are clearly bound to the fiber;

FIGS. 11A-11C are high resolution scanning electron microscopy (HR-SEM) images illustrating binding of SP1 polypeptide-carbon-nanotube-complex to an aramid fiber. SP1-polypeptide (L3SP1, SEQ ID NO: 8)-bound carbon nanotubes (CNT) dispersed in sodium phosphate buffer were incubated with the aramid fabric (Kevlar style 120 plain weave), agitated, rinsed and air dried, overnight. Binding of approximately 7 mg CNT/gram fabric was observed. High resolution, secondary electron microscope images were obtained using the high resolution low voltage SEM ULTRA (HR-SEM) at accelerating voltages 3 keV. Scale for the HR-SEM images is bar=10 μm, 1.0 μm and 0.1 μm in panels 11A, 11B and 11C, respectively. Note the abundant CNT bound to the fabric surface (see FIG. 11C), resulting in highly increased surface area, and close contact between CNTs;

FIGS. 12A-12C illustrate the binding of SP-1 variants and SP-1 variant/CNT complexes to carbon fiber material. L3-SP-1 (SEQ ID NO: 8) was incubated with 50 mg carbon fibers (Sigmatex) (0, 1, 2, 4, and 8 mg protein/g carbon fibers) in a bath sonicator for 1.5 hours, followed by extensive buffer wash. SP1 binding to the washed fabric was determined by protein assay (FIG. 12A) and determined by optical density at 562 nm. Note that the SP1/fabric (w/w) ratio of the bound fabric is up to 7 mg protein/g fiber (0.07%). FIG. 12B is a standard curve of transmittance values (at 600 nm) plotted against concentration of CNT in solution. FIG. 12C shows the increased transmittance (decreased OD at 600 nm, samples diluted 100-fold) with increasing time of sonication of the carbon fibers in the L3SP1/CNT suspension. Carbon fibers [pretreated with L3SP1 (SEQ ID NO:8)] were sonicated with L3SP-1/CNT complex for 5 hours, and the loss of CNT from the solution (increased transmittance) indicates binding of the CNT from the L3-SP-1/CNT solution to the carbon fiber fabric;

FIGS. 13A-13B are high resolution scanning electron microscopy (HR-SEM) images of MWCNT bound carbon fabric, illustrating two-stage binding of SP1 polypeptide-carbon-nanotube-complex to an carbon fiber. Carbon Fiber (Hexcel, plain wave style K-70-P 3000 filament yarn) was treated with a solution of CBD-SP1 fusion protein (SEQ ID NO: 86), washed extensively and incubated with an SP1-polypeptide (L3SP1, SEQ ID NO: 8)-bound carbon nanotubes (CNT) suspension, washed and air dried over night. CNT content on fabric was about 6 mg/g fabric. Secondary electron microscope (HR-SEM) images, obtained as above, show extensive and homogeneous binding of the SP1-polypeptide-bound carbon nanotubes (CNT) to the fabric, with no aggregation.

DESCRIPTION OF EMBODIMENTS OF THE INVENTION

The present invention, in some embodiments thereof, relates to material science in general, and, more particularly, to sequence variants of Stable Protein 1 (SP1), to uses thereof, for binding of carbon nanotubes, production of composite polymers and polymer materials, such as fabrics, based on SP1-polypeptide-carbon nanotube-complexes, and uses thereof, for example, for enhancing conductivity in tires.

Specifically, the present invention can be used to bind and controllably display inorganic substances, to enhance their dispersion in a solvent, and as a bi- or multi-functional reagent for incorporation of inorganic substances into composite materials. Further, the homo- and hetero-oligomeric complex of SP1 variant polypeptides of the present invention can be manipulated, for example, by exposure to chaotropic agents, to selectively modify binding of inorganic substances. Yet further, the present invention is of composite polymer elements incorporating integrated carbon nanotubes via SP1 variants, having enhanced thermal and electrical conductivity, which can be used, for example, for incorporation into tires, for improved rolling resistance, static discharge, heat dissipation, tire condition monitoring and control of physical parameters of the tire. Additional aspects and applications of the invention are further discussed below.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

SP1 polypeptide is an exceptionally stable polypeptide, forming hetero- and homo-oligomers which are resistant to denaturation by heat and most chemical denaturants, resistant to protease digestion, and capable of stabilizing molecular interactions and forming three dimensional structures (Dgany et al, JBC, 2004; 279:51516-23, and U.S. Pat. No. 7,253,341 to Wang et al)

The present inventors have previously uncovered SP1 proteins fused to other protein or non-protein molecules, for enhancement of binding properties of binding molecules, for stabilization of the fused molecules (such as enzymes) and for enhancement or alteration of immunological properties of the fused molecules (U.S. Pat. No. 7,253,341 to Wang et al.). SP1 fusion proteins, as disclosed in U.S. Pat. No. 7,253,341, comprise recombinant SP1 molecules having additional polypeptide sequences added by genetic engineering techniques, and SP1 molecules having additional non-protein moieties added by chemical means, such as cross linking. The present inventors have further disclosed the therapeutic use of SP1 proteins for strengthening skin, hair, nails, etc.

PCT IL 2006/000795 discloses SP1 and SP1 variants forming molecular complexes with small molecules, peptides, nucleic acid fragments, inorganic nanostructures and other ligands, for molecular complexing of drugs and delivery as well as control release of complexed ligands.

The present invention is based on the discovery that a chimeric polypeptide comprising an SP1 polypeptide and a heterologous inorganic substance binding peptide can form highly specific and controllable complexes with a variety of inorganic substances, molecules and surfaces. The three dimensional conformation of the chimeric SP1 molecules of the present invention allows presentation of multiple copies of the inorganic substance binding peptides, enhancing their avidity for their target molecules and resulting in modified and improved binding strength. This makes the chimeric SP1 polypeptides of the present invention exceptionally useful for, for example, enhancing dispersion and binding properties of the inorganic molecules, acting as multi-functional reagents and for the design and production of composite materials.

Accordingly, chimeric SP1 polypeptides of the present invention can be used for enhancing dispersion of poorly soluble materials, for example carbon nanotubes, in solvents and polymers, and modification of inorganic materials, polymers and surfaces by binding of complexed chimeric SP1-inorganic substances. The chimeric SP1 polypeptides of the present invention can be used to produce composite materials having enhanced physical characteristics such as improved storage modulus, increased tensile strength, ballistic resistance, electrical conductivity, optical activity, heat conductivity, surface interactivity, magnetic properties, electromagnetic radiation absorption spectrum and the like. For example, dispersion of carbon nanotubes complexed with chimeric SP1-carbon nanotube or graphitic surface binding peptides in polymers such as epoxy results in superior dispersion of the chimeric SP1-carbon nanotube complexes, and exposure, under controlled conditions, of carbon nanotubes complexed with chimeric SP1-carbon nanotube or graphitic surface binding peptides to polymers such as aramid (e.g. Kevlar®) results in superior, controllable binding of the chimeric SP1-carbon nanotube complexes to the polymer surfaces, producing electrically and thermally conductive polymers and polymer fabrics.

Carbon nanotubes (CNTs), according to the present invention, include, but are not limited to, multi-wall carbon nanotubes (MWNTs), single-wall carbon nanotubes (SWNTs), double-wall carbon nanotubes (MWNTs), small-diameter carbon nanotubes (having diameters less than ca. 3.5 nm), buckytubes, fullerene tubes, carbon fibrils, and combinations thereof. Such carbon nanotubes can be synthesized via a variety of routes and can be of a variety of lengths, diameters, chiralities (helicities), and purity. Such carbon nanotubes can be endohedrally-doped. Furthermore, the population of a CNT sample can be substantially homogeneous or inhomogeneous in terms of length, diameter, chirality, and/or electronic type. In some embodiments, efforts are taken to purify the nanotubes, and/or separate the nanotubes by type. See, e.g., Chiang et al., J Phys. Chem. B, 2001, 105:8297-8301; and Dyke et al., J. Am. Chem. Soc. 2005, 127:4497-4509; respectively. For a discussion of SWNT types, see Bachilo et al., Science, 2002, 298:2361-2366; and Weisman et al., Nano Lett., 2003, 3:1235-1238.

Chimeric SP1 polypeptides of the present invention are also useful for binding silicon compounds and materials such as glass, and binding to metallic surfaces such as gold. The bi- and multi-functional binding properties of chimeric SP1 polypeptides enable their use for securing uniform coatings to surfaces, such as pigments, flame retardants and the like. Chimeric SP1 polypeptides of the present invention can also bind to fibers, and can be used to modify the physical properties of inorganic fibers and fabric such as aramid (Kevlar™ and Twaron™), silk, polyester, glassfiber, polyamide, cotton and carbon fibers. Examples of assays for measuring such alteration of properties are described in detail hereinbelow.

SP1 polypeptides can be used as a protein scaffold for the presentation of surface active moieties. A versatile protein scaffold should generally constitute a conformationally stable folding entity that is able to display a multitude of loop structures or amino-acid sequences in a localized surface region. SP1 can be engineered to display various moieties contributing to their binding capability in a cooperative manner. Moreover, peptide exposure can be manipulated under solvent conditions that reduce non-specific binding.

Thus, according to one aspect of the present invention there are provided isolated chimeric polypeptides comprising an SP1 polypeptide and a heterologous inorganic molecule binding peptide, wherein the SP1 polypeptide is characterized by: i) at least 65% amino acid homology to native SP1 (SEQ ID NO: 4); ii) stable dimer-forming capability; and iii) at least one conserved amino acid sequence in at least one region corresponding to amino acids 9-11, 44-46 and/or 65-73, of SEQ ID NO:4.

As used herein the phrase "SP1 polypeptide" refers to a protein having at least the following characteristic properties: at least 65% sequence homology to SEQ ID NO:4; being capable of forming stable dimers, and having at least one conserved amino acid sequence in at least one region corresponding to amino acids 9-11, 44-46 and/or 65-73, of SEQ ID NO:1, as determined using a Best Fit algorithm of GCG, Wisconsin Package Version 9.1, using a plurality of 10.00, a threshold of 4, average weight of 1.00, average match of 2.91 and average mismatch of minus 2.00. In some embodiments, the SP1 polypeptide has conserved consensus sequences: "HAFESTFES" (65-73, SEQ ID NO:1), "VKH" (9-11, SEQ ID NO:1) and "KSF" (44-46, SEQ ID NO:1). According to one embodiment of the invention, "wild-type" or "native" SP1 is the stress related SP1 protein from aspen (SEQ ID NO:4), as disclosed by Wang et al (U.S. patent application Ser. No. 10/233,409, filed Sep. 4, 2002, now U.S. Pat. No. 7,253,341, issued Aug. 7, 2007, which is a Continuation in Part of PCT IL 02/00174, filed Mar. 5, 2002, both of which are incorporated by reference as if fully set forth herein.).

In one embodiment, the SP1 protein is 70%, 75%, 80%, 85%, 90%, 95%, or up to 100% homologous to SEQ ID NO: 4. It will be appreciated that SP1 homologues have been identified in plant species other than aspen, and that these SP1 homologues can be suitable for use with the present invention, when fulfilling the abovementioned criteria.

SP1 polypeptide has been characterized as denaturant stable, boiling stable, detergent stable and having chaperone-like activity. As used herein the phrase "denaturant-stable" refers to major (above 50%) structural oligomeric stability following a denaturation treatment in aqueous solution. A denaturation treatment can include boiling and exposure to a chemical denaturant, such as, a detergent (e.g., SDS), urea, or guanidinium-HCl.

As used herein, the phrase "boiling stable" refers to major (above 50%) structural oligomeric stability following treatment at substantially 100° C. in aqueous solution for at least 10 minutes, as determined by a size fractionation assay.

As used herein, the phrase "detergent stable" refers to major (above 50%) structural oligomeric stability of an oligomeric protein following treatment in aqueous solution containing 1/2,000 molar ratio (monomer:SDS), as determined by a size fractionation assay.

As used herein in the specification and in the claims section that follows, the phrase "protease resistant" refers to major (above 50%) stability and retention of physical and function characteristics following treatment in aqueous solution containing 50 μg per ml proteinase K for at least 60 minutes at 37° C.

As used herein, the phrase "chaperone-like activity" refers to the ability to mediate native folding and native oligomerization of proteins, to prevent the formation of incorrect protein structures, to unscramble existing incorrect protein structures and to limit stress-related damage by inhibiting incorrect interactions that could occur between partially denatured proteins or their domains.

As used herein, the terms "isolated" or "substantially pure," when used as a modifier of the chimeric SP1 polypeptides of the present invention, means that they are produced by human intervention and are separated from their native in vivo-cellular environment. Generally, polypeptides and polynucleotides so separated are substantially free of other proteins, nucleic acids, lipids, carbohydrates or other materials with which they are naturally associated.

The SP1 polypeptide of the chimera can be native SP1 (for example, SEQ ID NO: 4), or can be an SP1 polypeptide having a modified amino acid sequence. In some embodiments modified SP1 polypeptides retain the above-mentioned activities of native SP1 polypeptide such as ability of forming oligomer and complexes that are pH-stable, heat-stable and denaturant- and protease-resistant (see, for example, Examples 2 and 3, FIG. 5).

As mentioned hereinabove, SP1 variant polypeptides can be modified to impart specific properties to the SP1 variant, thereby rendering the molecular complexing with, and release of other substances more efficient and controllable, and adaptable to specific conditions. Dgany et al (JBC 2004 279:51516-523) have identified a number of structurally significant regions in the SP1 polypeptide.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S═O, O═C—NH, CH2-O, CH2-CH2, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, the chimeric SP1 polypeptides contemplated herein include, but are not limited to, modifications to side chains, incorporation of unnatural amino acids and/or their derivatives during peptide synthesis and the use of crosslinkers and other methods which impose conformational constraints on the peptides or their analogues.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5'-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1-2 below list all the naturally occurring amino acids (Table 1) and non-conventional or modified amino acids (Table 2).

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Iie | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-Carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-Carboxylate | Norb | L-N-methylglutamine | Nmgin |
|  |  | L-N-methylglutamic acid | Nmglu |
| Cyclohexylalanine | Chexa | L-N-methylhistidine | Nmhis |
| Cyclopentylalanine | Cpen | L-N-methylisolleucine | Nmile |
| D-alanine | Dal | L-N-methylleucine | Nmleu |
| D-arginine | Darg | L-N-methyllysine | Nmlys |

TABLE 2-continued

| Non-conventional amino acid | Code | Non-conventional amino acid | Code |
|---|---|---|---|
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |

TABLE 2-continued

| Non-conventional amino acid | Code | Non-conventional amino acid | Code |
| --- | --- | --- | --- |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

The peptides of the present invention may be utilized in a linear form, although it will be appreciated that in cases where cyclicization does not severely interfere with peptide characteristics, cyclic forms of the peptide can also be utilized.

According to one embodiment of the present invention the inorganic binding peptide is a heterologous silicon binding peptide, for example RKLPDAA (mtb), as set forth in SEQ ID NO: 5. In one exemplary embodiment, the resulting chimeric polypeptide comprising an SP1 polypeptide and the heterologous silicon binding peptide (mtb) has the amino acid sequence as set forth in SEQ ID NO: 3.

In another embodiment, the binding peptide binds carbon fibers or surfaces. Thus, the chimeric polypeptides can be used to bind carbon nanotubes and/or graphitic surfaces. Thus, according to further aspects of the present invention there is provided a chimeric polypeptide comprising an SP1 polypeptide and a carbon nanotube or graphitic surfaces binding peptide. Carbon nanotube binding peptides suitable for use with the chimeric polypeptide of the invention are well known in the art, for example, the peptides disclosed in U.S. Pat. No. 7,304,128 to Jagoda et al. According to some embodiments, the carbon nanotube or graphitic surfaces binding peptide is HWSAWWIRSNQS (SEQ ID NO: 10), HSSYWYAFNNKT (SEQ ID NO: 11), DYFSSPYYEQLF (SEQ ID NO:12) or SNQS (SEQ ID NO:13) and the chimeric SP1 polypeptide has an amino acid sequence as set forth in SEQ ID NOs:6, 8, 9 and 14-18. In certain embodiments, the carbon nanotube or graphitic surfaces binding peptide is located at the N-terminus of the SP1 polypeptide.

According to another embodiment, the inorganic binding peptide is a heterologous titanium binding peptide such as, for example, RKLPDA (SEQ ID NO:5) or RALPDA (SEQ ID NO: 19).

Peptides binding inorganic substances, particularly solids, can be designed using computational biology tools and have been the subject of much investigation. Numerous inorganic-substance binding peptide motifs suitable for use in the SP1 chimeras have been elucidated (see, for example, Sarikaya et al., Ann Rev Mater Res 2004; 34:373-408; incorporated by reference as if fully set forth herein).

In some embodiments, peptides that non-specifically bind to materials can be used with the invention. These include, but are not limited to repeated tyrosine rich motifs from specific mussel proteins (mfp1), where the tyrosine residues may be converted to L-DOPA (L-3,4-dihydroxyphenylalanine) (Holten-Andersen & Waite *J Dent Res* 87(8):701-709, 2008), such as AKPSYPPTYK, (SEQ ID NO: 20), AKPTYK (SEQ ID NO: 21), PKISYPPTYK (SEQ ID NO: 22), APPPAXTAXK (SEQ ID NO: 23), ATPKPXTAXK (SEQ ID NO: 24), PYVK (SEQ ID NO: 25), AKPSPYVPTGYK (SEQ ID NO: 26), GQQKQTAYDPGYK (SEQ ID NO: 27).

In yet another embodiment, polystyrene (PS) binding peptides highly enriched in aromatic residues (Phe, Tyr, Trp, His) can be used with the invention (Adey et al., Gene, 1995; 14:27-31; Ph.D.™-C7C Phage Display Peptide Library Kit Manual, New England Biolab, see the New England Biolab website)

Modifications of the SP1 polypeptide can enhance the proteins functionality, for example, in interaction with a surface. Thus, according to yet further aspects of the present invention there is provided an isolated SP1 polypeptide having the amino acid substitution M43C, comprising an amino acid sequence as set forth in SEQ ID NO: As detailed herein, substitution of the cysteine at amino acid coordinate 43 of SP1 resulted in an SP1 oligomeric complex having enhanced binding to surfaces, such as flat gold.

As used herein, a chimeric polypeptide refers to an amino acid sequence having two or more parts which generally are not found together in a single amino acid sequence in nature. Chimeric SP1 polypeptides are defined herein as polypeptides comprising an SP1 polypeptide and a non-SP1 oligo- or polypeptide having binding affinity for inorganic molecules such as metals and other ions, the SP1 polypeptide and the non-SP1 component connected through a peptide bond.

The chimeric polypeptides of the present invention and modifications thereof can be prepared by a variety of methods known in the art. The polypeptides of the present invention may be synthesized by any techniques that are known to those skilled in the art of peptide or protein synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

Modifications to the SP1 polypeptides can be introduced by site-directed (e.g., PCR based) or random mutagenesis (e.g., EMS) by exonuclease deletion, by chemical modification, or by fusion of polynucleotide sequences encoding a heterologous domain or binding protein, for example. As detailed herein, chimeric polypeptides can be obtained by expression of a polynucleotide encoding the polypeptide in a host cell, such as a bacteria, yeast or mammalian cell, and purifying the expressed chimeric polypeptide by purification using typical biochemical methods (e g, immunoaffinity purification, gel purification, expression screening etc). Other well-known methods are described in Deutscher et al., (Guide to Protein Purification: Methods in Enzymology, Vol. 182, Academic Press (1990), which is incorporated herein by reference).

Signals for post translational modification of the recombinant polypeptide, such as glycosylation, can also be introduced into the coding sequence.

Thus, according to another aspect of the present invention, there is provided an isolated polynucleotide comprising a nucleic acid sequence encoding any of the above described chimeric polypeptides.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

The term "isolated" refers to at least partially separated from the natural environment e.g., from a plant cell.

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

In some embodiments, the SP1 polynucleotide sequence is 70%, 75%, 80%, 85%, 90%, 95%, or up to 100% homologous to SEQ ID NO: 28. It will be appreciated that polynucleotides encoding SP1 homologues SEQ ID NOs: 29-54 can be suitable for producing the SP1 polypeptide of the present invention, when fulfilling the abovementioned criteria.

According to specific embodiments the isolated polynucleotides comprise a nucleic acid sequence encoding a modified SP1 polypeptide having an amino acid sequence as set forth in any of SEQ ID NOs: 1-4, 6, 8, 9, 14-18 and 86.

It will be appreciated that the polynucleotide of the present invention can be introduced into a vector for recombinant expression in a host organism. According to another aspect of the present invention there is provided a nucleic acid construct comprising the isolated nucleic acid (e.g., encoding the above chimeric polypeptide) described herein.

According to a preferred embodiment the nucleic acid construct according to this aspect of the present invention further comprising a promoter for regulating the expression of the polynucleotide. Such promoters are known to be cis-acting sequence elements required for transcription as they serve to bind DNA dependent RNA polymerase which transcribes sequences present downstream thereof.

While the polynucleotide described herein is an essential element of the invention, it can be used in different contexts. The promoter of choice that is used in conjunction with the polynucleotide of the invention is of secondary importance, and will comprise any suitable promoter. It will be appreciated by one skilled in the art, however, that it is necessary to make sure that the transcription start site(s) will be located upstream of an open reading frame. In a preferred embodiment of the present invention, the promoter that is selected comprises an element that is active in the particular host cells of interest, be it a bacteria, yeast or a higher cell of a plant or animal.

A construct according to the present invention preferably further includes an appropriate selectable marker. In a more preferred embodiment according to the present invention the construct further includes an origin of replication. In another most preferred embodiment according to the present invention the construct is a shuttle vector, which can propagate both in *E. coli* (wherein the construct comprises an appropriate selectable marker and origin of replication) and be compatible for propagation in cells, or integration in the genome, of an organism of choice. The construct according to this aspect of the present invention can be, for example, a plasmid, a bacmid, a phagemid, a cosmid, a phage, a virus or an artificial chromosome.

The construct of the present invention can be used to express the polypeptide encoded thereby in a variety of species ranging from bacteria such as *E. coli*, yeast cells or higher cells such as the cells of a plant. Expression can be selected stable or transient.

For effecting plant transformation, the exogenous polynucleotides which encode chimeric SP1 production are preferably included within a nucleic acid construct or constructs which serve to facilitate the introduction of the exogenous polynucleotides into plant cells or tissues and the expression of the chimeric SP1 polypeptides in the plant.

Thus, in some embodiments, the present invention provides polynucleotides encoding chimeric SP1 polypeptides having heterologous inorganic binding peptide sequences. SEQ ID NO:55 encodes a chimeric SP1 polypeptide comprising the silicon oxide binding peptide sequence RKLP-DAA. SEQ ID NO:56 encodes a chimeric SP1 polypeptide comprising the carbon nanotube binding peptide sequence HWSAWWIRSNQS. SEQ ID NO:57 encodes a chimeric SP1 polypeptide comprising the carbon nanotube binding peptide sequence HSSYWYAFNNKT. SEQ ID NO:58 encodes a chimeric SP1 polypeptide comprising the carbon nanotube binding peptide sequence DYFSSPYYEQLF. SEQ ID NO:59 encodes a chimeric SP1 polypeptide comprising the carbon nanotube binding peptide sequence SNQS. SEQ ID NO:60 encodes a chimeric SP1 polypeptide comprising the carbon nanotube binding peptide sequence HWSAW-WIRSNQS having an R23K substitution. SEQ ID NO:61 encodes a chimeric SP1 polypeptide comprising the carbon nanotube binding peptide sequence HWSAWWIRSNQS having a T22C substitution. SEQ ID NO:62 encodes a chimeric SP1 polypeptide comprising the carbon nanotube binding peptide sequence HWSAWWIRSNQS, with mutations A24T and A27T for improved codon usage. SEQ ID NO:63 encodes a chimeric SP1 polypeptide comprising the carbon nanotube binding peptide sequence HWSAW-WIRSNQS, with mutations A24T and A27T for improved codon usage and having an R23K substitution.

As used herein the term "heterologous" refers to a peptide sequence that is not part of the native SP1 polypeptide sequence. In some embodiments, the heterologous sequence can be a synthetic sequence unrelated to SP1 protein sequence.

In other embodiments, the heterologous sequence can be derived from a "foreign" polypeptide unrelated to SP1. In a specific embodiment, the heterologous sequence is derived from a cellulose binding domain (CBD) peptide. Production, cloning and recombinant expression of an exemplary, non-limiting CBD-SP1 fusion protein is described in detail in WO 2004/022697, which is fully incorporated by reference herein. Surprisingly, it was uncovered that SP1-CBD fusion protein binds fibers, fabrics and fabric substrates, as well as to carbon nanotubes with high affinity. Thus, according to one aspect of the present invention there is provided a composition of matter comprising an SP1-CBD chimeric polypeptide complexed with carbon nanotubes.

The SP1-CBD chimeric polypeptide complexed with carbon nanotubes can be used to bind carbon nanotubes to textiles, yarns, fabrics and the like. Thus, in one embodiment, there is further provided an SP1-CBD chimeric polypeptide-carbon nanotube-complexed polymer, fabric or polymeric fabric. In one embodiment, the SP1-CBD chimeric polypeptide comprises a cellulose binding domain of Clostridium cellovorans binding protein. An another embodiment, the SP1-CBD chimeric polypeptide comprises a CBD domain as set forth in SEQ ID NO: 87. In still another embodiment, the SP1-CBD chimeric polypeptide comprises a peptide linker positioned between the SP1 polypeptide and the CBD amino acid sequence. One exemplary, non-limiting linker is as set forth in SEQ ID NO: 89. In yet another embodiment, the SP1-CBD chimeric polypeptide is as set forth in SEQ ID NO: 86.

According to some aspects of some embodiments of the present invention, there is provided a method for method for manufacturing an electrically conductive polymer, fabric or polymeric fabric comprising: providing a fabric substrate material; preparing a composition of SP1 polypeptide-carbon nanotube-complex, and treating the fabric substrate material with the composition of SP1 polypeptide-carbon nanotube-complex, and washing the fabric substrate material to remove of excess of said composition of conductive SP1 polypeptide-carbon nanotube-complex, thereby imparting conductivity to the polymer, polymeric fabric or fabric substrate material, wherein the SP1 polypeptide is a chimeric SP1 polypeptide of the present invention. In some embodiments, the fabric, yarn or textile is exposed to a composition comprising SP1-CBD chimeric polypeptide so as to form a complex with the SP1-CBD chimeric polypeptide, followed by contacting said SP1-CBD chimeric polypeptide-complexed yarn-fabric or textile with CNT or SP1-CNT (such as, for example, SP1-L3-CNT), so as to form a SP1-CBD chimeric polypeptide-complexed yarn-fabric or textile with CNT or SP1-CNT.

The present inventors have prepared by PCR a polynucleotide encoding a chimeric SP1 polypeptide having a cysteine—for methionine substitution at amino acid residue 43 and a 6-amino acid deletion at the N-terminal (designated M43C ΔNSP1, SEQ ID NO: 1), and having an N-terminal silicon binding protein as in SEQ ID NO: 5 (mTB peptide), and have cloned and expressed the polynucleotide in bacteria. When the expressed chimeric SP1 protein was purified, it was uncovered that the chimeric SP1-silicon binding protein (mtbSP, SEQ ID NO: 3) associates into an SP1 oligomer which binds silica and silica dioxide with great affinity (see Example 2, FIGS. 7A-7C). The chimeric mtbSP oligomer is a ring shaped homo-dodecamer, presenting twelve silicon oxide binding peptides in its inner pore, six at each side of the ring (see, FIG. 4). The chimeric mtbSP1 polypeptide can bind to glass surfaces and fibers, and other materials containing silica compounds such as silicon carbide, silicon dioxide, titanium dioxide and the like, and can be used to modify the properties of such silicon containing materials. For example, the chimeric SP1 polypeptide can bind to carbon fiber coated with silane. Thin coating with silane is a common practice for many applications, for example, silanes are used as coupling agents to adhere carbon, glass and poly aramid fibers to a polymer matrix, and the chimeric mtbSP bind to such surfaces as a result of silane oxidation and silicon oxide formation on its surface.

Binding of the chimeric mtbSP1 polypeptide to silicon-containing surfaces and/or particles can be performed in a variety of conditions, as the SP1 chimeras are greatly resistant to denaturation in a variety of harsh conditions (heat, pH extremes, detergent and protease exposure). According to one embodiment of the invention, the binding is carried out at neutral or near neutral (pH 6.5) pH, in the presence of NaCl and a chaotropic agent, for example, guanidine hydrochloride or urea. As shown in FIGS. 6A and 6B, specific binding of the chimeric mtbSP1 polypeptide to silicon-containing surfaces is facilitated by the presence of 3M GuHCl.

The chimeric SP1 polypeptides of the present invention can also be used to bind carbon nanotube and/or graphite surfaces.

The present inventors have shown that, polynucleotides encoding chimeric SP1 polypeptide having an N-terminal carbon nanotube or graphitic surface binding protein as in SEQ ID NOs: 10-13 (CNT-binding peptides) were prepared by PCR, cloned and expressed in bacteria. When purified, it was uncovered that the recombinant chimeric SP1-carbon nanotube-graphitic surfaces binding proteins (L1-SP1CNT, L2-SP1-CNT, L3-SP1-CNT and L6-SP1-CNT, SEQ ID NOs: 6, 14, 8 and 15, respectively) associate into SP1 oligomers which bind carbon nanotubes and graphitic surfaces with great affinity (see Example 3, and Table 2). Crude extracts of the transformed bacteria expressing the chimeric SP1-CNT polypeptides also showed remarkably effective heat and protease-stable CNT affinity (see Table 3). In some embodiments, the chimeric SP1 polypeptides are expressed in bacteria as inclusion bodies. Chimeric SP1-CNT polypeptides, or chimeric SP1-CBD-CNT polypeptides, when expressed as inclusion bodies [L2 (SEQ ID NO: 14), L3 (SEQ ID NO: 8) and SP1-CBD (SEQ ID NO:86)] can be reconstituted by dissolution of the inclusion bodies in 6M urea and refolding of the protein by urea dilution with low ionic strength buffer, to yield chimeric SP1 polypeptides with CNT binding capability. In some embodiments, the refolded polypeptides are chimeric SP1 monomers. In yet other embodiments, the inclusion bodies are dissolved in Trisma base (20 mM), NaOH (8 mM), followed by high speed centrifugation to remove debris, and the supernatant diluted in water and pH adjusted to pH=8.2.

The present invention provides, in some embodiments thereof, the ability to weave carbon nanotubes into fabrics that may be applied to a wide range of uses. Carbon nanotubes with differing characteristics can be woven together to create unique fabrics. For example, carbon nanotubes that serve to electrically insulate can be combined or layered with highly electrically conductive carbon nanotubes to create garments that shield and protect the wearer from electric shock, while electrically conductive carbon nanotubes can be combined in fabric to protect against static buildup. Similarly, thermally conductive carbon nanotubes can be woven into materials that when tethered to a heat sink or source, serve to protect a user from intense thermal environments.

In general, the structural arrangement of the fabric exhibits the mechanical, thermal, electrical, physical and chemical properties associated with carbon nanotubes, and the SP1-modified CNT can be incorporated therein. As used herein, strands or "fibers" can be grouped together to define yarns. These yarns are then interwoven with one another and/or with companion yarns so as to define a fabric structure arrangement. According to other embodiments, the fibers-CNT composites, afforded due to mediation by SP1 variants, can be used to produce non-woven fabrics and sheets.

According to some embodiments of the present invention the chimeric SP1-CNT polypeptides can bind to multi-walled and single walled carbon nanotubes, carbon fibers and other materials containing carbon or graphite surfaces, such as carbon fibers and the like, and can be used to modify the properties of such carbon-containing materials. For example, the chimeric SP1 polypeptide can bind to carbon fibers before their incorporation into composite materials, to provide added strength, or can be used to bind carbon nanotubes to synthetic or natural fabrics and fabric precursors, such as aramid (Kevlar™) or cotton, in a uniform manner, to provide fibers and fabrics that have unique chemical, electrical, and thermal properties. Such fabrics and surfaces may comprise layers comprising carbon nanotube associated with certain polymeric substances and resins.

It will be appreciated, that increasing the electrical conductivity of a polymer, fabric or polymeric fabric can alter the electrostatic properties of the polymer, fabric or polymer fabric. Thus, low-static SP1 polypeptide-carbon nanotube-complexed polymer, fabric or polymeric fabrics can be used where electrostatic interaction and buildup in polymers, fabrics and polymeric fabrics is an important factor in the function of such materials. Thus, according to some embodiments of the instant specification, there is provided an electrically conductive fabric comprising a fabric substrate material comprising a SP1 polypeptide-carbon nanotube-complex bound thereto, wherein the conductivity of said electrically conductive fabric is greater than that of said fabric substrate material devoid of said bound SP1 polypeptide-carbon nanotube-complex. According to further embodiments of the invention, there is provided a method for manufacturing of a conductive polymer, fabric or polymeric fabric comprising the steps of: providing a fabric substrate material; preparing a composition of SP1 polypeptide-carbon nanotube-complex, and imparting conductivity to said polymer, polymeric fabric or fabric substrate material by treating said fabric substrate material with said composition of SP1 polypeptide-carbon nanotube-complex, and washing said fabric substrate material to remove of excess of said composition of conductive SP1 polypeptide-carbon nanotube-complex. In other embodiments, any of the methods of the present invention for binding carbon nanotubes to a fabric, yarn or polymer can be used to enhance the conductive properties of the fabric, yarn or polymer.

In some embodiments, the electroconductive fabric comprises a fabric substrate material selected from woven fabric and non-woven fabric, wherein said woven fabric and non-woven fabric is selected from natural fabric, synthetic fabric, a mixture of natural fabric and synthetic fabric, and inorganic material fabric. Exemplary fabrics or polymers include, but are not limited to of cotton, wool, and silk, said synthetic fabric is selected from the group consisting of nylon, polyester, aramid, polypropylene and elastane (Lycra™-Spandex™). Examples of garments, rope, sewn, molded and woven items fashioned from fabric and yarns comprising carbon nanotubes, suitable for manufacture using the SP1 polypeptide-carbon nanotube-complexed-polymer, fabric or polymeric fabric of the present invention include, but are not limited to parachutes, clothing, sleeping bags, bicycle parts and equipment, skis, etc (for further detailed examples, see U.S. Pat. No. 7,354,877 to Rosenberger et al., which is incorporated herein by reference).

Example 7 provided herein shows that the conductivity of an SP1 polypeptide-carbon nanotube-complexed-polymeric fabric is responsive to mechanical deformation (see Table 7). Thus, SP1 polypeptide-carbon nanotube-complexed-polymers, fabrics or polymeric fabrics of the present invention can also be used to manufacture or fashion fabrics or fabric-based products which are capable of altering their conductance in response to mechanical stress (pressure, tension, shear, impact, etc) applied to the fabric. Such fabric can be useful, for example, in designing sensors, interactive garments and the like. It will be appreciated that the SP1 polypeptide-carbon nanotube-complexed-polymeric fabric can be designed to be responsive to additional parameters, such as moisture (e.g. humidity), temperature, etc.

In one specific embodiment, SP1 and chimeric SP1 polypeptides are used to bind carbon nanotubes, and the resulting SP1 polypeptide-carbon nanotube-complex is then used to bind the carbon nanotubes to a polymer such as aramid (e.g. Kevlar™), for incorporation into rubber tires, in order to enhance the physical properties (e.g. electrical and/or thermal conductivity) and function of the tires.

As used herein, the phrase "SP1 polypeptide-carbon nanotube complex" refers to a composition comprising an SP1 or chimeric SP1 polypeptide, bound to at least one carbon nanotube, for example, as described in detail in Examples 1 and 3. As used herein, the phrase "SP1 polypeptide-carbon nanotube-polymer complex" refers to a composition comprising an SP1 or chimeric SP1 polypeptide, bound to at least one carbon nanotube, further bound to at least one polymer, polymer fiber or polymer fabric. In one embodiment, the SP1 polypeptide-carbon nanotube complex comprises multiwalled carbon nanotubes (MWCNT). In another embodiment, an SP1-CBD chimeric polypeptide is bound to the polymer, polymeric fabric or polymer fiber, and the SP1-carbon nanotube binds to the polymer, polymeric fabric or polymer fiber via the SP1-CBD chimeric polypeptide to form the SP1 polypeptide-carbon nanotube-polymer, polymer fabric or polymer fiber complex. It will be appreciated that such a complex can be formed from other substrates, such as yarn, wool, silk, cotton, and the like.

Thus, according to one aspect of the invention as claimed, there is provided a pneumatic or semi-pneumatic tire having a component which comprises at least one SP1 polypeptide-carbon nanotube complexed polymer, fabric or polymeric fabric. In one embodiment, the tire component is a composite elastomeric substance formed with said SP1 polypeptide-carbon nanotube-complexed polymer, fabric or polymeric fabric. In another embodiment, the tire component comprises layers of elastomeric substance and at least one layer of the carbon-nanotube-SP1-complexed polymer, for example, as in a reinforcement belt below the tread. In yet another embodiment, the tire component is selected from a sidewall, a tread base of a tread of cap/base construction and a tire apex.

Carbon-nanotube-complexed polymers can be incorporated into the basic matrix (e.g. rubber) of any portion of a tire, such as tread, sidewall, internal belts, bead, apex, etc. The polymer-matrix composite can be incorporated into the tire in different ways-entire elements of the tire may be fashioned from the carbon nanotube-complexed polymers, or polymer-matrix composite can be incorporated into the tire as layers, internal or external to the basic matrix of the tire. The composition of the polymer-matrix composite can be varied to suit the desired physical properties of the tire, or portion of the tire. For example, it can be advantageous to fashion the thinner sidewalls, not in contact with the road surface, from lower conductivity, carbon nanotube-polymer-poor matrix, while the thicker tread, and/or underlying reinforcement belts, can be constructed from high carbon-nanotube-polymer content matrix composite, imparting greater heat and electrical conductivity at the road-tire interface. Exemplary methods for producing aramid-rubber and aramid-rubber-carbon black composites suitable for use in tires are well known in the art, as detailed, for example, in US Patent Application 20040173295 to Zanzig et al.

Tires, and particularly automotive and aviation tires, having improved heat and electrical conductivity resulting from incorporation of SP1 polypeptide-carbon nanotube-polymer complexes of the invention into the tire matrix, can be more efficiently heated and cooled than conventional tires, for example, by applying an appropriate electrical current to the conductive elements of the tire.

Thus, according to one aspect of the invention as claimed, there is provided a method of altering the electric charge of an automotive tire, comprising obtaining a tire having at least one of a sidewall, tread base of a tread of cap/base construction and tire apex which comprises at least one SP1 polypeptide-carbon nanotube-complexed polymer, fabric or polymeric fabric, and applying an electric current to said at least one SP1 polypeptide-carbon nanotube-complexed polymer, fabric or polymeric fabric, thereby altering the electric charge of said automotive tire. In one embodiment, altering the electric charge of the tire increases the temperature of the tire. In one embodiment, the tire is mounted on a rim or wheel, and altering the electric charge of the tire is effected while the tire is at rest. In another embodiment, the tire is mounted on a wheel or rim, and altering the electric charge is effected while the tire is rotating. Methods for providing an electric current to a tire, or tire component, while rotating are well know in the art, and include, for example, electrical connection via the wheel, brush contacts implanted in the tire, and the like.

Such a method for altering the temperature of the tire or tire component can be useful in preparing a resting tire for use, for example, warming a tire of a racing vehicle to a desired temperature for optimum performance during acceleration and motion of the vehicle. Tire temperature is a particularly critical parameter, for example, in auto and motorcycle racing. Yet further, tire temperature is critical in aviation, particularly in tires of aircraft landing gear, which are exposed to extremely low temperatures until very shortly before their use during landing. Efficient, uniform and rapid warming of the tires of landing gear before touchdown, according to the methods of the present invention, can not only improve tire performance and reduce weight requirements, but may also result in greater safety from tire failure. Temperature control in aircraft tires can also be advantageous in improving performance and safety during take-off and taxiing of the aircraft.

It will be appreciated that the SP1 polypeptide-carbon nanotube-complexed polymer, fabric or polymeric fabric can be designed in order to provide a cooling effect upon application of an electric current, according to the Peltier effect. Thus, in yet another embodiment, altering the temperature of the tire can be cooling the tire.

Thus, there is provided a method for racing a vehicle, the vehicle having tires which comprise at least one SP1 polypeptide-carbon nanotube-complexed polymer, fabric or polymeric fabric, the method comprising providing an electric current to said at least one SP1 polypeptide-carbon nanotube-complexed polymer, fabric or polymeric fabric, so as to change the temperature of said tire to a desired temperature, and racing said vehicle having tires of said desired temperature.

Yet further embodiments of the invention as claimed include, but are not limited to, tires having at least one SP1 polypeptide-carbon nanotube-complexed polymer, fabric or polymeric fabric element forming a conductive path for discharging static electric charge buildup (for details of construction of such tires, see, for example, US Patent Application 2010078103, to Nakamura, U.S. Pat. No. 7,528,186 to Halas a, U.S. Pat. No. 7,284,583 to Dheur et al and U.S. Pat. No. 7,131,474 to Sandstrom), tires having at least one SP1 polypeptide-carbon nanotube-complexed polymer, fabric or polymeric fabric element having improve thermal conductivity and heat transfer to the road during use (for details of construction and use of such tires, see, for example, U.S. Pat. No. 7,337,815 to Spadone), tires having at least one SP1 polypeptide-carbon nanotube-complexed polymer, fabric or polymeric fabric element capable of communicating information on tire status and performance, such as tire pressure, deformation, tread and sidewall wear and failure, rolling resistance, etc. at rest and in motion, during use (for details of construction and use of such tires, see, for example, U.S. Pat. No. 7,318,464 to Hahn et al and U.S. Pat. No. 7,581,439 to Rensel, et al.) and electrical energy generating tires with a conductive strip of a carbon-nanotube-SP1-complexed polymer, fabric or polymeric fabric, and an energy generating component (such as a piezoceramic or thermal-harvesting material) incorporated into the tread and/or sidewall of the tire ((for details of construction and use of such tires, see, for example, U.S. Patent Application 0070028958 to Retti and U.S. Patent Application 0090314404 to Rodgers et al).

In some applications, it is desirable that a material incorporating a conductive polymer exhibit anisotropic properties, i.e. non-uniform conductivity, such as a gradient of decreasing conductivity in a particular direction.

In some embodiments, the chimeric SP1 polypeptides interact with the target inorganic substances, or with the chemical environment via a reversible or covalent bond or molecular association. As used herein the phrase "bond" or "molecular association" refers to a chemical association or a physical association or both, which takes place on a molecular level. For example, a bond or association can be a covalent bond, a non-covalent bond, a hydrophobic interaction, etc.

In some embodiments, the chimeric SP1 polypeptides interact with the target inorganic substances, or with the chemical environment via a reversible or covalent bond or molecular association. As used herein the phrase "bond" or "molecular association" refers to a chemical association or a physical association or both, which takes place on a molecular level. For example, a bond or association can be a covalent bond, a non-covalent bond, a hydrophobic interaction, etc.

A "reversible association" or "reversible bond" as defined herein, is an association wherein the components can return to an original, pre-association, state, and reassociate, depending on the specific conditions. Preferably such association and reassociation does not include the formation and cleavage of peptide bonds. For example, a reversible bond of the components of a modified SP1 chimeric polypeptide-inorganic substance complex of the invention can disassociate and thereby return to original and distinct inorganic substance and SP1 chimera components.

Types of reversible molecular associations or bonds suitable for use in the present invention are associations selected from the group consisting of electrostatic bonding, hydrogen bonding, van der Waals forces, ionic interaction or donor/acceptor bonding. The reversible association can be mediated by one or more associations between the substance and the SP1 polypeptide. For example, the reversible association can include a combination of hydrogen bonding and ionic bonding between the complexing substance and the SP1 polypeptide. Additionally, or alternatively, the reversible association can be in combination with, for example, covalent or other noncovalent interactions between components, such as between a substance and an SP1 polypeptide or chimeric polypeptide.

The chimeric SP1 polypeptides and compositions of matter comprising the same have been shown to enhance dispersal of bound inorganic substances in solvent. For example, normally highly insoluble carbon nanotubes were found to disperse with up to 1000-fold greater concentration in both aqueous and organic environments when complexed with a chimeric, carbon nanotube-binding L1 SP1 (see Examples 3 and 4 hereinbelow). As used herein, the term "dispersion" refers to the ability of a solute or a colloid to be evenly distributed and/or dissolved in a solvent, in order to form a solution or suspension comprising the solvent and solute. It will be appreciated that all solutes are, in theory, soluble in all solvents. However, poorly or negligibly soluble (immiscible) solutes or colloids do not form solutions or suspensions of any significant concentration with given solvents.

Thus, as used herein, "enhancing the dispersion" refers to increasing the concentration of said substance, as a solute or colloid, in a solution or suspension with a solvent. In a preferred embodiment, the substance is a hydrophobic substance, typically insoluble or poorly soluble in water, and the solvent is an aqueous solvent.

The stability of chimeric SP1 polypeptides oligomeric complexes to boiling, protease digestion and pH extremes is shown in Examples 2, 3 and 4, and FIGS. 2A-2B and 5A-5B hereinbelow. When L1-SP1 chimera was combined with carbon nanotubes in solution, washed and filtered to remove any free L1 SP1 and unbound carbon nanotubes, dried and reconstituted in aqueous solvent, molecular association and complex formation between L1-SP1 and the carbon nanotubes rendered the carbon nanotubes highly dispersable in water even under heat and high pHs (see Example 3 hereinbelow). Further, the chimeric SP1-carbon nanotube complex can be easily dried under heat and stored, and reconstituted in a variety of solvents, such as monomer solutions prior to polymerization (see Example 4 hereinbelow).

Chimeric SP-1 polypeptides complexed with target inorganic substances can be added to polymers in a variety of methods. In some embodiments, the complex of chimeric SP1 and target substance (for example, L1-SP1-carbon nanotube complex) is prepared by extensive sonication, washed and filtered, and concentrated by ultrafiltration dialysis. The resulting concentrated complex is dehydrated by freeze-drying to a fine powder, which is then vigorously mixed with the monomer solution (for example, epoxy), followed by sonication and centrifugation to remove undispersed SP1-target substance complexes. Alternatively, the complex of chimeric SP1 and target substance (e.g. carbon nanotubes) is prepared by extensive sonication, the solution adjusted to alkaline pH (approx pH 12) with NaOH, and precipitation of the chimeric SP1-target substance in 50% ethanol at −20° C., centrifugation and mixing with the monomer solution as described. Concentration of the dispersed inorganic substance in the monomer solution can be measured by changes in optical density (transmission or absorbance) due to the suspension of the inorganic substance, or, optionally, by measurement of the protein concentration in the suspension (due to the addition of the chimeric SP1 complexes). Functional parameters can also be evaluated.

According to some embodiments of the present invention, there are provided compositions of matter comprising a chimeric SP1 polypeptide of the present invention, having an inorganic substance binding peptide component, and the target inorganic substance. Such a composition of matter can include, in some embodiments, for example, L1SP1 chimera (SEQ ID NO: 6) bound to carbon nanotubes, mtbSP (SEQ ID NO: 3) bound to silicon surfaces or silicon dioxide beads, L1SP1 (SEQ ID NO: 6) bound to carbon fibers, and the like. In view of the bi- and multi-functional properties of the chimeric SP1 oligomers, some compositions of matter of the present invention can further comprise additional molecules or substances such as polymers. Thus, for example, a composition of matter according to some embodiments can comprise a chimeric SP1 polypeptide or oligomer bound to carbon nanotubes, dispersed in, for example, an epoxy polymer (see Example 4 hereinbelow). Superior and more uniform dispersion in the epoxy solution of carbon nanotubes by chimeric SP1 before polymerization results in a carbon nanotube-modified epoxy polymer of high CNT density, evenly dispersed, without opacity. Such a liquid epoxy-chimeric SP1-carbon nanotube composition of matter can be hardened by polymerization and used to coat and alter physical properties (e.g. conductivity) of surfaces, molded into forms, cast and tooled into desired shapes and the like.

Thus, in some embodiments of the present invention, there is provided a composition of matter comprising a first inorganic substance complexed with a modified SP1 polypeptide dodecamer and a second inorganic substance complexed with the modified SP1 polypeptide dodecamer, wherein the first and second inorganic substances are complexed via a first and a second binding region of the SP1 dodecamer. In some embodiments the modified SP1 polypeptide is a chimeric SP1 polypeptide comprising a heterologous inorganic substance binding peptide, such as mtbSP1, L1-SP1, L6-SP1, L3-SP1 and the like. In further embodiments the modified SP1 are complexed with the first and second inorganic substances by a non-covalent bond. In yet other embodiments, the first and/or second inorganic substances are complexed with the modified SP1 by a covalent bond.

The composition of matter of the present invention can comprise a hetero-complex SP1 oligomer, comprising non-identical SP1 monomers, or a homo-complex SP1 oligomer comprising identical modified SP1s or SP1 chimeras. In some embodiments of the present invention the first inorganic substance is a carbon nanotube and the second inorganic substance is a polymeric fiber. In other embodiments the first binding region is a carbon nanotube binding region (for example, any of SEQ ID NOs:10-13) and the second binding region is a silicon binding region (for example, SEQ ID NO:5).

Binding of the chimeric mtbSP1 polypeptide to silicon-containing surfaces and/or particles can be performed in a variety of conditions, as the SP1 chimeras are greatly resistant to denaturation in a variety of harsh conditions (heat, pH extremes, detergent and protease exposure). According to some embodiments of the invention, the binding is carried out at neutral or near neutral (pH 6.5) pH, in the presence of NaCl and a chaotropic agent, for example, 3M guanidine hydrochloride.

In some embodiments, function of chimeric SP1 polypeptides of the present invention can be altered by solvent conditions. Exposure to chaotropic agents, such as GuHCl, can produce conformation changes in the SP1 oligomer, enhancing the binding avidity of the inorganic binding peptide components for their target molecules. Such effect of chaotropic agents, for example, affords superior specificity of complex formation and flexibility of use of the chimeric SP1 polypeptides of the invention. As shown in FIGS. 6A and 6B, specific binding of the chimeric mtbSP1 polypeptide oligomer to silicon-containing surfaces is facilitated by the presence of GuHCl. Thus, according to some aspects of the invention, there is provided a method of enhancing binding of a substance to an SP1 dodecamer or oligomer, comprising contacting the substance with the SP1 oligomer or dodecamer in the presence of a chaotropic agent. A non-exhaustive list of chaotropic agents suitable for use with the method of the invention includes guanidinium hydrochloride, lithium perchlorate and urea.

As used herein, a "chaotropic agent" is defined as a substance which disrupts the three dimensional structure in macromolecules such as proteins, DNA, or RNA and denatures them.

The chimeric SP1 polypeptides can be provided along with the chaotropic agents. Thus, according to some embodiments of the invention, there is provided a composition of matter comprising an SP1 dodecamer which comprises at least one SP1 polypeptide having a modified amino acid sequence capable of binding a substance, said modified amino acid sequence being located at a region of said SP1 polypeptide corresponding to the central cavity region of an SP1 dodecamer, wherein said binding of said substance is enhanced in the presence of a chaotropic agent, wherein the composition of matter further comprises the chaotropic agent. As described herein, the chaotropic agent affords control over binding characterisitics of the modified SP1 dodecamer, and providing the SP1 dodecamer along with the chaotropic agent imparts, for example, highly selective binding to target inorganic molecules. For example, the dodecamer of chimeric polypeptide mtbSP1 can be mixed with GuHCl 6M for greater silicon binding avidity, as described below.

In some embodiments, the amino acid sequence modification does not include a Ni-binding His tag. In other embodiments, the amino acid sequence modification does not include a Ni-binding His tag when the chaotropic agent is guanidinium hydrochloride. In yet further embodiments, the amino acid sequence modification does not include a Ni-binding peptide. In still further embodiments, the amino acid modification does not include a His tag.

In some embodiments of the invention, the chimeric SP1 polypeptides and chimeric SP1-inorganic substance complexes of the present invention can useful as, for example, molecular linkers, for surface coating of any inorganic target compounds and/or molecules binding and complexing with the chimeric SP1 oligomers, nanocircuitry using conducting molecules or semiconductor target substances, and the like. In some embodiments, the chimeric SP1 polypeptides or chimeric SP1-target substance complex of the present invention can be incorporated as a component of a conductive device such as an electronic device.

The present invention therefore provides, though some of its embodiments and combinations thereof, the possibility to form new composite materials and improve the production of known composite materials, by affording the dispersion of inorganic substances, such as carbon nanotubes, in other substances, such as polymeric resins, and allowing one or both substances to undergo a chemical reaction, even under harsh conditions, to form the composite material. The SP1 variant(s) can withstand most harsh reaction conditions while still remaining bound to the dispersed substance thereby enhancing its dispersibility in the resin, while the resin undergoes polymerization reaction and hardens to form fibers, yarns, strips or films.

For example, the dispersing media (resin) is a liquid-state thermosetting polymer. Exemplary thermosetting polymers include, but are not limited to phenolic resin, epoxy resin, aromatic polyamide (aramid) resin (such as KEVLAR™), bismaleimide resin, triazine resin, polyimide, and polymethyl methacrylate. Other reagents, hardeners and co-polymers are selected from a group consisting of aliphatic amine, aliphatic cyclic amine, aromatic amine, polyamide, acid anhydride, tertiary amine, and any combination thereof, and are ultimately used to accelerate the process of solidifying the liquid-state thermosetting polymer.

Other composite material modifying reagents include, but are not limited to polysulphide rubber, polyamide resin, acrylonitrile rubber, and any combination thereof, and are ultimately used to improve the property of the liquid-state thermosetting polymer.

Exemplary diluting agents which also modify the chemical and mechanical properties of the composite material include, but are not limited to diglycidyl ether, polyglycidyl ether, butyl epoxy propyl ether 660, allylphenol, and any combination thereof.

Fillers reagents, which add functionality to the composite material are selected from the group which includes, but is not limited to asbestos fiber, glass fiber, quartz powder, aluminum oxide, and any combination thereof, and are ultimately used to, for example, improve the heat-dissipation of the liquid-state thermosetting polymer.

Methods of preparing composite materials using SP1 variant-carbon-nanotube complexes include, but are not limited to contacting the SP1 variant-carbon-nanotube complex with a polymer under conditions sufficient to form a carbon-nanotube composite, wherein the polymer is deposited on the SP1 variant-carbon-nanotube complex. In one embodiment, the polymer is dissolved in a solvent to form a solution, and a SP1 variant-carbon-nanotube-bound substrate is dipped into the solution to form a polymer coated nanocomposite material. The solvent used can be water, common organic solvents or a mixture thereof. Non-limiting exemplary organic solvents include less polar hydrocarbon solvent, such as pentanes, hexanes, petroleum ether, benzene and toluene; and polar solvents, such as ether, tetrahydrofuran, dichloraomethane, chloroform, dichloroethane, dimethysulfoxide, dimethylformamide, dimethylacetamide, dioxane, methanol, ethanol, ethyl acetate, acetonitrile, acetone and carbon tetrachloride. In another embodiment, the SP1 variant-carbon-nanotube complex is mechanically blended with the polymer. In yet another embodiment, the SP1 variant-carbon-nanotube complex is mixed with the polymer under a melt-processing condition. Various techniques are suitable for the formation of nanocomposite materials. These include injection molding, extrusion, blow molding, thermoforming, rotational molding, cast and encapsulation and calendaring. The polymers used in the melt-processing are preferably thermoplastic polymers. In still another embodiment, the composite is formed by conducting the polymerization in the presence of a SP1 variant-carbon-nanotube complex.

Both naturally occurring polymers and synthetic polymers and/or copolymers can be used for the preparation of carbon-nanotube composites. Naturally occurring polymers include, but are not limited to, natural rubber, proteins, carbohydrates, nucleic acids. Synthetic polymers include condensation polymers and addition polymers, which can be either thermoplastic or thermoset polymers. Thermoplastic condensation polymers include, but are not limited to, polysulfones, polyamides, polycarbonates, polyphenylene oxides, polysulfides, polyether ether ketone, polyether sulfones, polyamide-imides, polyetherimides, polyimides, polyarylates, and liquid crystalline polyesters. Non-limiting exemplary thermoplastic polyolefins include polyethylene, polypropylenes, polystyrenes, polyvinyl chloride, polyacrylates, polymethacrylate, polyacrylamide, polymethacrylamide, polyacrylonitrile, poly(N-vinylcarbazole), poly(N-vinylpyrrolidine), poly(vinyl ether), polyvinyl alcohol), poly (vinylidene fluoride) and polyvinyl fluoride).

Since the chimeric SP1 variants are designed to interact and bind with more than one substance at once, such as silicon and CNT/graphite, or gold and CNT/graphite, these variants may serve as a basis for the formation of composite materials which also possess controllable conductivity and semi-conductivity stemming from one or both types of bound substances. Such composite materials can be used for a variety of application in the micro-electronic field.

It is expected that during the life of a patent maturing from this application many relevant methods and compositions comprising modified SP1 proteins and their use will be developed and the scope of the terms modified SP1 protein of the invention is intended to include all such new technologies a priori.

As used herein the term “about” refers to ±10%.

The terms “comprises”, “comprising”, “includes”, “including”, “having” and their conjugates mean “including but not limited to”.

The term “consisting of means “including and limited to”.

The term “consisting essentially of” means that the composition, method or structure may include additional ingredients, steps and/or parts, but only if the additional ingredients, steps and/or parts do not materially alter the basic and novel characteristics of the claimed composition, method or structure.

As used herein, the singular form “a”, “an” and “the” include plural references unless the context clearly dictates otherwise. For example, the term “a compound” or “at least one compound” may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases “ranging/ranges between” a first indicate number and a second indicate number and “ranging/ranges from” a first indicate number “to” a second indicate number are used herein interchangeably and are meant to include the first and second indicated numbers and all the fractional and integral numerals therebetween.

As used herein the term “method” refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term “treating” includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate some embodiments of the invention in a non limiting fashion.

General Experimental Concept

The studies presented below demonstrate two strategies for altering the binding properties of SP1 variants, namely the affinity and avidity of SP1 variants to various substrates and controlling the immobilization of SP1 on various surfaces. Affinity and avidity are two terms used in protein biochemistry to describe strength of non covalent interactions, the phenomenon whereby certain atoms or molecules have the tendency to aggregate or bond.

The term "affinity" is used to describe the strength of a single bond, while the term "avidity" is use to describe the combined strength of multiple bond interactions affinity. Dissociation constant (Kd), or equilibrium constant, is the inverse of the affinity constant, measures the propensity of a larger object to separate (dissociate) reversibly into smaller components, as when a complex falls apart into its component molecules, or when a salt dissociates into its component ions. The dissociation constant is usually denoted Kd and is the inverse of the affinity constant. In the special case of salts, the dissociation constant can also be called the ionization constant.

The first strategy involves positioning of the anchoring side-chains, such as found in cysteine residues, on the dodecameric protein's ring rim, and comparing the binding properties of the resulting construct with those of a protein construct having anchoring side-chains positioned at the inner side of the annulus (the pore or "hole" of the ring). This strategy uncovers the capacity of the SP1 basic architecture to protect certain regions on its surface, and ligands attached thereat, from surface exposure.

In the second strategy, several binding moieties are attached to the SP1 dodecameric protein at the protein's annulus inner pore by genetic engineering. By fusing these specific affinity peptides at a putative protected part of the protein, the binding moieties are expected to be less available for binding with large entities which are excluded from the protein's pore. This experimental strategy is designed to study the effect of changing the conditions of the media of the protein, and to show that entering a factor to the media, which can affect the structure of the SP1 monomers and thus the structure of the entire dodecamer, can control the degree of exposure of the binding moieties to the media. The event of adding the structure altering factor, such as a denaturating agent, can thus increase the ability of the binding moieties to interact and bind large entities in the media. The capacity to switch from a non-binding entity to a binding entity by adding and removing a chemical factor constitutes a chemical switch.

The concept of a chemical switch was demonstrated by fusing several specific affinity peptides, such as silicon binding peptides, to each of the SP1 basic skeleton, at inner pore position, to thereby obtain a silicon binding protein switch, which is sensitive to the media levels of denaturating agents, such as guanidinium hydrochloride (GuHCl). The affinity peptide was isolated by Sano and coworkers [Sano, K. I. et al. *JACS.* 125, pp 14234-14235, 2003; Sano, K. I et al., *JACS,* 128, pp 1717-1722, 2006; and Sano, K. I. et al., *Nano Lett.,* 7, pp 3200-3202, 2007] using a peptide-phage display system. This six amino acids peptide, referred to herein and in the art as mTBP, was reported by Sano and coworkers to bind to Ti, Ag and Si surfaces, but not to Au, Cr, Pt, Sn, Zn, Cu, or Fe.

Thus, a SP1 scaffold was modified to present 12 copies of the mTBP hexapeptide in a switchable manner. A positive cooperative effect is demonstrated when the peptide is presented on the SP1 dodecamer, as compared to the free peptide, accompanied with significant reduction in non-specific binding of the fused peptides compared to that of the free peptide.

Construction of SP1 Variants with High Affinity to Various Materials

WO 2007/007325 provides a non-limiting list of peptides forming complexes with inorganic ionic substances, adapted from Sarikaya et al. [*Ann. Rev. Mater. Res.,* 2004, 34, 373-408]. These relatively short peptides are suitable for fusion to the SP1 protein as part of the modification of the SP1 polypeptide. Many more examples of peptides with high affinity to different materials are disclosed in the literature.

Table 3 presents the SP1 variants used in this context, their binding ability, primers used for their construction, mutation or insertion at the N-terminus, SP1 template, reference, and growth conditions/induction. All mutant proteins demonstrated characteristics similar to the wild type SP1 in terms of heat stability, protease resistance and complex formation. Standard nomenclature of mutations is used i.e., amino acids position using wild type sequence including first methionine residue.

TABLE 3

| SP1 variant/ Relevant activity | PCT Primers | Mutation and/or Insertion at the N-terminus | SP1 Template and reference | Growth conditions/ induction |
|---|---|---|---|---|
| Wild type SP1 (SEQ ID NO: 4) | | | U.S. Patent Application No. 2006/0172298 | Terrific broth or Luria broth/ 37° C./ IPTG 1 mM |
| Δ2-6 (SEQ ID NO: 64) | | Δ2-6 | Wang et al. (2006); WO 2007/007325 | Luria broth/ 37° C./ IPTG 1 mM |
| M43C Δ2-6 (SEQ ID NO: 1) | 5' CTGCTCGATCTCATTCCAAGCTGTA AGAGTTTCAATTGGGGCACG 3' (SEQ ID NO: 65) | M43C Δ2-6 | Δ2-6 | Luria broth/ 37° C./ IPTG 1 mM |
| L81C Δ2-6 Flat gold binding (SEQ ID NO: 2) | 5' GCAAGTCTGGTTTGCAAGAGTA CTGCGATTCTGCTGCTCTTGCTG 3'. (SEQ ID NO: 66) | L81C Δ2-6 | Δ2-6 | Luria broth/ 37° C./ IPTG 1 mM |
| mtbSP Switchable silicon oxide binding CNT dispersion (SEQ ID NO: 3) | 5'-AAAACATATGCGC AAACTTCCGGATGCG GCAACCAGAACTCCAAAGCTTG-3' (SEQ ID NO: 67) and SP1rev 5' AAAAGAGCTCTTAGT AAAGAAAGTAATCAATAAC-3') (SEQ ID NO: 68) | RKLPDAA (SEQ ID NO: 5) | M43C Δ2-6 Medalsy et al. (2008); WO 2007/007325 | Terrific broth or Luria broth/ 37° C./ IPTG 1 mM |
| L1-SP1 CNT dispersion (SEQ ID NO: 6) | 5' AAGGAGATATACAAAAACATATG CACTGGTCAGCATGGTGGATACG ATCAAATCAATCAGCAACCAGAA CTCCAAAG 3' (SEQ ID NO: 70) 5' CTTTGGAGTTCTGGTTGCTGATTG ATTTGATCGTATCCACCATGCTGA CCAGTGCATATGTTTTTGTATATC TCCTT 3' (SEQ ID NO: 71) | HWSAWWIR SNQS (SEQ ID NO: 10) | Wild type | Terrific broth/ 28° C./ IPTG 1 mM |
| L2-SP1 CNT dispersion (SEQ ID NO: 14) | 5' AGAAGGAGATATACAAAAACAT ATGCACTCATCATACTGGTACGCA TTCAACAACAAAACAGCAACCAG AACTCCAAAGC 3'(SEQ ID NO: 72) 5' GCTTTGGAGTTCTGGTTGCTGTTT TGTTGTTGAATGCGTACCAGTATG ATGAGTGCATATGTTTTTGTATAT CTCCTTCT 3'(SEQ ID NO: 73) | HSSYWYAF NNKT (SEQ ID NO: 11) | Wild type | Terrific broth/ 37° C./, IPTG 0.1 mM |
| L3-SP1 CNT dispersion Aramid (Kevlar) binding (SEQ ID NO: 8) | 5' ATACAAAAACATATGGATTATTT TTCATCACCATATTATGAACAATT ATTTGCAACCAGAACTCC 3' (SEQ ID NO: 74) 5' GGAGTTCTGGTTGCAAATAATTG TTCATAATATGGTGATGAAAATA ATCCATATGTTTTTGTAT 3 (SEQ ID NO: 75) | DYFSSPYYE QLF (SEQ ID NO: 12) | Wild type | Terrific broth/ 37° C./ IPTG 0.5 mM |
| L6-SP1 CNT dispersion (SEQ ID NO: 16) | 5' AGAAGGAGATATACAAAAACAT ATGTCAAATCAATCAGCAACCAG AACTCCAAAGC 3'(SEQ ID NO: 76) 5' GCTTTGGAGTTCTGGTTGCTGATT GATTTGACATATGTTTTTGTATAT CTCCTTCT 3 (SEQ ID NO: 77) | SNQS (SEQ ID NO: 13) | Wild type | IPTG 1 mM/ 37° C./Terrific broth |

CNT = carbon nanotubes;

L81C SP1 (SEQ ID NO: 2) variant is expressed as inclusion bodies IBs. The IBs were washed first for 15 minutes with IB washing buffer (20 mM Tris HCl, 2 M urea, pH 8) and then centrifuged at 14000 g for 15 minutes. The pellets were resuspended in denaturation buffer (20 mM Tris HCl pH 8, 6 M urea, 10 mM dithiothreitol) and diluted to a protein concentration of 5 mg/ml. Denatured proteins were then refolded by dialysis against 20 mM Tris HCl pH 7, 1 mM DTT, for 4 days.

Binding of a SP1 Variants to Gold Surface

Protein gold labeling through cysteine amino acids is a well known technique. An SP1 variant deleted of its N-terminus was used to prevent interference from the N-terminus, ΔNSP1 (SEQ ID NO: 64). Cysteine residues were introduced to the protein (see, Table 1) either in the central cavity or in the rim, M43C and L81C, respectively. The binding affinity of the two mutants to ultra-flat gold surfaces was determined by dynamic mode atomic force microscopy (AFM) topographic imaging (Dulcinea microscope, Nano-Tec, Madrid) and flooding image analysis technique was used to determine the surface coverage of the new mutants.

Binding of a SP1 Variants to Silicon Oxide Surface Fusion of the silicon binding peptide (RKLPDAA, SEQ ID NO: 5, Nano Lett., 2007, 6, 1579-1579) to the N-terminus of M43C ΔNSP1, yields the variant mtbSP1 (SEQ ID NO: 3) (see, Table 1 and Table 2). SDS-PAGE analysis of the mtbSP silica binding, discussed hereinbelow, showed that the mtbSP1 variant binds to silica beads while the wild type SP1 does not. Fusion of 12 copies of these peptides to SP1 N-terminus was expected to yield higher binding ability as compared to the free peptide as a result of higher binding avidity, provided that the fused binding peptide is exposed and accessible to the substrate. It was suggested that GuHCl, a chaotrophic (protein denaturing) agent, will allow certain flexibility to N-termini of the highly stable SP1 complex and consequently expose the silicon binding peptide, thereby facilitating its binding to the silica. The apparent dissociation constant for both mtbSP and the free peptide were determined, as presented hereinbelow. The mtbSP1 variant demonstrated a much lower Kd value (0.3 μM) than the free peptide (86 μM), as presented hereinbelow, meaning that when the peptide is presented on the SP1 scaffold, its affinity to the silica is increased by 2-3 orders of magnitude.

Carbon Nanotubes (CNT) Dispersion by SP1 Variants

The Examples presented below provide SP1 variants, fused to CNT-binding peptides, which are capable of binding to CNT and thereby enable the aqueous dispersion of these protein-coated CNT. Several examples of short peptides that were isolated from phage display libraries as CNT-binding peptides are disclosed in the literature. See, for example, Nature materials, 2003, 2, 196; Nano lett., 2006, 6, 40-44; and Langmuir, 2004, 20, 8939-8941).

The plasmid construction, expression and production the SP1 variants with N-terminus fusion used for CNT dispersion experiments are describes Table 1 above.

Table 4 below presents the terminus sequence of these variants, as well as their purification method and grade, N-terminal sensitivity to digestion by alcalase, and the SP1 variant concentration which is required for CNT dispersion. All mutant proteins demonstrated characteristics similar to the wild type SP1 in terms of heat stability, protease resistance and complex formation. Shift in molecular weight relatively to samples that were not treated with alcalase was observed both in samples that were not boiled or boiled in SDS gel application buffer (complex and monomer, respectively). In all cases the apparent molecular weight of the alcalase treated SP1 variants was higher than those of wild type, indicating that some but not all the added amino-acids were removed, and they are different from published sequences.

TABLE 4

| SP1 variant | Peptide fused to the N-terminus | Grade | SDS PAGE analysis Complex Formed | N-terminal sensitivity to digestion by alcalase | SP1 concentration required for CNT dispersion (mg/ml) | References |
|---|---|---|---|---|---|---|
| Wild type | None | 80° C. plus alcalase treatment | Yes | No | 1 | |
| | | Ion exchange purified protein | Yes | | <1 | |
| mtb SP | RKLPDAA (SEQ ID NO: 5) | 80° C. treatment | Yes | No | 0.2 | U.S. Application No. 20070112174 |
| | | Ion exchange purified protein | Yes | | 0.1 | U.S. Application No. 20070117148 Nano Lett., 2007, 6, 1579-1579. |
| L1-SP1 | HWSAWW IRSNQS (SEQ ID NO: 10) | 80° C. plus alcalase treatment | Yes | Yes | 0.004 | U.S. Patent No. 7,304,128 U.S. Application No. 20070117147 |
| | | Ion exchange purified | Yes | | 0.004 | U.S. Application No. 20070117150 |
| | | Ion exchange purified plus alcalase treatment | Yes | | 0.004 | U.S. Application No. 20070117148 U.S. Application No. 20040058457 Nature Materials, 2003, 2, 196 |
| L2-SP1 | HSSYWY AFNNKT (SEQ ID NO: 11) | 80° C. plus alcalase treatment | Yes | Yes | 0.04 | U.S. Application No. 20060172282 |
| | | Dissolved inclusion bodies | No | Complete digestion | 0.100 | Nano Lett., 2006, 6, 40-44 |
| | | Refolding of IBs | Yes | Yes | 0.1 | |
| L3-SP1 | DYFSSP YYEQLF (SEQ ID NO: 12) | Refolding of IBs | Yes | Small shift | 0.1 | U.S. Application No. 20050277160 Langmuir, 2004, 20, 8939-8941 |
| | | 80° C. plus alcalase treatment | Yes | Small shift | 0.01 | |
| L6-SP1 | SNQS (SEQ ID NO: 13) | 80° C. plus alcalase treatment | Yes | No | 0.05 | |

Surprisingly, treatment with alcalase and partial digestion of the N-terminus doesn't reduce its ability to disperse CNT. This is probably because in each complex not all N-termini are digested and the L1 variant (SEQ ID NO: 6) complex appears as a double band. For example, N-terminus sequencing and MALDY-TOF analysis of alcalase treated L1-SP1 revealed that 8 amino acids were digested by the protease and the N-terminus was SNQS but the digestion doesn't reduce its ability to disperse CNT. In agreement with this conclusion insertion of the SNQS peptide to SP1 N-terminus yields a variant, L6 (SEQ ID NO: 15), with lower CNT dispersion activity, lower than L1 (SEQ ID NO: 6) (50-100 μg/ml versus 4 μg ml, respectively).

Tri-Complexes of SP1 Variants, CNT and Aramid (KEVLAR™) or Epoxy Resin

The capacity of the SP1 variants of the present embodiments to disperse CNT in other media, such as Epoxy resin, and to bind to advanced materials, such as KEVLAR™, was studied and demonstrated, as presented in detail hereinbelow.

SP1 variants were studied for their capacity as multifunctional reagents which can bind CNT through the N-terminus to form a SP1/CNT complex, which in turn can bind to epoxy resin through exposed primary amines. Such reagents can be highly useful in many practical applications involving water interfaces with CNT, including dispersion in epoxy resin. While water and other mediating solvents can be removed by combination of ultra filtration and freeze drying, these processes are energy consuming and hard to control. The process presented herein takes advantage of the fact that SP1 precipitates in the presence of 70-80% ethanol after 2 hours incubation at −20° C., and so does the CNT protein complex. The precipitated SP1/CNT complex can be easily dispersed in water. The freeze-dried precipitated SP1/CNT complex can be dispersed in epoxy resin as demonstrated below (see Example 4).

In addition, it was hypothesized that if CNT and aramid (e.g. KEVLAR™—a brand name of a strong and heat-resistant aramid fiber developed by DuPont and used in bullet-proof vests, tires, fiber-optic cables and more) bind to SP1 variants in a similar fashion, the protein may serve as an adhesive mediator to promote attachment of these two components to each other, based on the two-sided doughnut shape of SP1 which exhibits binding sites on both sides of the annulus.

Materials and Methods

Bacterial Strain and Culture Conditions:

*Escherichia coli* strain DH5α was used for cloning and *E. coli* strain BL21 (DE3) was used for expression. Cells were grown in either Luria Bertani medium (ΔNSP1, M43CΔNSP1 and L81CΔNSP1), Terrific broth (L1-SP1, L2-SP1, L3-SP1, L6-SP1), or either Luria or Terrific broth interchangeably (native SP1, mtbSP), at 37° C. (except for L1-SP1, which was grown at 28° C.). After induction with isopropyl β-D-thiogalactopyranoside (IPTG)(1 mM for native SP1, mtbSP1, ΔNSP1, M43CΔNSP1, L81CΔNSP1, L1-SP1 and L-6 SP1, 0.5 mM for L3-SP1 and 0.1 mM for L2-SP1) bacteria were grown for additional 4 hours, followed by harvesting by centrifugation at 14,000×g for 15 minutes.

Vector Construction:

Both M43C ΔNSP1 mutant and L81C ΔNSP1 mutant were constructed using site directed mutagenesis on the ΔNSP1 coding sequence (SEQ ID NO: 7) template (previously described by Medalsy et al. [*Nano lett.*, 8, 473-477, 2008]), performed in accordance to the Stratagene Quick-change (Stratagene, La Jolla, Calif.) protocol with the Pfu-Turbo or Deep-vent DNA polymerase.

Primers used for site directed mutagenesis were: C43 (5' CTGCTCGATCTCATTCCAAGCTGTA AGAGTTTCAATTGGGGCACG 3')(SEQ ID NO: 65) for M43C, and C81 (5' GCAAGTCTGGTTTGCAAGA GTACTGCGATTCTGCTGCTCTTGCTG 3') (SEQ ID NO: 66) for L81C.

The mtbSP1 mutant (SEQ ID NO: 3) was constructed using 2 primers: mTB forward primer (5'AAAACATATGCGCAAACTTCCGGATGCGGCAACCAGAACTCCAAAGCTTG-3') (SEQ ID NO: 67) and SP1 reverse primer (5'-AAAAGAGCTCTTAGTAAAGAAAGTAATCAATAAC-3') (SEQ ID NO: 68) with M43C ΔNSP1 coding sequence (SEQ ID NO: 69) as a template.

The L1-SP1CNT mutant (SEQ ID NO: 6) was constructed using the primers: forward primer (5'AAGGAGATATACAAAAACATATGCACTGGTCAGCATGGTGGATACGATCA AATCAATCAGCAACCAGAACTCCAAAG 3') (SEQ ID NO: 70) and reverse primer(5'CTTTGGAGTTCTGGTTGCTGATTGATTTGATCGTATCCACCATGCTGA CCAGTGCATATGTTTTTGTATATCTCCTT 3') (SEQ ID NO: 71) with native SP1 coding sequence (SEQ ID NO: 28) as a template.

The L2-SP1CNT mutant (SEQ ID NO: 14) was constructed using the primers: forward primer (5'AGAAGGAGATATACAAAAACATATGCACTCATCATACTGGTACGCATTCA ACAACAAAACAGCAACCAGAACTCCAAAGC 3') (SEQ ID NO: 72) and reverse primer (5'GCTTTGGAGTTCTGGTTGCTGTTTTGTTGTTGAATGCGTACCAGTATGATGA GTGCATATGTTTTTGTATATCTCCTTCT 3') (SEQ ID NO: 73) with native SP1 coding sequence (SEQ ID NO: 28) as a template.

The L3-SP1CNT mutant (SEQ ID NO: 12) was constructed using the primers: forward primer (5'ATACAAAAACATATGGATTATTTTTCATCACCATATTATGAACAATTATTTG CAACCAGAACTCC 3') (SEQ ID NO: 74) and reverse primer (5'GGAGTTCTGGTTGCAAATAATTGTTCATAATATGGTGATGAAAAATAATCC ATATGTTTTTGTAT) 3 (SEQ ID NO: 75) with native SP1 coding sequence (SEQ ID NO: 28) as a template.

The L6-SP1CNT mutant (SEQ ID NO:15) was constructed using the primers: forward primer (5'AGAAGGAGATATACAAAAACATATGTCAAATCAATCAGCAACCAGAACTC CAAAGC 3') (SEQ ID NO: 76) and reverse primer (5' GCTTTGGAGTTCTGGTTGCTGATTGATTTGACATATGTTTTTGTATATCTCCTT CT 3) (SEQ ID NO: 77) with native SP1 coding sequence (SEQ ID NO: 28) as a template.

The L7-SP1CNT mutant (SEQ ID NO: 16) is identical to L1-SP1CNT sequence, except for mutation of the nucleotide sequence encoding the inserted peptide at 5Ile from ata to att, and at 6Arg from cga to cgt, to improve codon usage. The mutant polypeptide was constructed using the primers: for A24T mutant, forward primer (5'-ACTGGTCAGCATGGTGGATTCGATCAAATCAATCAG-3') (SEQ ID NO: 78) and reverse primer (5'-CTGATTGATTTGATCGAATCCACCATGCTGACCAGT-3') (SEQ ID NO: 79). For A27T mutant, forward primer (5'-GTCAGCATGGTGGATTCGTTCAAATCAATCAGCAACC-3') (SEQ ID NO: 80) and reverse primer (5'-GGTTGCTGATTGATTTGAACGAATCCACCATGCTGAC-3') (SEQ ID NO: 81), using "QuikChange Site-Directed Mutagenesis Kit" of "Stratagene" (La Jolla, Calif.).

The L4-SP1CNT mutant (SEQ ID NO: 9) is identical to L1-SP1CNT sequence, except for mutation of R23K of the inserted peptide. The mutant polypeptide was constructed using the primers: for R23K mutant, forward primer (5'-TGACTCGGTTCAAGGATGAGATCACAAAAGAACA-GATCGACA-3') (SEQ ID NO: 82), and reverse primer (5'-TGTCGATCTGTTCTTTTGTGATCTCATCCTT-GAACCGAGTCA-3') (SEQ ID NO: 83) using "QuikChange Site-Directed Mutagenesis Kit" of "Stratagene" (La Jolla, Calif.).

The L5-SP1CNT mutant (SEQ ID NO: 17) is identical to L1-SP1CNT sequence, except for mutation of T22C of the inserted peptide. The mutant polypeptide was constructed using the primers: for T22C mutant, forward primer (5'-ACTCGGTTCAAGGATGAGATCTGCCGAGAACA-GATCGACAACTAC-3') (SEQ ID NO: 84), and reverse primer (5'-GTAGTTGTCGATCTGTTCTCGGCAGATCT-CATCCTTGAACCGAGT-3') (SEQ ID NO: 85) using "QuikChange Site-Directed Mutagenesis Kit" of "Stratagene" (La Jolla, Calif.).

The L8-SP1CNT mutant (SEQ ID NO: 18) is identical to L4-SP1CNT sequence, except for mutation of the nucleotide sequence encoding the inserted peptide at 5Ile from ata to att, and at 6Arg from cga to cgt, to improve codon usage. The mutant polypeptide was constructed using the primers: for A24T mutant, forward primer (5'-ACTGGTCAGCATG-GTGGATTCGATCAAATCAATCAG-3') (SEQ ID NO: 78) and reverse primer (5'-CTGATTGATTTGATCGAATC-CACCATGCTGACCAGT-3') (SEQ ID NO: 79). For A27T mutant, forward primer (5'-GTCAGCATGGTGGATTCGT-TCAAATCAATCAGCAACC-3')(SEQ ID NO:80) and reverse primer (5'-GGTTGCTGATTGATTTGAACGAATCCACCAT-GCTGAC-3')(SEQ ID NO:81), using "QuikChange Site-Directed Mutagenesis Kit" of "Stratagene" (La Jolla, Calif.).

Wild type SP1 was used as a template for PCR reaction (5'-ACTGGTCAGCATGGTGGATTCGATCAAAT-CAATCAG-3') (SEQ ID NO: 78) and reverse primer (5'-CTGATTGATTTGATCGAATCCACCATGCTGACCAGT-3') (SEQ ID NO: 79) with native SP1 coding sequence (SEQ ID NO: 28) as a template.

All constructs were inserted into pET 29a expression plasmid (Novagen Inc. Madison Wis., USA).

Protein Purification and Refolding:

After centrifugation, cell pellets were resuspended in lysis buffer (50 mM Tris HCL 1 mM EDTA, 10 mM MgCl$_2$, pH 8) and sonicated on ice for several minutes with pulsed bursts. Variants were expressed as soluble proteins [mtbSP (SEQ ID NO: 3), L1-SP1 (SEQ ID NO: 6), L6-SP1 (SEQ ID NO: 15)], or aggregated into inclusion bodies [L2 SP1 (SEQ ID NO: 14) and L3-SP1 (SEQ ID NO: 8)].

The insoluble pellets were separated by centrifugation at 14000×g for 15 minutes. Soluble mutated proteins (M43C ΔNSP1 and mtbSP1; L1-SP1; L2-SP1; L3-SP1; L6-SP1) were then heat treated at 85° C. for 30 minutes and treated by protease (alcalase, Novozyme 10$^6$-fold dilution: 30 min 40° C.)

Inclusion bodies of L81C ΔNSP1 (SEQ ID NO: 2) mutant were washed first for 15 minutes with the IB washing buffer (20 mM Tris HCL, 2 M urea, pH 8) and thereafter centrifuged at 14000×g for 15 minutes. The pellets were resuspended in denaturation buffer (20 mM Tris HCl, 6 M urea, 10 mM dithiothreitol, pH 8) and diluted to protein concentration of 5 mg/ml. Denaturated proteins were then refolded by dialysis against a folding buffer (20 mM Tris HCl, 1 mM DTT, pH 7) for 4 days.

Ion Exchange FPLC:

Hitrap Q Sepharose XL column (1 ml) (Amersham Biosciences, Piscataway, N.J. USA), was used to purify the proteins. Samples were loaded on the column using 20 mM piperazine pH 6.3 buffer at a flow rate of 3 ml/min Elution was conducted with a gradient of 1 M NaCl in the same buffer and determined at 27-33% salt.

mTBP Appendage Peptide:

mTBP peptide (SEQ ID NO: 5) was synthetically manufactured by BioSight ltd. (Karmiel, Israel).

Stability Characterization of Mutated Proteins:

Three different stability analyses were performed on the wild-type SP1 (SEQ ID NO: 4) and each of the mutated proteins.

1. Heat treatment (H.T) at 80° C. for 30 minutes;
2. Boiling treatment (B.T.) at 100° C. for 30 minutes; and
3. Resistance to proteolysis by proteinase K (PK) at a concentration of 50 ug/ml of the enzyme for one hour at 37° C. PK was eliminated by B.T. for 5 minutes.

Alternatively, alcalase was used to determine stability: Alcalase (Novozyme, 1:1000 dilution) was added at 40° C. for 30 mM Reaction was stopped by inhibition of alcalase at 80° C. for 30 min.

All treatment were followed by centrifugation at 14,000×g for 15 minutes, and analyzed by SDS-PAGE.

Silica Binding:

mtbSP1 (SEQ ID NO: 3) was mixed with 10 mg silica gel (product no: 28,860-8, Sigma-Aldrich, USA) in 10 mM MES pH 6.5, 150 mM NaCl, with or without 3M GuHCl. The solution was then incubated for one hour on a rotary shaker at room temperature. Thereafter the silica was washed three times with the same buffer without GuHCl. Bound protein was analyzed either by SDS-PAGE or by measuring protein concentration using the Micro BCA assay kit (Pierce, Rockford, USA).

Surface Preparation and Binding:

Silicon surfaces (0.5 cm$^2$) were sonicated with 75° C. heated isopropanol for 20 minutes, washed with triply distilled water and dried with dry nitrogen. The treated surfaced were plasma cleaned for 3 minutes (Femto Inc., Jettingen, Germany), and the samples were deposited thereafter. Five µl of protein sample at a final concentration of about 2 mg/ml protein in MES buffer at 6.5 pH with or without 3M GuHCl, were deposited on the surfaces for 20 seconds and then gently washed with triply distilled water and dried with dry nitrogen.

Flat gold surfaces preparation procedure: gold is evaporated to form a 100 nm layer on cleaved mica at a rate of 0.5 Å per second followed by the deposition of 5 nm of titanium at a rate of 2 Å per second at a vacuum of over 5 e-7 torr. The evaporated samples are heated on a hot plate for 10-15 nm. 15 µl of epoxy glue (301-2 Epotech, Epoxy Technology Inc, Billerica, Mass., US) is used to glue the evaporated gold to a glass surface, then heated for 3.5 hours at 85° C., followed by over night cooling. Prior to use, the epoxy layer is cleaved using a tetrahydrofuran (THF) solution (99% purity, Frutarom, Haifa, Israel) leaving a clean flat gold surface. Five µl of sample at a final concentration of about 2 mg/ml protein in MES buffer at 6.5 pH are deposited on the flat gold surface for 20 seconds, gently washed with triply distilled water and nitrogen dried.

SP1/CNT Binding:

SP1/CNT binding to aramid was evaluated using three methods:

1. Determination of the difference between CNT content in solution (suspension) before and after its binding to the fabric. CNT content of a suspension is determined by precipitating the SP1/CNT from a sample of the suspension using guanidinium hydrochloride (100 mM) or HCl (0.3%), before and after its incubation with the fabric (combined with the washing solution), drying the pelleted CNT, and weighing;

2. Spectroscopy: CNT content can be evaluated using spectroscopic method, namely, light transmittance by visualization of a fabric or surface coated by CNT at high resolution under a scanning electron microscope (HR-SEM); and 3. Surface resistivity-CNT content of a coated fabric or surface can be assessed by measuring surface resistivity to current flow (this method is relevant only in cases in which the untreated fabric is a insulator or very poor conductor).

Example 1

Gold-Labeling of SP1 Mutants

Gold-labeling of proteins may be accomplished via cysteine side-chains, however, wild-type SP1 (native SP1) (SEQ ID NO: 4) has no cysteine amino acid in its peptide sequence, therefore one can study the importance of specific regions in the folded, oligomeric protein structure and determine their accessibility by testing the binding of an cysteine-substituted SP1 protein to a flat gold surface. To that end, two different SP1 mutants were constructed using standard site directed mutagenesis techniques. In the first mutant, methionine 43 which is located at the protein's inner ring (pore) was replaced with a cysteine (mutant name: M43C ΔNSP1, SEQ ID NO:1). In the second mutant, leucine 81 which is located on the protein outer rim was replaced with a cysteine (mutant name: L81C ΔNSP1, SEQ ID NO: 2)

FIGS. 1A-B are computer-generated presentations of the M43C ΔNSP1 (SEQ ID NO: 1) and L81C ΔNSP1 (SEQ ID NO: 2) mutants, wherein FIG. 1A presents the M43C ΔNSP1 mutant exhibiting thiol groups at the protein inner ring or pore, and FIG. 1B presents the L81C ΔNSP1 mutant exhibiting thiol groups on the protein's outer rim.

As can be seen in FIGS. 1A-B, the cysteine residues in the M43C mutant (arrows) are directed to the inner pore, while the cysteine residues in the L81C mutant (arrows) point out from the rim of the ring structure.

The two mutants were expressed and purified from *E. coli* bacteria and demonstrated characteristics similar to the native SP1 in terms of heat stability, protease resistance and complex formation (Table 1).

FIGS. 2A-B are photographs of SDS-PAGE gel runs, performed for M43C SP1 and L81C SP1 mutants expression and stability experiments. FIG. 2A shows an SDS-PAGE gel analysis of the M43C SP1 fraction from total bacterial protein, before and after IPTG induction (FIG. 2A, lanes 1-2 respectively, the band of the SP1 monomer is encircled with a solid line), from bacteria soluble fraction, without boiling (FIG. 2A, lane 3, the band of the oligomeric dodecamer is encircled with a dashed line) and following boiling (FIG. 2A, lane 4, the band of the monomer is encircled with a solid line). FIG. 2A, lane 5 shows protein from bacterial inclusion bodies. FIG. 2A, lanes 6 and 7 show protein from the bacterial soluble fraction after heat treatment at 85° C. for 30 minutes), with boiling (lane 7) and without boiling (lane 6). FIG. 2A, lanes 8-12 show purified protein, with (lane 9) and without boiling (lane 8); and stability assays: sample exposed to 85° C. (lane 10), 100° C. (lane 11) and proteinase k (lane 12). FIG. 2B showing the analysis of L81C SP with samples in lanes 1-5 exposed to the same conditions as the samples in lanes 1-5 shown in FIG. 2A; refolded protein with- and without boiling (lanes 6 and 7 respectively; and samples in lanes 8-12 exposed to the same conditions as the samples in lanes 8-12 shown in FIG. 2A (MW in kDa).

As can be seen from the mobility on SDS-PAGE electrophoresis (FIGS. 2A and 2B), the mutant SP1 proteins exhibit the same capacity to resist exposure to heat and protease digestion, as the intact dodecameric protein.

The position effect of the single cysteine substitution was analyzed by investigating the affinity of the two mutants to ultra-flat gold surfaces, prepared as described hereinabove. Dynamic mode atomic force microscopy (AFM) topographic imaging (Dulcinea microscope, NanoTec, Madrid) was used to determine the surface coverage by the two proteins, compared to native SP1 under identical conditions (sample concentration, surface treatment and deposition time). Flooding image analysis technique [Horcas, I. R. et al., *Rev. Sci. Instrum.*, 2007, 78, p 013705] was used to determine the surface coverage of the new mutants, and the results are presented in FIG. 3.

FIGS. 3A-C are atomic force microscopy flooding topography images of three ultra flat gold surfaces wherein the blue colored areas represent the exposed gold surface and the red-brown areas represent the protein-covered surface, whereas each of the gold surfaces was treated with a different variant of SP1. Native SP1 (SEQ ID NO: 4) (FIG. 3A) demonstrated poor binding, achieved only 1.5% surface coverage, while M43C ΔNSP1 (SEQ ID NO: 1) (FIG. 3B) achieved only 60% surface coverage. L81C ΔNSP1 (SEQ ID NO: 2) (FIG. 3C) achieved a complete and homogenous coverage of 98% of the ultra flat gold surface, indicating that the thiols of L81C ΔNSP1 are indeed exposed to the surroundings and are capable of binding to a surface. These results show that different positions on the protein structure affect the accessibility of a specific residue or sequence for binding, affording the ability to modify SP1 protein binding to ligands (e.g. gold surface) in a predictable and controllable manner.

Example 2

Binding of SP1 Mutants to Silica Surfaces

In order to assess whether binding of ligands to SP1 residues or sequences can be controlled by influencing the three dimensional conformation of the SP1 oligomer, the M43C ΔNSP1 (SEQ ID NO: 1) was further engineered to present a silicon binding peptide in its inner pore. A polynucleotide encoding the silicon binding hexapeptide mTBP (SEQ ID NO: 5), was genetically fused in-frame to the N-terminal-encoding portion of M43C ΔNSP1 gene and the resultant polypeptide expressed in *E. coli*. The resulting protein (mtbSP, 1 SEQ ID NO: 3) is a ring shaped homo-dodecamer, presenting twelve silicon oxide binding peptides in its inner pore, six at each side of the ring (see, FIG. 4).

Can the affinity of mutant SP1 for a ligand be modified ("switched") by altering the protein's chemical environment? FIGS. 4A-B are computer-generated graphic presentations of the mtbSP mutant, showing the silica binding peptide as golden-colored ribbons extending from the inner pore of the ring-shaped protein. FIG. 4A depicts the closed conformation of the protein which cannot bind to silica, and FIG. 4B depicts the open conformation which can bind to silica surface. "Switching" from open to closed formation was attempted using a chaotropic agent or, in some cases, sonication (using an Elma Transsonic Sonifier), for example, for silica binding.

The mtbSP mutant (SEQ ID NO: 3) was expressed in the bacterial soluble fraction. The resulting mutant protein was compared with native SP1 for heat stability and protease resistance (Table 1).

FIGS. 5A-5B are photographs of SDS-PAGE analysis of mtbSP (SEQ ID NO: 3) expression, characterization and $SiO_2$ binding. Induction of expression of mtbSP (heavy band) is evident from the total bacteria lysate before and after IPTG induction (FIG. 5A, lanes 1 and 2 respectively). Boiling the bacterial lysate soluble fraction (FIG. 5A, lane 3) results in increased representation of mtbSP monomers, as compared to the high molecular weight oligomeric form predominant in the un-boiled soluble fraction (FIG. 5A, lane 4).

Bacteria expressing mtbSP had numerous inclusion bodies, containing predominantly mtbSP monomers (FIG. 5A, lane 5).

Heat treatment (85° C. for 30 minutes) of the mtbSP bacterial soluble fraction does not impair oligomer formation (FIG. 5A, lane 6, heat treated+boiling, lane 7, heat treated without boiling). The mtbSP bacterial soluble fraction was also proteinase resistant: FIG. 5A, lanes 8 and 9 show the mtbSP bacterial soluble fraction with and without proteinase k treatment, respectively, similar to protease resistance of native SP1 [FIG. 5A, lanes 10=+protease k, lane 11=no protease).

The presence of the mTBP hexapeptide (SEQ ID NO: 5) in mutant mtbSP1 imparts silica binding ability. As can be seen in FIG. 5B, SDS-PAGE analysis of the mtbSP and native SP1 following incubation with silica beads, the mtbSP protein binds to silica beads while the native SP1 does not. As can be seen in FIG. 5B, mtbSP remained with the silica beads (FIG. 5B, lane 1), and hardly any mtbSP was recovered from the unbound fraction (FIG. 5B, lane 2), while native SP1 was not detected on the silica beads (FIG. 5B, lane 3) and remained predominately in the unbound fraction (FIG. 5B, lane 4). SDS-PAGE analysis of the binding of a preparation of mixed mtbSP and native SP1 proteins indicated only the less mobile (upper band) mtbSP in the bound fraction released from the silica beads (FIG. 5A, lane 5, compared to lane 6, unbound fraction). When not disassociated by boiling before SDS-PAGE, both bound mtbSP (FIG. 5B, lane 7), native SP1 (FIG. 5B, lane 8) and a mixture of mtbSP and native SP1 (FIG. 5B, lane 9) appear predominantly as the high molecular weight oligomeric complex. Thus, mtbSP binds silica beads, while native SP1 cannot.

To characterize the mtbSP1 interaction with silica, and to test whether alteration of the chemical environment (solvent) affects SP1 ligand binding, binding of mtbSP1 (SEQ ID NO: 3) was compared with that of the free mTBP silica binding peptide (SEQ ID NO: 5). FIGS. 6A and 6B show the binding of mtbSP (FIG. 6B) and the free mTBP hexapeptide (FIG. 6A) to silica beads, in the presence (open boxes □) or absence (Xs) of a chaotropic agent (3M GuHCl). While the binding of the free mTBP peptide to silica was essentially unaffected by GuHCl (FIG. 6A), GuHCl greatly improves silica binding of the SP1-bound mtbSP1 (FIG. 6B). Similar response to GuHCl has been observed with cysteine-mediated binding of M43C-SP to gold nano-particles [Medalsy, I. et al., *Nano lett.*, 2008, 8, 473-477, fully incorporated herein].

While not wishing to adhere to a single hypothesis, one possibility is that GuHCl, which in most cases denatures proteins, allows certain steric flexibility to the N-termini of the highly stable SP1 complex and consequently exposes the attached silicon binding hexapeptide to the surrounding environment, facilitating its binding to the silica (see, FIG. 4B). Further evidence for such a mechanism was provided by showing that sonication can replace GuHCl for silica binding (data not shown).

When comparing the dissociation constants of mtbSP and free mTB hexapeptide on Scatchard analysis, it was surprisingly uncovered that the mutant mtbSP (SEQ ID NO: 3) (FIG. 7C, solid diamonds ♦) has a dissociation constant orders of magnitude lower than that of the free mTB hexapeptide (FIG. 7C, open squares □). Scatchard analysis of the curves (FIGS. 7A and 7B) show a $K_d$ of 0.3 µM for the protein mtbSP and $K_d$ of 86 µM for the free mTB peptide, and positive cooperative silica binding of the mtbSP.

As can be seen in FIGS. 7A-C, a $K_d$ of 0.3 µM for mtbSP, compared to a $K_d$ of 86 µM for the peptide, indicates that when the mTB hexapeptide is presented on the SP1 scaffold, its affinity to the silica is 2-3 orders of magnitude higher. This is corroborated by the Scatchard analysis which demonstrates positive cooperative effect for the mtbSP, but not for the free peptide.

The observed dissociation constant of the free synthetic mTBP, 86 µM, is in good agreement with the Kd of the original TBP-1 peptide (Sano et al. *Langmuir.*, 2005, 21, 3090-3095), considering that mTBP displays only the most necessary amino acids of TBP-1. Avidity was increased by nearly 3 orders of magnitude by displaying the mTBP on the SP1 dodecamer.

In order to further assess the affect of the chaotropic agent GuHCl ("switching") on binding of the mtbSP dodecamer to silica surfaces, atomic force micrography (AFM) imaging of $SiO_2$ surfaces was performed.

FIGS. 8A-H are a series of AFM flooding topography images of different SP1 mutants bound to silica surfaces, showing variable binding to the $SiO_2$ surface in the presence, or absence of 3M GuHCl or without GuHCl. In the AFM images, the blue areas represent the bare silica surface and the brown areas represent the protein-bound silica surface. FIGS. 8A-D are of native SP1 (SEQ ID NO: 4), L81C ΔNSP1 variant (SEQ ID NO: 2), M43C ΔNSP1 variant (SEQ ID NO: 1) and mtbSP (SEQ ID NO: 3) respectively. Without GuHCl, all show low non-specific binding (less then 5% surface coverage) of the $SiO_2$ surface. FIGS. 8E-H are also of native SP1 (SEQ ID NO: 4), L81C ΔNSP1 variant (SEQ ID NO: 2), M43C ΔNSP1 variant (SEQ ID NO: 1) and mtbSP (SEQ ID NO: 3), respectively, in the presence of 3M GuHCl. With GuHCl, the AFM images clearly show that only mtbSP exhibits full coverage of the $SiO_2$ surface, with reduced non-specific binding.

As can be seen in FIGS. 8A-F, all mutants show surface coverage in the range of 1-7% with no significant differences, while GuHCl allows full surface coverage of the silica with a mtbSP mono-layer. The high stability of the SP1 scaffold, allows it to expose the hidden peptides only in solvent condition that would denature most proteins. Moreover, the use of a chaotrophic agent such as GuHCl significantly reduces non-specific binding to the surface as can be seen in FIGS. 8A-B.

Example 3

Carbon Nanotubes (CNT) Dispersion by SP1 Variants

Materials and Methods:

Multi wall carbon nanotubes (MWCNT) were obtained either from Arkema Inc., France (GRAPHISTRENGTH™ C100) or from Bayer MaterialScience AG, Germany (Baytubes C150 P). Single wall carbon nanotubes (SWCNT) were obtained from Teijin, Ltd (Yamaguchi, Japan).

For small scale production, between 1.0 and 1.3 mg of MWNTs were weighed in 1 ml screw-cap glass tube (Fisherbrand, cat. no. 03-338 AA, size 12×35 mm, ½ DR). A 1 ml protein solution in NaPi buffer (10 mM; pH 8.0) was added to the screw-cap glass tubes containing pre-weighted MWNTs. The resulting mixture was sonicated for 2 hours at 80° C. using an Elma Transsonic Sonifier. The sonicated samples were first centrifuged in an Eppendorf centrifuge tube for 20 minutes at 20000 Xg. Ninety percent of the upper supernatant was separated using a pipette, avoiding taking the sediment at the bottom, and transferred to another Eppendorf centrifuge tube. The separated supernatant samples were diluted ten-fold. The CNT dispersion by L2-SP1 (SEQ ID NO: 14) was also tested in Tris buffer (10 mM; pH 8.0) with or without urea.

For larger scale production, 400-mg of MWCNT were weighed into a glass flask, a protein solution (400 ml in NaPi buffer; 10 mM; pH 8.0) was added, and the mixture sonicated at a power setting of 260 W for 4 hours, maintaining a maximal temperature of less than 50° C., using a Misonix 4000 Sonicator with a booster home, a 1 inch flat tip and a temperature control unit or a Hielcher sonicator (UIP1000 hd). In order to obtain full dispersion of the sample, the sonicated samples were centrifuged in an Eppendorf centrifuge tube for 20 minutes at 20000 Xg until only a minor pellet was formed. After pelleting of the undispersed material, the supernatant was very dark with the CNT, even after 100 fold dilution in the same buffer. The last step was centrifugation of the suspension for 60 minutes at 7000 rpm using a Sorval SLA 3000 centrifuge.

Results:

Table 2 hereinabove, presents the results of the CNT dispersion experiments. The SP1 variants described in Table 2, are heat stable and generally protease resistant, however, incubation with alcalase (1000-fold dilution) causes a shift in the molecular weight relative to samples not treated with alcalase. In all cases the apparent molecular weight of the alcalase-treated SP1 variants was still higher than those of native SP1, indicating that some but not all the amino-acids derived from the CNT binding peptides were removed.

As can be seen in Table 2, fusion of copies of these CNT binding peptides to SP1 N-terminus improves the SP1's ability to disperse multi wall carbon nanotubes (MWCNT) in a solvent, while native SP1 protein affords MWCNT dispersion only at high SP protein concentrations (approx. 1 mg/ml). As can further be seen in Table 2, the fusion proteins have a much higher CNT-binding activity. The greatest CNT dispersing capability was observed with L1 (SEQ ID NO: 6), an SP1 polypeptide with the HWSAWWIRSNQS peptide (SEQ ID NO: 10) fused to the N-terminus, which allowed MWCNT dispersion at the relatively low concentration 0.004 mg/ml. Fusion of SP1 with the other CNT-specific peptides L2 (SEQ ID NO: 14) and L3 (SEQ ID NO: 8) [HSSYWYAFNNKT (SEQ ID NO: 11) and DYFSSPYYEQLF (SEQ ID NO: 12) peptides respectively] also resulted in greater CNT dispersing activity than native SP1. Using the L3-SP1 the Hielcher sonicator, maximal CNT concentration was 40 mg CNT/gr fabric, or 4%. If SP1 solubility is as high as 150 mg/ml theoretically, maximal CNT concentration, can be as high as 30%.

Variants L2-SP1 (SEQ ID NO: 14) and L3-SP1 (SEQ ID NO: 8) differ from other SP1 variants in that they form both soluble and insoluble protein found in inclusion bodies (IB). The protein found in IB can be dissolved in the presence of urea and refolds upon urea dilution. While properly folded L2-SP1 forms complexes and was protease resistant, the dissolved L2-SP1 from IB did not form complexes and was protease sensitive. The L2-SP1 and L3-SP1 from inclusion bodies can disperse CNT but with much less efficiency than the soluble protein (Table 2).

As can be seen in Table 2 hereinabove, the minimal SP1 concentration required for CNT dispersion depends on the sequence of the peptide fused to the N-terminus.

In the case of L1-SP1 (SEQ ID NO: 6), an ion exchange purified protein was treated with alcalase, and the protein underwent N-terminus sequencing and molecular weight determination using MOLDY-TOF. The results indicated that 8 amino acids were digested by the alcalase from its N-terminus, leaving the SNQS peptide fused to the protein N-terminus. It is noted herein that the SP1 variant with an insertion of the SNQS peptide at the N-terminus (L6-SP1, SEQ ID NO: 15) exhibited similar characteristics, namely mobility in SDS PAGE and CNT dispersion ability, as compared to the alcalase-treated L1-SP1.

In addition to the CNT specific peptides, fusion of the silicon/titanium oxide binding peptide (RKLPDAA) (SEQ ID NO: 5), which yields the SP1 variant mtbSP1 (SEQ ID NO: 3), was found to facilitate CNT dispersion at lower concentration than native SP1.

For industrial applications it is preferred to keep the protein production costs as low as possible, and to make sure that other peptides that may exist in the crude extract of transformed cells expressing a recombinant protein do not interfere with the variant SP1's CNT dispersion capability. To test this facet, crude extract obtained from bacteria transformed to express L1-SP1 was exposed to combinations of heat and protease treatments, and was then assessed for the retention or loss of CNT dispersion activity, as presented in Table 5.

TABLE 5

| | Crude extract treatment | | CNTs dispersion | |
|---|---|---|---|---|
| | Heat treatment | Alcalase treatment | Maximal dilution | Minimal protein concentration μg/ml |
| Standard treatment. | 80° C., 30 minutes × 2 | + | 1:26 | 10 |
| Heat treatment. | 80° C., 120 minutes | − | 1:26 | 9.3 |
| Alcalase treatment with final inactivation of alcalase | 80° C., 30 minutes after alcalase treatment | + | 1:26 | 6 |
| Alcalase treatment without final Inactivation of alcalase. | — | + | 1:26 | 11 |

As can be seen in Table 3, the heat treatment of crude extract of L1-SP1, up to 120 minutes at 80° C. and proteolysis used during the preparation of the mutant, did not abolish the capacity to disperse CNT.

A direct demonstration that L1-SP1 binds to CNT and forms a complex was obtained by comparing a suspension of a sample of L1-SP1 (SEQ ID NO: 6) with CNT (L1-SP1/CNT), a sample of the protein without CNT (L1-SP1) and a filtrate (0.22 micron filter) of these two samples before and after boiling. Both the boiled and not boiled samples were analyzed by SDS PAGE.

The boiled L1-SP1 was detected as a band of the monomeric form and a band of the trimeric form, while the unboiled L1-SP1 appears as a high molecular weight complex only.

A large fraction of the CNT was excluded by filtration, therefore longer than 0.22 micron. The proportion of the SP1 trimer bands in the absence of CNT was lower than that detected in the presence of CNT, both in the filtrates and in the unfiltered samples. Apparently not all the protein dissociated upon mixing with the SDS Tricine sample buffer and SDS PAGE application.

Another indication that the L1-SP1 protein (SEQ ID NO: 6) binds to the CNT comes from the protein determination assay (Bradford protein assay) of both mtbSP-SP1/CNT suspension and the microfiltration (0.2 micron) flow-through, demonstrating that about 50% of the protein after CNT complexing is larger than the 0.2 micron pore size and is retained by the filter (data not shown).

Yet further evidence for the formation of a SP1-CNT complex is seen in the results of ethanol precipitation (Table 3): While uncomplexed protein does not precipitate with 50% ethanol, SP1-CNT does precipitate with 50% ethanol. CNT precipitate also with GuHCl (100 mM) and in acidic pH (by adding HCl or acetic acid), however, while GuHCl does not induce uncomplexed protein precipitation but acidic pHs does. This phenomenon is used to determine CNT concentration to fabrics (see Examples 6-8).

Heat stability, protease and alkali resistance of L1-SP1-CNT complex: To assess the stability of the complex, L1-SP1/CNT was subjected to heat treatment (100° C.; 10 minutes or 80° C.; 30 minutes) both at pH 8.0 and pH 11, or proteolysis at pH 8.0. Incubation of L1SP1/CNT samples, at different pHs, were followed by high speed centrifugation (20 minutes; 20000 Xg) and 10-fold dilution of the supernatant. The results of the heat and proteinase assays demonstrate that the SP1/CNT complex is heat stable and protease resistant, allowing economically desirable heat drying and powdering of the complex prior to its dispersion in important polymeric compounds, such as epoxy.

The high durability of the SP1/CNT complex allowed the development of simple method to obtain a dry pellet of SP1/CNT complex that can easily re-dispersed in water. The process includes first dispersion of 4% CNT, followed by three steps of wash and precipitation by 1:5 dilution in ethanol (final 99% ethanol), and dehydration using a vacuum pump.

Example 4

Dispersion of SP1/MWCNT Complex in Epoxy Resin

A well studied model for protein-epoxy interaction is the epoxy-activated polymer support, used for immobilization of bio-active proteins, e.g. enzymes. However, soluble proteins are scarcely reactive with epoxy groups at neutral pH values. The SP1-CNT solubility capacity in epoxy is pH-dependent: SP1-CNT precipitates when it is dried at pH 8.0 and it forms a stable clear but dark solution when it is dried at a pH greater than 10.5.

Two exemplary general procedures for forming a tri-complex of SP1 variants, carbon nanotubes and epoxy resin are described herein General protocol "A": In order to assess SP1/CNT interaction with epoxy, 1. SP1/CNT (0.1-0.5% CNT) was dispersed in water using sonication as described hereinabove;

2. A concentrated SP1/CNT suspension was prepared using ultra-filtration (30 kDa cutoff) and buffer replacement to increase pH (from NaPi, 10 mM; pH 8.0; to $Na_2CO_3$, 10 mM, pH-11), using dialysis.

3. Dehydration: Freeze drying (lyophilization) was used for dehydration of the sample, in order to obtain a dry, fine SP1/CNT pellet.

4. The SP1/CNT pellet was vigorously mix the in epoxy (Huntsman, LY5052) for 10 mM, to yield 1% (w/w) concentration, followed by bath sonication for 3 hours at 260 W and maximum temperature of 70° C.

5. Centrifugation: The black mixture was then centrifuged at (60 minutes at 7000 rpm using a Sorvall SLA 3000 rotor) to precipitate the undispersed CNT/SP1; and 6. CNT suspension concentration was evaluated by measurement of transmission at 600 nm General protocol "B" includes the following steps:

1. SP1/CNT (0.1-0.5% CNT) was dispersed in water using sonication as described hereinabove;

2. pH adjustment by addition of NaOH (final concentration of 0.02 M);

3. Ethanol precipitation: adjust to 50%-80% ethanol, incubate 2 hours at −20° C., followed by centrifugation for 60 minutes at 7000 rpm (Sorval rotor SLA 3000 on a Sorval centrifuge;

4. Dehydration: Freeze drying (lyophilization) was used for dehydration of the sample, in order to obtain a dry, fine SP1/CNT pellet.

4. The SP1/CNT pellet was vigorously mixed with the epoxy (Huntsman, LY5052) for 10 min, to yield 1% (w/w) concentration, followed by bath sonication for 3 hours at 260 W and maximum temperature of 70° C.

5. Centrifugation: The black mixture was then centrifuged at (60 minutes at 7000 rpm using a Sorvall SLA 3000 rotor) to precipitate the undispersed CNT/SP1; and 6. CNT suspension concentration was evaluated by measurement of transmission at 600 nm The transparent epoxy was then weighed for addition of hardener, mixed for 7-10 min, degassed in a vacuum dessicator and poured into a silicon mold for curing at 80° C. over night (>8 hours). FIG. 9A shows a photograph of modules produced from cured LY5052 epoxy (sample 1) compared to Epoxy LY5052 with dispersed complex TiSP1-CNT (sample 2) (~1%) (mtbSP1, SEQ ID NO: 3) and epoxy LY5052 with untreated CNT (sample 3) (1%). The photograph shows that the CNT dispersion by SP1 protein yields a dark but clear sample, indicating good dispersion in the epoxy.

FIG. 9B also shows a TEM image of a thin section of epoxy LY5052 with dispersed complex TiSP1-CNT (~1%) (mtbSP1, SEQ ID NO:3), clearly showing fully dispersed CNT in the cured, polymerized epoxy.

Example 5

SP1 Variants Binding to Aramid (e.g. KEVLAR™)

Material scientists and engineers are excited by the possibilities for creating super-strong, high-performance polymer composite materials using carbon nanotubes. Currently, all existing methods of fabricating CNT-polymer composites involve complicated, expensive, time-demanding processing techniques such as solution casting, melting, molding, extrusion, and in situ polymerization, requiring that the nanotubes either be incorporated into a polymer solution, molten polymer or mixed with the initial monomer before the formation of the final product (e.g. yarn, ribbon or film). This is unsuitable for insoluble or temperature sensitive polymers, which decompose without melting.

Aramid polymers (e.g. KEVLAR™) is a well known high-strength polymer with a variety of important applications such as pneumatic tire tread and sidewalls, bullet-proof vests and car armor plating. However, aramid (e.g. KEVLAR™) is not soluble in any common solvent and, having no melting point, decomposes above 400° C. As a result, aramid (e.g. KEVLAR™) fibers must be produced by wet spinning from sulphuric acid solutions. Binding of SP1/CNT complex to aramid (KEVLAR™) was assessed for effective post-processing incorporation of carbon nanotubes into already formed polymer products, such as, for example, aramid (KEVLAR™) yarns.

CNT binding to the fabric via the protein increases its surface area, allowing better interaction with the fiber and induces cross linking between the fibers. In addition, protein biding to the fiber by itself may improve the interaction with the polymer through reactive groups on the protein surface. It is demonstrated that some SP1 variants that bind CNT also bind to structural fibers.

Materials and Methods

Figure 10A:
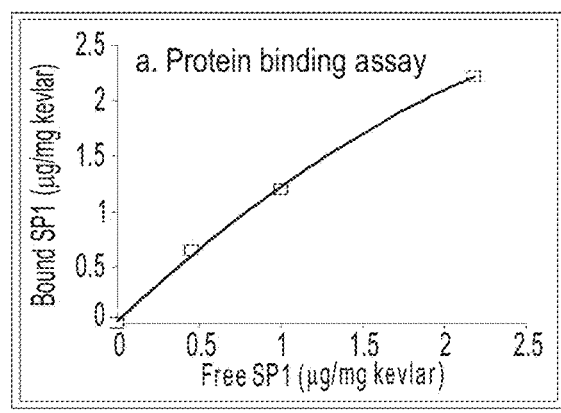

L3SP1 solution (SEQ ID NO: 8), in different concentrations (22 µg/ml, 44 µg/ml, and 88 µg/ml samples in 10 mM NaP$_i$, pH-8) was incubated with 100 mg of aramid (KEVLAR™) fabric in a rotary shaker at 25° C. for 16 hours, followed by extensive wash with the same buffer to remove traces of the unbound protein and CNT, until the solution was colorless, indicating absence of CNT, and until no protein was detected in the wash. CNT binding to the aramid (KEVLAR™) was assessed by darkening of the aramid (KEVLAR™) fibers. SP1 binding to the washed aramid (KEVLAR™) was determined by reacting the aramid (KEVLAR™) with 2 ml of BCA protein assay reagent (Pierce, cat No. 23227) for 30 minutes at 37° C., and measurement of optical density at 562 nm. The amount of protein bound was calculated and plotted, and the results are presented in FIG. 10A.

SP1/CNT binding to aramid was evaluated by precipitation, light transmittance (spectroscopy, visual inspection) and surface resistivity, as detailed above.

Results

Figure 10B:
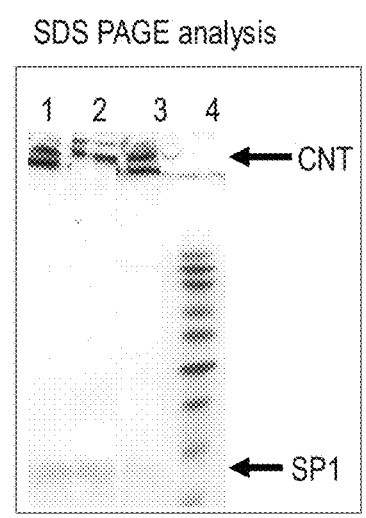

Comparison of the bound and unbound fibers after incubation with the L3 SP1/CNT complex, indicated extensive binding of the CNT, even after exhaustive washing (not shown). BCA protein assay also showed that SP1/fabric (w/w) ratio is approximately 2 mg protein/g fiber (2/1000). In parallel experiments it was demonstrated that L-1-SP1 (SEQ ID NO: 6) and L-4 SP1 (SEQ ID NO: 9) also bind to aramid (KEVLAR™). Following incubation with L3-SP1/CNT aramid (KEVLAR™) fibers turned dark in color, indicating binding of the CNT thereto even after extensive wash. FIG. 10B is a SDS PAGE analysis of SP1/CNT-bound to aramid (KEVLAR™) demonstrating CNT and protein binding to the fiber. Incubation of 30 mg aramid with 180/1000 w/w L4-SP1-CNT dispersion, followed by bath sonication (90 min temperature ranging between 30-70° C.), fiber removal, extensive washing (using the buffer) and boiling (10 min in 60 ul) to extract bound protein and CNT produced darkened fibers bearing bound protein as well as bound CNT (FIG. 10B, lanes 1-3).

In order to obtain a quantitative measure of the amount of aramid (KEVLAR™)-bound CNT, the amount of unbound SP1/CNT remaining in solution following binding can be directly assessed (see Example 6 below).

Figure 11B:
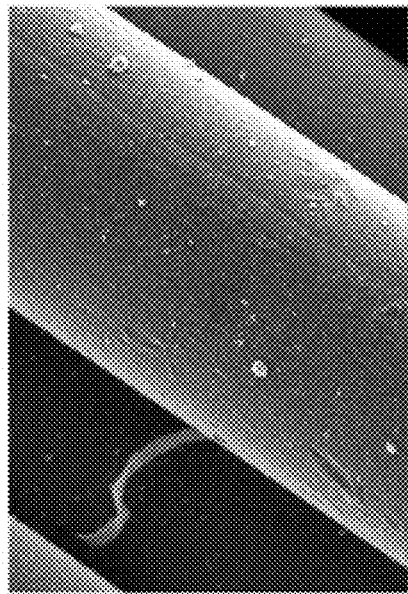
Figure 11C:
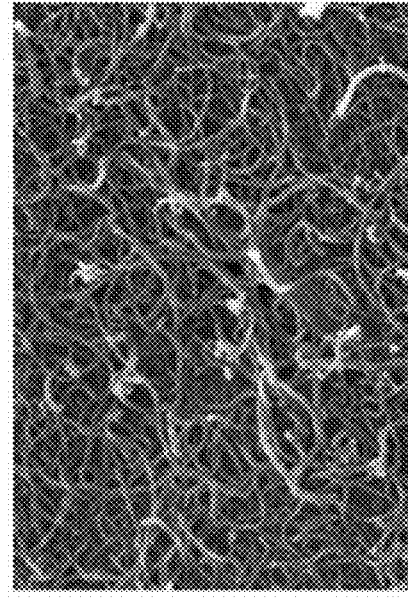
Figure 11A:
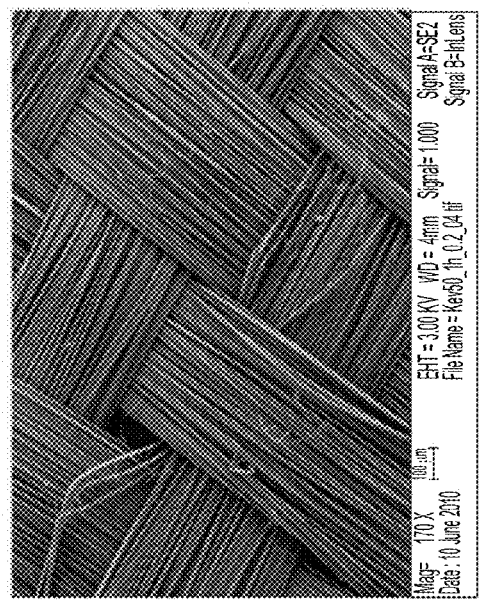
Figure 12A:
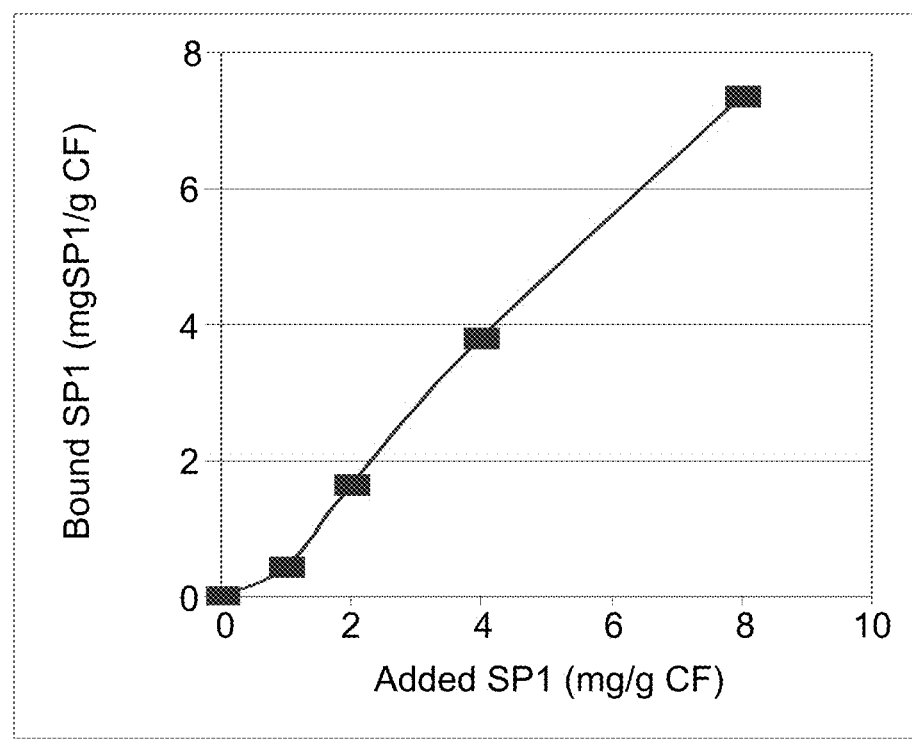

FIGS. 11A-11C are high resolution scanning electron microscopy images of MWCNT bound aramid fiber. The scale bar is 1 µm 00, 1.0 µm, and 0.1 µm, in 11A, 11B and 11C, respectively.

CNT dispersion (0.1% CNT (Arkema, code C100), using L3SP1 (SEQ No 8)) was incubated with aramid fabric (KEVLAR style 120 plain weave 195 Denier, 58 g/m square; 22 ml suspension per g fabric) by agitation (1 h; 25° C.; 150 rpm) followed by extensive wash in the same buffer, and drying in the open air, over night. CNT content on fabric was about 9 mg/g fabric. Note that the bound CNT dramatically increases surface area, and that the CNT are in close contact with one-another, affording improved electrical conductive properties. FIGS. 11B and 11C show homogeneous binding to the aramid fibers, with no indication of aggregation.

Electroresitivity of SP1-CNT-Polymer Fiber Surfaces:

Measurement of resistivity of the surface of SP1-polypeptide-CNT-complexed-aramid fabric surprisingly indicated that while untreated aramid fiber surface resistance is greater than $10^6$ Ohm/square upon complexing with the SP1-polypeptide-bound CNT, resistivity decreases to less than $10^4$ Ohm/square. Varying the bound CNT concentration resulted in corresponding alteration in resistivity of the SP1-polypeptide-CNT-complexed-aramid fabrics-surface resistance decreased even more upon both increase in CNT concentration and the use of dissolved L3SP1 inclusion bodies (IBs see example 6 below).

Example 6

SP1 Variants Binding to Carbon Fabric

Carbon fabric is a well known high-strength material with a variety of important applications in aerospace and automotive fields, as well as in sailboats and sport equipment, where its high strength-to-weight ratio is of importance. Continuous carbon fiber/epoxy composites have been widely used for structural applications due to their excellent mechanical properties. The polymer is most often epoxy, but other polymers, such as polyester, vinyl ester or nylon, are also used. However, their matrix-dominant properties, such as in-plane and interlaminar shear properties, are much weaker than their fiber-dominated properties, thus limiting the benefits of these conventional composites. In addition, it is known that composites exhibit lower longitudinal compressive strength, a matrix-dominated property, than tensile strength.

CNT binding to the fabric via the protein increases its surface area, allowing better interaction with the fiber, and induces cross linking between the fibers. In addition, protein binding to the fiber by itself may improve the interaction with the polymer through reactive groups on the protein surface. It is demonstrated that some SP1 variants that bind CNT also bind to structural fibers.

Materials and Methods

Production of SP1-CBD Dissolved Inclusion Bodies:

SP1-CBD is expressed in bacterial hosts as insoluble inclusion bodies (IBs), as described in U.S. Pat. No. 7,253,341 to Wang et al. Briefly, SP1 cDNA encoding a 108 SP1 amino acid sequence (SEQ ID NO: 88) was cloned into an expression vector bearing a nucleotide sequence encoding a 163 amino acid CBD domain of *Clostridium cellulovorans* cellulose binding protein A (SEQ ID NO: 87). The resulting nucleic acid construct encoded a SP1-CBD fusion protein which includes a peptide linker (SEQ ID NO: 89). Following cloning, the resulting plasmid was used to transform *E. coli* strain BL21 (DE3). Recombinant CBD-SP1 fusion protein synthesis was induced in BL21 (DE3) by the addition of IPTG (isopropyl-D-thiogalactoside) to a final concentration of 1 mM to mid-log phase of the bacterial culture, followed by five additional hours induction at 37° C. Recombinant SP1-CBD fusion protein (SEQ ID NO: 86) was detected in inclusion bodies (IB), and the inclusion bodies isolated and purified. Briefly, IBs containing SP1-CBD were dissolved in Trisma base (20 mM), NaOH (8 mM) (30, min on ice, 1:200 ratio (w/v)), followed by high speed centrifugation, 13,000 rpm for 30 min. The supernatent was diluted 1:10 in water and the pH was adjusted to pH=8.2 (using NaPi buffer, 100 mM pH=6.8).

SP1 Polypeptide-CNT-Complex Binding to Carbon Fiber

For analytical purposes, 50 mg of carbon fiber (Sigmatex) weighed in 1 ml screw-cap glass tube (Fisherbrand, cat. no. 03-338 AA, size 12×35 mm, ½ DR) L3SP1 solution (SEQ ID NO: 8), (0, 50, 100, 200 and 400 (ug/ml) corresponding to 0, 1, 2, 4, and 8 (mg SP1/g CF) in 10 mM $NaP_i$, pH-8) was incubated in a bath sonicator (using Elma Transsonic Sonifier for 1.5 hours (while operating the bath sonicator the temperature increased from 20 to 60° C.), followed by extensive wash with the same buffer to remove traces of the unbound L3-SP1 protein. SP1 binding to the washed fabric was determined by reacting the fabric with 2 ml of BCA protein assay reagent (Pierce, cat No. 23227) for 30 minutes at 37° C., and measurement of optical density at 562 nm. The amount of protein bound was calculated and plotted, and the results are presented in FIG. 12A. FIG. 12A shows BCA protein assay also shows that SP1/fabric (w/w) ratio is up to 7 mg protein/g fiber (0.07%).

For binding of SP1/CNT complex to fabric, the carbon fabric (Sigmatex, 200 g/square meter, 19 g) was pretreated with L3SP1 solution (SEQ ID NO: 8) {0.025 (ug/ml); 1 (mg SP1/g CF) diluted in 0.8 l of 10 mM $NaP_i$, pH-8} in a bath sonicator (using Elma Transsonic Sonifier) for 1 hour, followed by treatment of the pretreated fabric with L3-SP1/CNT solution {0.1% CNT L3-SP1/CNT (w/w) ratio=0.05 in 0.8 l of 10 mM $NaP_i$, pH-8} in a bath sonicator for 5 hours.

The binding of CNT to the fabric was assessed using two methods:

1. Measuring transmittance of the L3-SP1/CNT suspension at 600 nm over the duration of the sonication, which indicates reduction in CNT concentration in solution, and therefore its binding to the fabric. The transmittance values were correlated to CNT concentration according to L3-SP1/CNT standard curve (FIG. 14B). FIG. 12C shows the reduction (of CNT from solution, as measured by increasing transmittance at 600 nm) over time of sonication, (0 to 5 hours), indicating that the L3SP1-CNT complex binds to the fabric. The maximal CNT binding as measured by this "subtraction" method was 4 mg CNT/gr fabric 0.4%.

2. A more direct method to evaluate CNT binding to the fabric is dry material weighing after solution dehydration (using freeze drying). The difference between dry material weight before and after binding was calculated, indicating that maximal CNT binding as measured by this method was a similar 3.6 mg/gr fabric (0.36%), similar to the results obtained measuring with the "subtraction" method above.

As described above SP1 and SP1/CNT complex binds carbon fibers with limited efficiency unless sonicated. Greater efficiency of binding can be achieved using dissolved SP1-CBD inclusion bodies in which the material binding site domain is exposed. In order to prepare the carbon fiber for binding to the SP1 polypeptide-carbon nanotube complex, the carbon fiber (Hexcel, plain wave style K-70-P 3000 filament yarn; 193 g/m square; 22 ml suspension per g fabric) was exposed to dissolved SP1-CBD fusion protein, in solution (final protein concentration was 0.2 mg/ml) agitation (1 h; 25° C.; 150 rpm), followed by extensive washing to remove the unbound fusion protein. The SP1-CBD-bound carbon fiber was then incubated with SP1-polypeptide-CNT complex suspension (0.1% CNT (Arkema, code C100), in the presence of L3SP1 (SEQ ID NO 8)) by agitation (1 h; 25° C.; 150 rpm) followed by extensive buffer wash, and drying in the open air over night. CNT content bound to the fabric was about 6 mg/g fabric.

Example 7

Electrically Conducting Textiles

Traditional textiles, both natural and synthetic, are almost always insulators (poor conductors of electricity). The interest in transforming them into conductors arises from the need to obtaining antistatic or electromagnetic shielding garments, or for the production of the revolutionary electronic "smart" textiles.

The "electronic/smart textiles" are attracting increasing attention; they contain sensors, actuators and control units but still retaining the features necessary for comfortable clothing. They may be either passive, i.e. capable of sensing the surrounding conditions, and active, i.e. containing both sensors and actuators to respond/adapt to specific inputs. Some non limiting examples of textiles suitable for production of conductive textiles according to the methods of the present invention are natural materials, like cotton, wool and flax, and synthetic fibers, like elastane (polyurethane/polyurea copolymer e.g. SPANDEX, LYCRA) and aramid (KEVLAR), with the addition of ICPs (inherently conducting polymers), like PPY (polypyrrole) or PANi (polyaniline), and CNT (carbon nanotubes).

Methods

Carbon nanotubes were bound to fabric/textiles in a two-step procedure-briefly, L3SP1 (SEQ ID NO: 8) and SP1-CBD (SEQ NO: 86) is expressed both as soluble complex and insoluble inclusion bodies (IBs). IBs of L3SP1 were dissolved in Trisma base (20 mM), NaOH (8 mM) (30, min on ice, 1:200 ratio (w/v)), followed by high speed centrifugation, 13,000 rpm for 30 min. The supernatant was diluted 1:10 in water and the pH was adjusted to pH=8.2 (using NaPi buffer, 100 mM pH=6.8).

As shown in Table 6, two step binding is effective in binding CNT to fabrics such as aramid (without sizing) cotton, polyester, polyamide and elastane. Other fibers such as aramid (KEVLAR style 120 plain weave 195 Denier, 58 g/m square), used for aviation applications, binds CNT by immersion in 0.1% L3-SP1/CNT solution. Such CNT bound fabrics display lower electrical resistivity than untreated fabrics (Table 6), in clear correlation to the presence, or absence (see, for example, Polyamide and cotton) of CNT. Fabrics were prepared as described, with or without SP1L3-IBs (0.1 mg/ml).

TABLE 6

SP1-mediated CNT binding decreases electrical resistivity of fabric

| Fabric | Treatment 1st step | 2nd step | bound CNT (mg/g) | surface Resistance kOhm square |
|---|---|---|---|---|
| Aramid | SP1L3-IB | 0.1% CNT | 6 | 10 |
| | Buffer | 0.1% CNT | 6 | 10 |
| Polyamide | SP1L3-IB | 0.1% CNT | 11.4 | 32 |
| Polyamide | Buffer | 0.1% CNT | 0 | >1000 |
| Cotton | SP1L3-IB | 0.1% CNT | 5.8 | 78 |
| Cotton | Buffer | 0.1% CNT | 0 | >1000 |
| Polyester | SP1L3-IB | 0.1% CNT | 8.4 | 115 |
| Polyester | Buffer | 0.1% CNT | 0 | >1000 |
| Elastane (Lycra™) | SP1L3-IB | 0.1% CNT | ND | 52 |
| Elastane (Lycra™) | Buffer | 0.1% CNT | ND | >1000 |

TABLE 7

Electrical conductivity of CNT bound elastane reversibly decreases upon fabric deforming (stretching).

| | Distance between electrodes, mm | surface Resistance kOhm square |
|---|---|---|
| Relaxed fabric | 90 | 170 |
| Stretched fabric | 150 | 80 |

Taken together, the results brought herein show that specifically designed SP1 variants can form molecular complexes with broad range of inorganic molecules, enhancing physico-chemical characteristics of these molecules such as dispersion in solvents, which molecular complexes can be useful, for example, in the production of highly specific composite materials such as SP1-polypeptide-CNT-aramid complex fabrics, yarns and polymeric fabrics, and CNT-nanostructures.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES CITED

Other References are Cited in the Text

1. Wang, W. et al., Aspen SP1, an exceptional thermal, protease and detergent resistant self-assembled nanoparticle. *Biotechnol. Bioengineering.* 5, 161-168 (2006);
2. Medalsy, I. et al., *Nano lett.,* 8, 473-477 (2008);
3. Dgany et al, JBC, 2004; 279:51516-23;
4. Chiang et al., J Phys. Chem. B, 2001, 105:8297-8301;
5. Dyke et al., J. Am. Chem. Soc. 2005, 127:4497-4509;
6. Bachilo et al., Science, 2002, 298:2361-2366;
7. Weisman et al., Nano Lett., 2003, 3:1235-1238;
8. Holten-Andersen & Waite *J Dent Res* 87(8):701-709, 2008;
9. Sano, K. I. et al. *JACS.* 125, pp 14234-14235, 2003;
10. Sano, K. I et al., *JACS,* 128, pp 1717-1722, 2006;
11. Sano, K. I. et al., *Nano Lett.,* 7, pp 3200-3202, 2007;
12. Sarikaya et al., *Ann. Rev. Mater. Res.,* 2004, 34, 373-408
13. Nature materials, 2003, 2, 196;
14. Nano lett., 2006, 6, 40-44;
15. Langmuir, 2004, 20, 8939-8941

What is claimed is:

1. A composition of matter comprising carbon nanotubes non-covalently bound to chimeric stable protein 1 (SP1) polypeptide dispersed within a polymer resin, wherein said chimeric SP1 polypeptide:
   i) has at least 85% amino acid sequence identity to SEQ ID NO:4;
   ii) forms stable dimers; and
   iii) has a carbon nanotube binding peptide at the N-terminus of said SP1 polypeptide,
   wherein said carbon nanotubes are nanoscale hollow cylinders of graphite carbon atoms.

2. The composition of matter of claim 1, wherein said carbon nanotube binding peptide has an amino acid sequence selected from the group consisting of SEQ ID NOs: 10-12 and 13.

3. The composition of matter of claim 1, wherein said chimeric SP1 polypeptide has the amino acid sequence as set forth in any one of SEQ ID NOs: 6, 8, 9, 14-18 and 86.

4. The composition of matter of claim 1, wherein said chimeric SP1 polypeptide has the amino acid sequence as set forth in SEQ ID NO: 8.

5. The composition of matter of claim 1, wherein said polymer resin is a naturally occurring polymer or a synthetic polymer resin.

6. The composition of matter of claim 5, wherein said naturally occurring polymer is selected from the group consisting of natural rubber, protein, carbohydrate and nucleic acid.

7. The composition of matter of claim 5, wherein said synthetic polymer resin is a thermoplastic or a thermosetting polymer resin.

8. The composition of matter of claim 7, wherein said thermoplastic polymer resin is selected from the group consisting of a polysulfone, a polyamide, a polycarbonate, a polyphenylene oxide, a polysulfide, a polyether ether ketone, a polyether sulfone, a polyamide-imide, a polyetherimide, a polyimide, a polyarylate, a polyolefin and a liquid crystalline polyester.

9. The composition of matter of claim 8, wherein said polyolefin is selected from the group consisting of polyethylene, polypropylene, polystyrene, polyvinyl chloride, polyacrylate, polymethacrylate, polyacrylamide, polymethacrylamide, polyacrylonitrile, poly(N-vinylcarbazole), poly(N-vinylpyrrolidine), poly(vinyl ether), polyvinyl alcohol), poly(vinylidene fluoride) and polyvinyl fluoride).

10. The composition of matter of claim 7, wherein said thermosetting polymer resin is selected from the group consisting of a phenolic resin, an epoxy resin, an aromatic polyamide (aramid) resin, a bismaleimide resin, a triazine resin, a polyimide resin, and polymethyl methacrylate resin.

11. The composition of matter of claim 1, wherein said polymer resin is an epoxy resin.

12. The composition of matter of claim 1, wherein said polymer resin is a co-polymer resin.

13. The composition of matter of claim 1, wherein said polymer resin further comprises a filler reagent.

14. The composition of matter of claim 1, further comprising at least one agent selected from the group consisting of a material modifying reagent, a hardener, a diluting agent, a filler reagent and a co-polymer.

15. A composite material comprising the composition of matter of claim 1, wherein said polymer resin is a polymerized polymer resin.

16. The composite material of claim 15, wherein said chimeric SP1 polypeptide has the amino acid sequence as set forth in any one of SEQ ID NOs: 6, 8, 9, 14-18 and 86.

17. The composite material of claim 15, wherein said polymer resin is epoxy.

18. The composite material of claim 15, wherein said chimeric SP1 polypeptide has the amino acid sequence as set forth in SEQ ID NO: 8.

19. A composition of matter comprising at least one layer of the composite material of claim 15 bound to a polymer, fabric or polymeric fabric.

20. The composition of matter of claim 19, comprising a plurality of layers of said composite material bound to said polymer, fabric or polymeric fabric.

21. A composition of matter comprising carbon nanotubes non-covalently bound to chimeric stable protein 1 (SP1) polypeptide dispersed within a polymer resin, wherein said chimeric SP1 polypeptide comprises an SP1 polypeptide and a carbon nanotube binding peptide and wherein:
   i) said SP1 polypeptide has at least 90% amino acid sequence identity to SEQ ID NO:4;
   ii) said chimeric SP1 polypeptide forms stable dimers; and
   iii) said chimeric SP1 polypeptide has a carbon nanotube binding peptide at the N-terminus,
   wherein said carbon nanotubes are nanoscale hollow cylinders of graphite carbon atoms.

* * * * *